United States Patent
Wang et al.

(10) Patent No.: US 6,777,441 B2
(45) Date of Patent: Aug. 17, 2004

(54) TRIPTOLIDE ANALOGS FOR THE TREATMENT OF AUTOIMMUNE AND INFLAMMATORY DISORDERS

(75) Inventors: Susheng Wang, Clarkston, GA (US); Dennis C. Liotta, Atlanta, GA (US); James P. Snyder, Atlanta, GA (US); Hariharan Venkatesan, San Diego, CA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/970,089

(22) Filed: Oct. 2, 2001

(65) Prior Publication Data

US 2003/0027806 A1 Feb. 6, 2003

Related U.S. Application Data

(60) Provisional application No. 60/237,557, filed on Oct. 2, 2000.

(51) Int. Cl.⁷ ...................... C07D 311/72; A61K 31/335
(52) U.S. Cl. ........................ 514/475; 549/336
(58) Field of Search ........................... 549/336; 514/475

(56) References Cited

U.S. PATENT DOCUMENTS 4,522,811 A    6/1985    Eppstein et al.

FOREIGN PATENT DOCUMENTS

| GB | 2 104 516 | 3/1983 |
|---|---|---|
| WO | US94/02540 | 2/1994 |

OTHER PUBLICATIONS

Briggs J. D., *Immunology Letters* Jul. 29(1–2):89–94 (1991).
Keown, P. A., *Ann. Rev. Trans., Clin. Transplants* 205–223, (1991).
Platt, J. L., et al., *Immunol. Today* 11(2):450 (1990).
Roberts, J. P., et al., *Ann. Rev. Med.*, 40:287 (1989).
Arenz, Christoph, et al. *Angewandte* Chemie, Int. Ed. 39(8) 2000, pp. 1440–1142.
Baldwin, Jack E. et al., *Tetra. Letters*, 21, 1980, 4971–4972.
Blewer, R.S. et al., *J. of Nuclear Materials*, 4()3), 1972, pp. 260–278.
Gesson, J.P. et al., *Tetra. Letters*, 34(18), 1993, pp. 2941–2944.
Yang, Dan et al., *Tetra. Letters* 38(39), 1997, 6865–6868.

*Primary Examiner*—Bruck Kifle
(74) *Attorney, Agent, or Firm*—Sherry M. Knowles, Esq.; King & Spalding, LLP

(57) ABSTRACT

The present invention provides synthetic methods and compositions for treatment of autoimmune and anti-inflammatory disorders comprising administering an effective amount of a derivative of triptolide alone or in combination or alternation with other anti-autoimmune or anti-inflammatory compounds.

42 Claims, 4 Drawing Sheets

TRIPTOLIDE ANALOGS FOR THE TREATMENT OF AUTOIMMUNE AND INFLAMMATORY DISORDERS

FIELD OF THE INVENTION

The present invention is in the area of pharmaceutical chemistry and specifically relates to novel compounds and pharmaceutical compositions for the treatment of autoimmune and inflammatory disorders. This application claims priority to U.S. Ser. No. 60/237,557, filed on Oct. 2, 2000.

BACKGROUND OF THE INVENTION

Autoimmune and inflammatory diseases affect more than fifty million Americans. The immune system functions as the body's major defense against diseases caused by invading organisms. This complex system fights disease by killing invaders such as bacteria, viruses, parasites or cancerous cells while leaving the body's normal tissues unharmed. The immune system's ability to distinguish the body's normal tissues, or self, from foreign or cancerous tissue, or non-self, is an essential feature of normal immune system function. A second essential feature is memory, the ability to remember a particular foreign invader and to mount an enhanced defensive response when the previously encountered invader returns. The loss of recognition of a particular tissue as self and the subsequent immune response directed against that tissue produce serious illness.

Inflammation is involved in a large number of physiological and pathological conditions affecting animals and humans. Inflammatory responses can usually be traced to an immune response to an antigen, allergen, irritant, endotoxin or to tissue damage. The process is complex, involving a large number of components, many of which display pleiotropic effects, many of which are amplifiers or inhibitors of other components. While many instances of an inflammatory response are well-controlled and self-limited, many pathologic conditions arise from uncontrolled or inappropriate responses, resulting in both acute and chronic conditions.

As a result of basic research in molecular and cellular immunology over the last ten to fifteen years, approaches to diagnosing, treating and preventing these immunological based diseases have been changed forever. By dissecting the individual components of the immune system, those cells, receptors and mediators that are critical to the initiation and progression of immune responses have been, and continue to be, elucidated. Crystallographic analysis of proteins encoded in the major histocompatability complex, identification of an antigen-specific T cell receptor, and development of a basic understanding of the complex cytokine network have all contributed to a revolution in immunology. Various immunosuppressive agents have proved to be useful in the prevention of transplantation rejection and in the treatment of autoimmune diseases such as rheumatoid arthritis, nephritis, uveitis, thyroiditis, and early stage of insulin dependent diabetes mellitus, systemic lupus erythematosus, psoriasis and inflammatory bowel disease.

The immune system when operating normally is involved in precise functions such as recognition and memory of, specific response to, and clearance of, foreign substances (chemical and cellular antigens) that either penetrate the protective body barriers of skin and mucosal surfaces (transplanted tissue and microorganisms such as bacteria, viruses, parasites) or arise de novo (malignant transformation). The arsenal of the immune response is composed of two major types of lymphocytes that are either B-lymphocytes (B cells, responsible for producing antibodies which attack the invading microorganisms) or the T-lymphocytes (T cells, responsible for eliminating the infected or abnormal target cells) in cooperation with macrophages. The cascade of principal events in the immune system is more fully described by I. Roitt, J. Brostoff and D. Male in "Immunology", 3rd edition, Mosby, 1993 which is herein incorporated by reference, and may be summarized as follows.

The response is initiated by the interaction of an antigen with macrophages and surface antibodies on B cells. The macrophages ingest and process the antigen. The activated macrophages secrete interleukin-1 (IL-1) and tumor necrosis factor (TNF), and display the processed antigen on the cell surface together with a major antihistocompatibility antigen. Both IL-1 and TNF initiate a number of processes involving inflammation. Also, IL-1 induces proliferation of B cells and synthesis of antibodies. But more importantly, IL-1 activates T cells that release a series of lymphokines including interleukin-2 (IL-2) that activate the proliferation of T cells and cytotoxic lymphocytes. In autoimmune diseases, the system is unable to distinguish between "non-self" antigen and "self" antigen and will start to produce autoantibodies or autoreactive T cells that attack the normal components of the body.

Inflammatory reactions differ not only as to the nature of the triggering event, but also in the types of cells mediating the response and in the biochemical nature of the end effectors. In particular, inflammation mediated by monocyte/macrophage activity can result in severe chronic or fatal conditions, including immune complex-initiated primary inflammatory disorders such as glomerulonephritis, chronic interstitial nephritis, interstitial pneumonitis, Crohn's disease, ulcerative colitis, osteoarthritis, biliary cirrhosis and the like, affecting other organ systems; also including connective tissue diseases such as rheumatoid arthritis, systemic lupus erythematosus and the like; further including secondary progressive inflammatory diseases in which the central cause of tissue destruction is uncontrolled inflammatory/fibrotic processes regardless of the nature of the initiating insult, for example chronic hepatitis, whether the initial insult be infectious, toxic, alcohol, etc., radiation induced chronic inflammations of lung, kidney, central nervous system, inflammations induced by crystal deposition, such as gout, and various forms of post-traumatic inflammatory injury, such as arthritis. Many prior therapeutic strategies have been directed at alleviating the various symptoms of the diseases, without affecting the process itself.

Leukocyte activation leads to the release of degradative enzymes, the generation of reactive oxygen species and the biosynthesis of locally acting pro-inflammatory autacoids. Among the latter, oxygenated metabolites of arachidonic acid are recognized major products of leukocyte activation and exert potent biological effects on cellular functions. The arachidonate lipoxygenase (LO) family of enzymes catalyze the formation of highly potent biologic mediators in leukocytes and platelets. The predominant LO pathway in polymorphonuclear leukocytes (PMN) and macrophages is 5-LO, leading to the formation of leukotrienes (LTs) and 5-hydroxyeicosatetraenoic acid (5-HETE) (Samuelson, B. et al. (1987) Science 237:1171–1176). The sulfidopeptide LTs ($LTC_4$, $LTD_4$, and $LTE_4$) and the non-peptidyl $LTB_4$, elicit potent biological responses: $LTC_4$ and $LTD_4$ contract vascular, pulmonary, and gastrointestinal smooth muscle, and increase vascular permeability to macromolecules (Lewis, R. A. et al. (1984) J. Clini. Invest. 73:889–897; Samuelson, B. et al. (1987) supra). $LTB_4$ has minimal spasmogenic properties. Its primary target appears to be (PMN)s, which express specific high and low affinity receptors for $LTB_4$. Through the former, $LTB^4$ is the most potent chemotactic substance yet described for this cell and also increases PMN aggregation and adhesion to endothelium. Through the latter, it acts as a calcium ionophore, leading to PMN activation, stimulation of phosphoinositide turnover, release of lysosomal enzymes and an increase in oxidative metabolism. In turn, activated PMNs are the best studied source of $LTB_4$ where its synthesis is coupled to activation of protein kinase C.

Direct effects of $LTC_4$, $LTD_4$ and $LTB_4$ on normal and inflamed glomerulus have been measured. $LTA_4$ is a product of 5-LO activity and serves as a precursor for both $LTC_4$ and $LTB_4$. The former requires the activity of a glutathione-S-transferase while the latter is the product of $LTA_4$ hydrolase. $LTD_4$ is the product of a .gamma.-glutamyl transferase removing a glutamyl moiety from $LTC_4$. $LTD_4$ has a powerful effect of reducing glomerular capillary ultrafiltration coefficient acting on both normal and inflamed glomeruli. It is believed to be a major mediator of functional deterioration in glomerulonephritis. $LTC_4$ has been shown to reduce renal blood flow and glomerular filtration rate acting on normal kidney and is considered to act similarly in inflamed glomerulus. By contrast, $LTB_4$ has little direct effect on normal glomerulus. However it is a powerful chemotactic agent for PMNs. The role of $LTB_4$ in glomerulonephritis is seen as an indirect amplifier of leukocyte-dependent reductions in glomerular perfusion due to enhancement of PMN recruitment and activation.

An alternative metabolic pathway initiated by 15-lipoxygenase (15-LO) activity leads to compounds having antagonistic effects to the products of 5-LO activity. Hydroperoxidation of arachidonic acid by 15-LO leads to the formation of 15-S-hydroxyeicosatetraenoic acid (15-S-HETE). Dual lipoxygenation at both the 5 and 15 positions in activated neutrophils and macrophages yields a class of "lipoxygenase interaction products" (Samuelson, B. et al. (1987), supra). Like 5-LO, 15-LO gene expression is restricted largely to leukocyte cell lines, but has also been detected in reticulocytes and airway epithelial cells. Using cDNA probes for human 15-LO, gene expression in glomerular cell lines has not been detected by northern analysis. Macrophages are a particularly rich source of 15-LO and hence of 15-S-HETE and LXs. Three biologically active lipoxins have been identified. $LXA_4$, (5S,6R,15S)-5,6,15-trihydroxy-7,9,13-trans-11-cis-eicosatetraenoic acid, $LXB_4$ (5S,14R,15S)-5,14,15-tri-hydroxy-6,10,12-trans-8-cis-eicosatetraenoic acid, and 7-cis-11-trans-$LXA_4$ (Samuelson, B. et al. (1987), supra; Nicolau, K. C. et al. (1989) Biochem. Biophys. Acta 1003:44–53; the pharmacological profile of their renal actions has been characterized recently (Katoh, T. et al. (1992) Am. J. Physiol. 263:F436–442). Lipoxin synthesis, like that of leukotrienes, can also occur via transformation of leukocyte-generated $LTA_4$ by either 15-LO or 12-LO in adjoining cells, such as mesangial cells or platelets.

Evidence for a generalized anti-inflammatory role for 15-LO products has been derived from clinical observations and experimental studies in vivo and in vitro. Administration of 15-S-HETE causes regression of psoriatic lesions in humans and significantly reduces the clinical severity of a canine arthritis model.

The compound, 15-S-HETE, is a specific antagonist of $LTB_4$-induced chemotaxis of PMNs. Other chemotactically-active substances are not inhibited. 15-S-HETE also aborts leukocyte activation, abrogates adhesion of PMNs to endothelium and depresses $LTB_4$ synthesis by leukocytes. During experimental glomerulonephritis, production of $LTB_4$ reaches a peak about three hours after injury and declines to baseline levels after about 72 hours. In contrast, 15-S-HETE levels increase gradually over time up to two weeks, reaching levels consistent with the amounts required to achieve the antagonistic effects just described. The kinetics are consistent with the view that a slower-acting 15-LO pathway functions to inhibit and limit the intensity and scope of an inflammatory process, once the process has been initiated. The lipoxins, especially $LXA_4$, also have significant anti-inflammatory functions. For example, $LXA_4$ acts as an antagonist of the leukotrienes, having anti-chemotactic effect, and having direct vasorelaxation activity and augmentation of glomerular filtration rates. $LXA_4$ acts as a competitive inhibitor of $LTD_4$ receptor binding. $LXA_4$ also prevents or inhibits PMN adhesion to mesangial cells.

The manifold response modalities of the immune systems of mammals are regulated by a variety of secreted immunregulatory proteins termed cytokines. These include various colony stimulating factors, chemokines, interleukins and interferon-$\gamma$ (IFN-$\gamma$). The characteristics of a variety of immune-type responses is largely controlled by the cell types involved and the cytokine network associated therewith in each case. For example, the involvement of the Th1 subset of helper T-cells leads to secretion of IFN-gamma and interleukin-2 (IL-2) which appear to promote a delayed-type hypersensitivity response. Another type of response, mediated by Th2 subset of helper T cells, is characterized by secretion of IL-4 and IL-5, which act to promote antibody responses (Mosmann, T. R. et al. (1989) Annu. Rev. Immunol. 7: 145–173). There is a complex series of positive or negative responses to each set of cytokines by many cell types in the immune system. Much has been learned concerning the function of cytokine networks. However new findings and newly discovered cytokines often require those skilled in the art to revise their theories of cytokine network interactions.

The system of experimentally induced glomerulonephritis in the rat has yielded significant information as to the processes of disease development and the nature of the biochemical mediators of tissue destruction. See Badr, K. (1992) Kidney International 42(Suppl. 38): S-101-S-108, incorporated herein by reference. The presence of immune complexes in the glomerulus, regardless of their sources, routes of formation, or intraglomerular localization, inevitably and necessarily provokes a complement-mediated influx and activation of polymorphonuclear leukocytes (PMN). The very transient nature of the PMN infiltrate (first few hours following immune activation) renders it an infrequent finding in renal biopsies from patients with various forms of glomerulonephritis, leading to under-appreciation of the potential role of this early inflammatory event in the eventual outcome of disease. PMNs are, however, detected frequently when biopsies are performed during ongoing acute injury such as in patients with post-infectious glomerulonephritides. Characteristically, this initial wave of neutrophil infiltration/activation is replaced by monocyte infiltration and macrophage proliferation and activation. During this secondary ("autologous") phase, it is postulated that injury might be perpetuated not only by the consequences of activation/proliferation of macrophages and indigenous glomerular cells (particularly mesangial and epithelial cells), but also by fresh immune reactions to neo-antigens from host tissue exposed as a result of proteolytic and lipid peroxidative consequences of initial leukocyte activation and degranulation. The number of participating cells in the more chronic phase of immune injury, the interactions among these "stimulated" cell populations, and, consequently, the myriad of peptide and lipid-derived mediators which underlie cellular injury and the eventual replacement of normal glomerular architecture by extracellular matrix (fibrosis), is staggering. While strategies aimed at arresting glomerular injury by targeting the mediators of matrix expansion and scar formation show promise, the complexity of the "mediator soup" during this phase of injury and the various cell populations involved (including tubulointerstitial elements) present serious theoretical and practical obstacles to the development of effective therapeutic interventions.

Targeting the mechanisms which govern the severity of early immune-mediated injury rests on the premise that those diseases which most commonly lead to renal failure due to immune deposition are, for the most part, progressive over months to years, suggesting incremental phases of nephron loss. Evidence from pathologic examinations in several forms of glomerulonephritis indicates that injury is heterogeneous: the number of affected versus healthy glomeruli varies among patients, as well as over time in individual patients. Moreover, within individual glomeruli, lesions are often segmental with inflammatory reactions present in certain lobules, while others are totally normal. These data, as well as a clinical course characterized by steadily diminishing renal reserve over highly varying periods of time, suggest strongly that, in an individual patient, "early" injury is occurring continuously in some fixed proportion of nephrons. It is therefore reasonable to predict that institution of therapy which specifically targets those early events will arrest initial injury in those nephrons, albeit small in number, in which it is underway and, more importantly, prevent or abort its development in intact nephrons, despite the potential continued deposition or formation of immune complexes in these normal glomeruli. This latter assumption is based on the dramatic evidence from experimental studies indicating that mere deposition of antigen-antibody complexes in the glomerular capillary wall or mesangium, in the absence of cellular infiltration (as in leukocyte- or complement-depleted animals) or the capacity to generate arachidonate metabolites (as in fatty acid deficient animals), is without any detrimental acute or chronic consequences to glomerular structure and functions.

Each element in the cascade of the immune response may be considered as a potential site for pharmacological intervention. For example, adrenocorticosteroids act in the first stages of the immune response, interact with the macrophages and, inhibit the synthesis and release of IL-1. Other immunosuppressive agents used in the treatment of autoimmune diseases have been identified, such as azathioprine and methotrexate for rheumatoid arthritis, cyclophosphamide for nephritic conditions of immune origin, and cyclosporin for rheumatoid arthritis, uveitis, early onset insulin dependent diabetes mellitus, psoriasis, nephritic syndrome and aplastic anemia.

In addition, immunosuppressive agents have proved to be useful in preventing and treating organ transplantation rejection that may occur in allograft transplantation. In allograft transplantation one person donates an organ to a genetically disparate individual while in xenograft transplantation an organ of one species is transplanted into a member of another species. In those cases, the use of cyclosporin has shown a real improvement in the condition of the person receiving the organ. However, the therapeutic index of the available immunosuppressive drugs is narrow, none of the drugs are completely effective and their use has been limited by severe toxicity.

Autoimmune disease results from the immune system attacking the body's own organs or tissues, producing a clinical condition associated with the destruction of that tissue. An autoimmune attack directed against the joint lining tissue results in rheumatoid arthritis; an attack against the conducting fibers of the nervous system results in multiple sclerosis. The autoimmune diseases most likely share a common pathogenesis and the need for safe and effective therapy.

Rheumatoid arthritis is one of the most common of the autoimmune diseases. Current treatments utilize three general classes of drugs (Schumacher, H. R. ed., Pimer on the Rheumatic Diseases, Ninth edition, Arthritis Foundation, Atlanta, Ga. (1988): anti-inflammatory agents (aspirin, nonsteroidal anti-inflammatory drugs and low dose corticosteriods); disease-modifying antirheumatic drugs, known as "DMARDs" (anti-malarials, gold salts, penicillamine, and sulfasalazine) and immunosuppressive agents (azathioprine, chlorambucil, high dose corticosteroids, cyclophosphamide, methotrexate, nitrogen mustard, 6-mercaptopurine, vincristine, hydroxyurea, and cyclosporin A). None of the available drugs are completely effective, and most are limited by severe toxicity.

In addition to their use in treating autoimmune conditions, immunosuppressive agents have also been used in treating or preventing transplantation rejection. Organ transplantation involving human organ donors and human recipients (allografts), and non-human primate donors and human recipients (xenografts), has received considerable medical and scientific attention (Roberts, J. P., et al., Ann. Rev. Med., 40:287 (1989); Platt, J. L., et al., Immunol. Today 11(2):450 (1990); Keown, P. A., Ann. Rev. Trans., Clin. Transplants 205–223, (1991). To a great extent, these efforts has been aimed at eliminating, or at least reducing, the problem of rejection of the transplanted organ. In the absence of adequate immunosuppressive therapy, the transplanted organ is destroyed by the host immune system.

Presently, the most commonly used agents for preventing transplant rejection include corticosteriods, antimetabolite drugs that reduce lymphocyte proliferation by inhibiting DNA and RNA synthesis such as azathioprine, immunosuppressive drugs such as cyclosporin A, which specifically inhibits T cell activation, and specific antibodies directed against T lymphocytes or surface receptors that mediate their activation (Briggs J. D., Immunology Letters July 29(1–2):89–94 (1991). All of these drug therapies are limited in effectiveness, in part because the doses needed for effective treatment of transplant rejection may increase the patient's susceptibility to infection by a variety of opportunistic invaders, and in part because of direct toxicity and other side effects. For example, cyclosporin A, currently the most commonly used agent, is significantly toxic to the kidney. This nephrotoxicity limits the quantity of drug that can be safely given.

Many useful pharmaceutical agents are derived from plants. In some cases, the plant-derived compound provides a drug lead that is then chemically modified to improve its pharmacological activity and/or simplify its structure for chemical synthesis. In many cases, e.g., where the plant-derived compound is a complex structure, chemical synthesis is impractical, and the compound must be obtained by direct extraction from plants. If the plant is in short supply, or a complex purification scheme is required, or the yield is low, direct extraction from plants may not be practical.

Production of pharmaceutical agents using plant cell cultures has been reported for only a few cases. In general, obtaining what are usually complex compounds by this approach has not been feasible to date.

One plant that illustrates the potential for plant secondary metabolites as useful pharmaceutical agents, and also the difficulty of producing the plant products in practical yields, is *Tripterygium wilfordii* (TW). A number of compounds having immuno-suppressive or other activities have been isolated from extracts of root tissues from TW, including tripterinin (PCT Application PCT/US94/02540), 16-hydroxytriptolide (Ma, 1991a; 1992a), triptriolide (Ma, 1991b), celastrol (Zhang, 1986a,b), tripchlorolide (Zhang, 1992), triptophenolide (Deng, 1992), triptonide (Wu, 1992), tripterine (Zhang, 1990a), tripterygic acid (Zhang, 1990b), sesquiterpene alkaloids (Ya, 1990), isowilfordine (Ya, 1991), sesquiterpene esters (Takaishi, 1990; 1991a; 1992a), sesquiterpene polyol esters (Takaishi, 1991b,c), phenanthrene derivatives (Takaishi, 1991d) tripterygone (Zhang, 1991), salaspermic acid (Chen, 1992), other diterpene lactone epoxide compounds (Zheng, 1991; Ma, 1992b), and diterpene quinones (Shen, 1992; Takaishi, 1992b; Shishido, 1993).

It has now been discovered that various extracts from the poisonous plant *Tripterygium wilfordii* play an important part in autoimmune and inflammatory suppression, in particular, triptolide. Triptolide contains and unusual triepoxide moiety and an α,β unsaturated γ-lactone in the diterpene skeleton, and it has potent antileukemic and immunosuppressive activities.

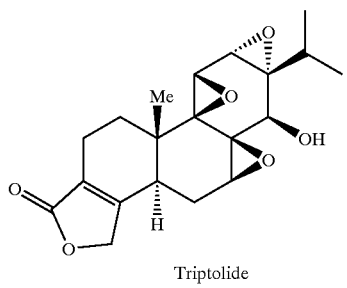

Triptolide

However, in most cases, these compounds are structurally complex molecules which are difficult to purify in useful quantities from plants, and difficult or impossible to synthesize in practical yields. The activity from the crude compounds found in *T. wilfordii* shows activity, however after purification the activity decreases. The isolated compounds have also been shown to decompose over time and the process is quite slow. At present, it is not known whether cultured cells from *T. wilfordii* could be induced to produce any of these compounds in commercially useful amounts.

It would therefore be desirable to provide immunosuppressive compounds by methods that overcome the limitations noted above. Additionally, it is further desired to provide immunosuppressive compounds having improved water solubility and low toxicity. At the same time it would be advantageous to discover additional plant-derived compounds, or mimics thereof, with therapeutically useful properties. In addition, it would be desirable for such compounds to exhibit immunosuppressive activity in their water soluble form, or to be convertible to an immunosuppressive form by metabolic processes in vivo or in vitro.

SUMMARY OF THE INVENTION

The present invention provides novel compounds, pharmaceutical compositions and methods for the treatment or prophylaxis of autoimmune or inflammatory disorders. These compounds may act by inducing 15-lipoxygenase (15-LO) in the treatment of such disorders.

In particular, compounds are provided of the formula (I)–(XX):

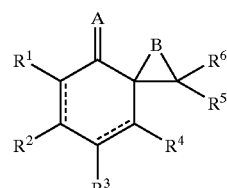
(I)

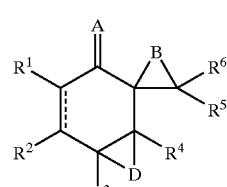
(II)

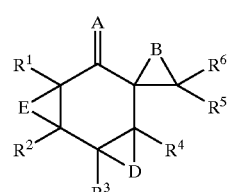
(III)

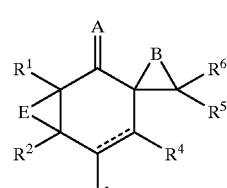
(IV)

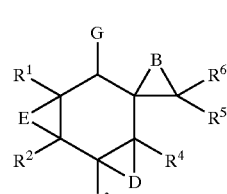
(V)

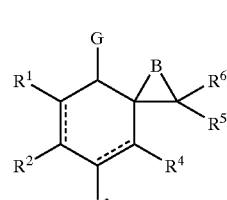
(VI)

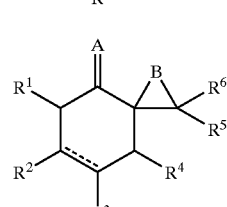
(VII)

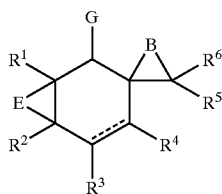
(VIII)

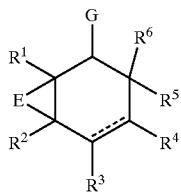
(IX)

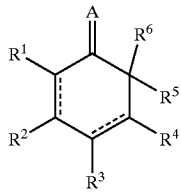
(X)

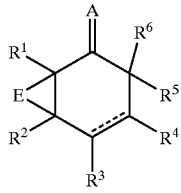
(XI)

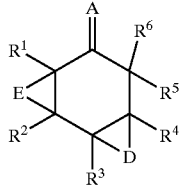
(XII)

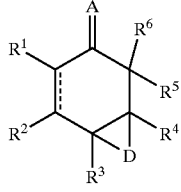
(XIII)

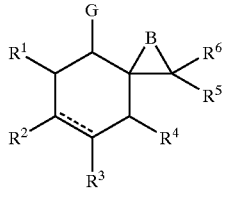
(XIV)

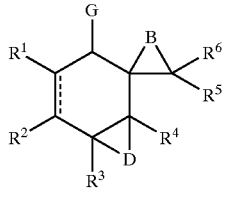
(XV)

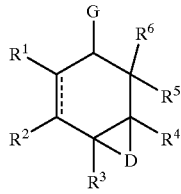
(XVI)

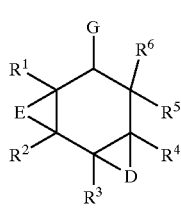
(XVII)

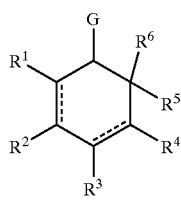
(XVIII)

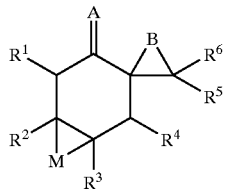
(XIX)

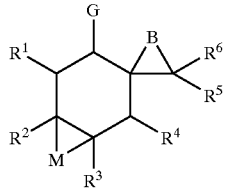
(XX)

and their pharmaceutically acceptable salts and/or prodrugs, thereof, wherein:

each dotted line indicates the presence of either a single or double bond, wherein the valences of a single bond are completed by hydrogens;

each A, B, D, E and M is independently O, S, $NR^7$ or $CR^7R^8$;

each G is independently $OR^{11}$, $NR^{11}R^{12}$ or $SR^{11}$;

each $R^1$, $R^2$, $R^3$, $R^4$, $R^5$ and $R^6$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In a preferred embodiment, the compound exhibits an $EC_{50}$ of less than 25, 15, 10, 5 or 1 micromolar.

In another further embodiment of the present invention is to provide a novel and efficient method for the synthesis of the compounds.

In yet another embodiment of the invention, the compounds of the present invention are administered optionally in a pharmaceutically acceptable carrier or diluent.

In yet another embodiment, the active compound can be administered in combination or alternation with another immunosuppressant or anti-inflammatory agent. In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In yet another embodiment of the invention, compositions comprising the compounds of the present invention, optionally in a pharmaceutically acceptable carrier or diluent, in combination with another immunosuppressant or anti-inflammatory agent are provided.

In yet another embodiment, a method for the treatment or prophylaxis of autoimmune or inflammatory disease in a host is provided, comprising administering an effective amount of an active compound of the present invention, optionally in a pharmaceutically acceptable carrier, optionally in combination or alternation with one or more other immunosuppressant or anti-inflammatory agent.

In yet another embodiment, a method for the treatment or prophylaxis of autoimmune or inflammatory disease in a host is provided, comprising administering a pharmaceutical composition comprising an effective amount of an active compound of the present invention, optionally in a pharmaceutically acceptable carrier, in combination with one or more other immunosuppressant or anti-inflammatory agent.

In yet another embodiment, a use of an effective amount of an active compound of the present invention, optionally in a pharmaceutically acceptable carrier, optionally in combination or alternation with one or more other immunosuppressant or anti-inflammatory agent for the simultaneous, separate or sequential treatment or prophylaxis of autoimmune or inflammatory disease in a host is provided.

In yet another embodiment, a use of an effective amount of an active compound of the present invention, optionally in a pharmaceutically acceptable carrier, optionally in combination or alternation with one or more other immunosuppressant or anti-inflammatory agent in the manufacture of a medicament for the simultaneous, separate or sequential treatment or prophylaxis of autoimmune or inflammatory disease in a host is provided.

DETAILED DESCRIPTION OF THE INVENTION

Figure 1:
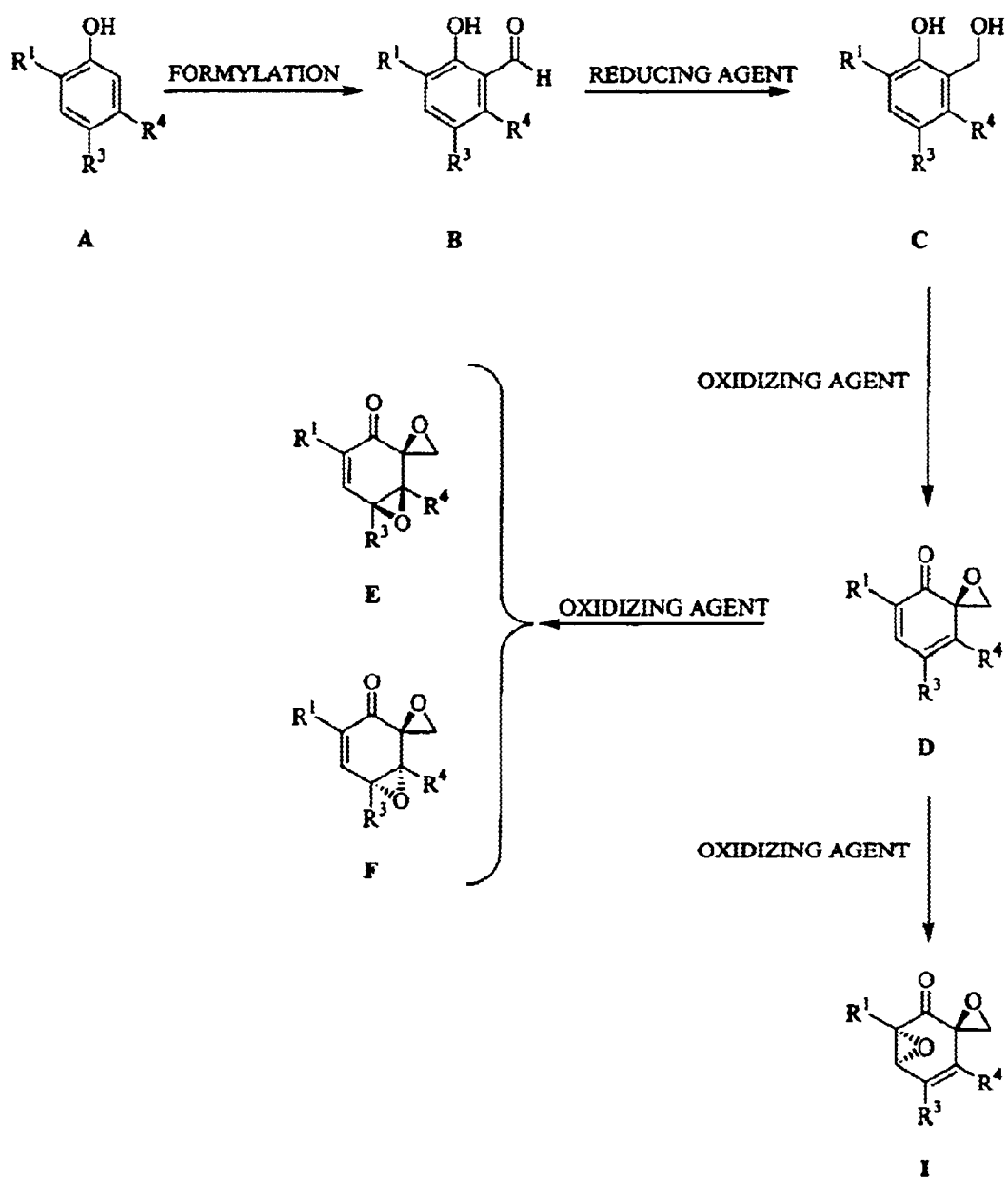
FIG. 1 is a nonlimiting example of the general synthesis for the intermediates of triptolide derivatives.
Figure 2:
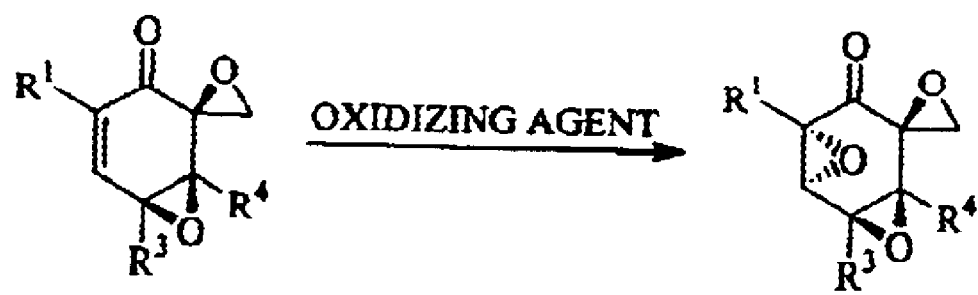
FIG. 2 is a nonlimiting example of the general stereospecific synthesis for triptolide derivatives from intermediates.
Figure 2:
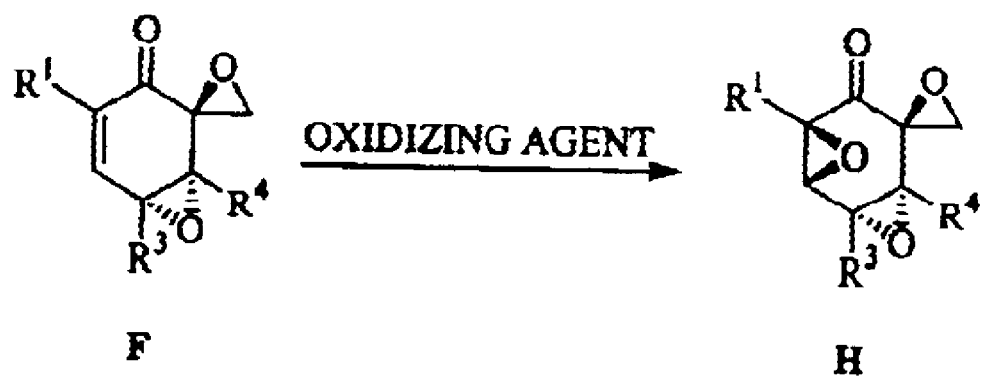
Figure 3:
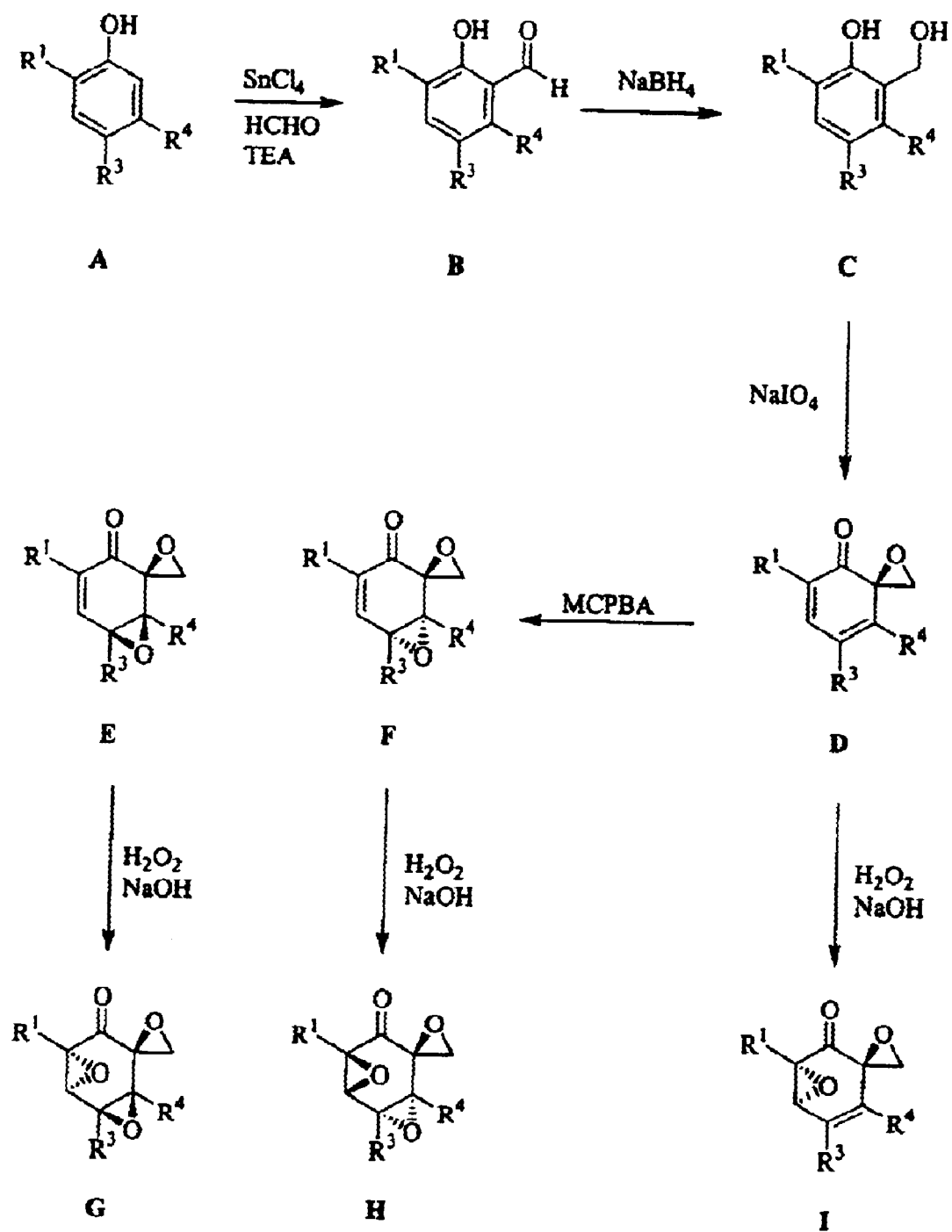
FIG. 3 illustrates one embodiment of the synthesis of triptolide derivatives according to the present invention.
Figure 4:
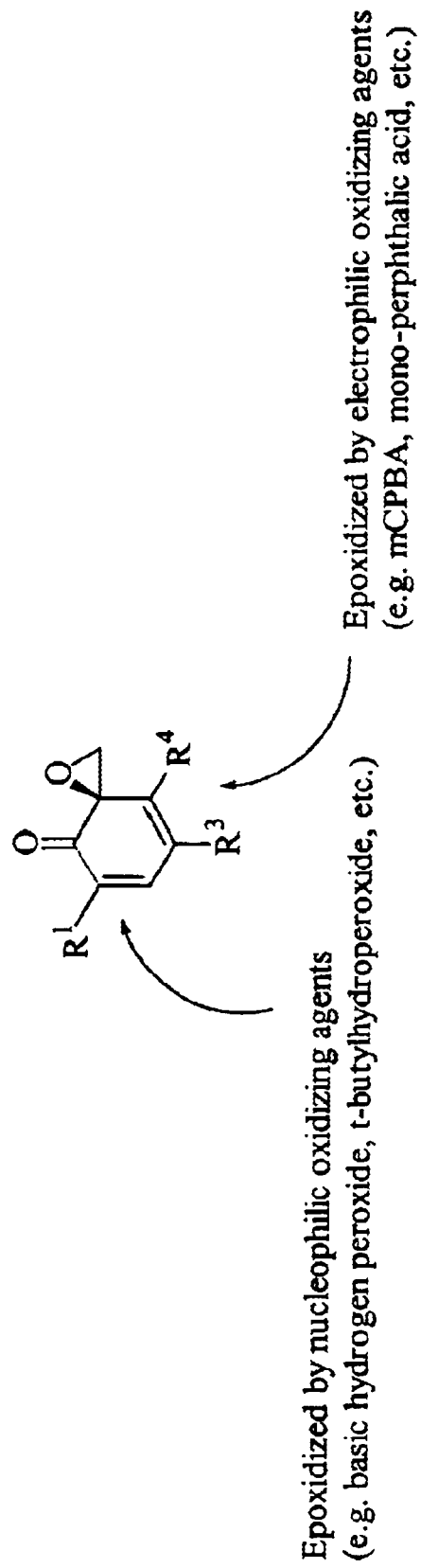
FIG. 4 is a nonlimiting example of general methodologies that can be used to obtain different epoxides of the present invention.

The present invention provides novel compounds, pharmaceutical compositions and methods for the treatment autoimmune and inflammatory disorders. In particular, the present invention relates to novel triptolide derivatives and compositions for the inducement of 15-lipoxygenase (15-LO) in the treatment of autoimmune and anti-inflammatory disorders.

In a preferred embodiment, the compound exhibits an $EC_{50}$ of less than 25, 15, 10, 5 or 1 micromolar.

In another further embodiment of the present invention is to provide a novel and efficient method for the synthesis to the compounds previously mentioned.

In yet another embodiment of the invention, the compounds of the present invention are administered optionally in a pharmaceutically acceptable carrier or diluent.

In yet another embodiment, the active compound can be administered in combination or alternation with another immunosuppressant or anti-inflammatory agent. In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In yet another embodiment of the invention, compositions comprising the compounds of the present invention, optionally in a pharmaceutically acceptable carrier or diluent, in combination with another immunosuppressant or anti-inflammatory agent are provided.

In yet another embodiment, a method for the treatment or prophylaxis of autoimmune or inflammatory disease in a host is provided, comprising administering an effective amount of an active compound of the present invention, optionally in a pharmaceutically acceptable carrier, optionally in combination or alternation with one or more other immunosuppressant or anti-inflammatory agent.

In yet another embodiment, a method for the treatment or prophylaxis of its autoimmune or inflammatory disease in a host is provided, comprising administering a pharmaceutical composition comprising an effective amount of an active compound of the present invention, optionally in a pharmaceutically acceptable carrier, in combination with one or more other immunosuppressant or anti-inflammatory agent.

In yet another embodiment, a use of an effective amount of an active compound of the present invention, optionally in a pharmaceutically acceptable carrier, optionally in combination or alternation with one or more other immunosuppressant or anti-inflammatory agent for the simultaneous, separate or sequential treatment or prophylaxis of autoimmune or inflammatory disease in a host is provided.

In yet another embodiment, a use of an effective amount of an active compound of the present invention, optionally in a pharmaceutically acceptable carrier, optionally in combination or alternation with one or more other immunosuppressant or anti-inflammatory agent in the manufacture of a medicament for the simultaneous, separate or sequential treatment or prophylaxis of autoimmune or inflammatory disease in a host is provided.

I. Compounds of the Present Invention

In one embodiment of the present invention, a structure of the formula (I) is provided:

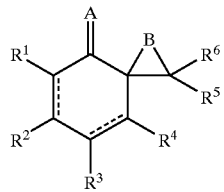

(I)

or its pharmaceutically acceptable salt or prodrug thereof, wherein:

The dotted line indicates the presence of either a single or double bond, wherein the valences of a single bond are completed by hydrogens;

A and B are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (II) is provided:

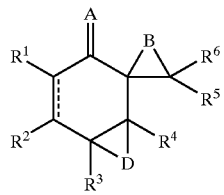

(II)

or its pharmaceutically acceptable salt or prodrug thereof, wherein:

The dotted line indicates the presence of either a single or double bond, wherein the valences of a single bond are completed by hydrogens;

A, B and D are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (III) is provided:

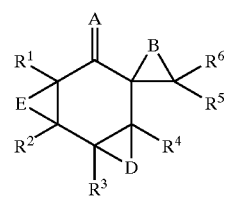

(III)

or its pharmaceutically acceptable salt or prodrug thereof, wherein:

A, B, D and E are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (IV) is provided:

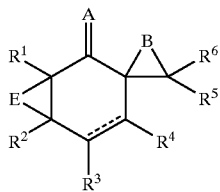

(IV)

or its pharmaceutically acceptable salt or prodrug thereof, wherein:

The dotted line indicates the presence of either a single or double bond, wherein the valences of a single bond are completed by hydrogens;

A, B and E are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (V) is provided:

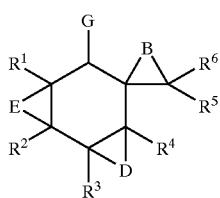

(V)

or its pharmaceutically acceptable salt or prodrug thereof, wherein:

B, D and E are independently O, S, $NR^7$ or $CR^7R^8$;

G is $OR^{11}$, $NR^{11}R^{12}$ or $SR^{11}$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (VI) is provided:

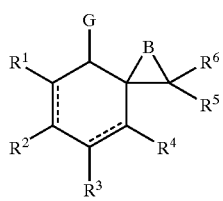

(VI)

or its pharmaceutically acceptable salt or prodrug thereof, wherein:

The dotted line indicates the presence of either a single or double bond, wherein the valences of a single bond are completed by hydrogens;

B is O, S, $NR^7$ or $CR^7R^8$;

G is $OR^{11}$, $NR^{11}R^{12}$ or $SR^{11}$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (VII) is provided:

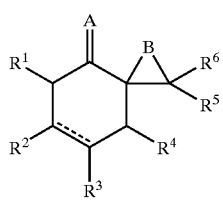

(VII)

or its pharmaceutically acceptable salt or prodrug thereof, wherein:

The dotted line indicates the presence of either a single or double bond, wherein the valences of a single bond are completed by hydrogens;

A and B are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (VIII) is provided:

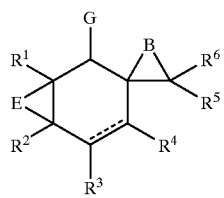

(VIII)

or its pharmaceutically acceptable salt or prodrug thereof, wherein:

The dotted line indicates the presence of either a single or double bond, wherein the valences of a single bond are completed by hydrogens;

B and E are independently O, S, $NR^7$ or $CR^7R^8$;

G is $OR^{11}$, $NR^{11}R^{12}$ or $SR^{11}$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ $^{and\ R2}$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (IX) is provided:

(IX)

or its pharmaceutically acceptable salt or prodrug thereof, wherein:

The dotted line indicates the presence of either a single or double bond, wherein the valences of a single bond are completed by hydrogens;

E is O, S, $NR^7$ or $CR^7R^8$;

G is $OR^{11}$, $NR^{11}R^{12}$ or $SR^{11}$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (X) is provided:

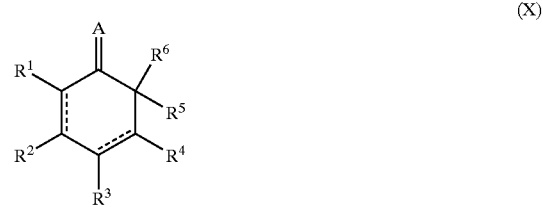

(X)

or its pharmaceutically acceptable salt or prodrug thereof, wherein:

The dotted line indicates the presence of either a single or double bond, wherein the valences of a single bond are completed by hydrogens;

A is O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, bydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XI) is provided:

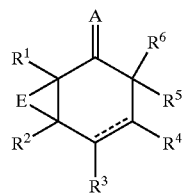

(XI)

or its pharmaceutically acceptable salt or prodrug thereof, wherein:

The dotted line indicates the presence of either a single or double bond, wherein the valences of a single bond are completed by hydrogens;

A and E are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XII) is provided:

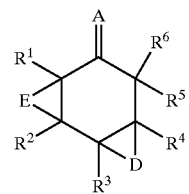

(XII)

or its pharmaceutically acceptable salt or prodrug thereof, wherein:

The dotted line indicates the presence of either a single or double bond, wherein the valences of a single bond are completed by hydrogens;

A, D and E are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XIII) is provided:

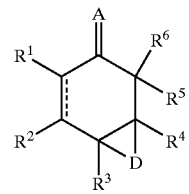

(XIII)

or its pharmaceutically acceptable salt or prodrug thereof, wherein:

The dotted line indicates the presence of either a single or double bond, wherein the valences of a single bond are completed by hydrogens;

A and D are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of R¹ and R², R² and R³, R³ and R⁴, R⁴ and R⁵, or R⁵ and R⁶, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each R⁷, R⁸, R⁹ and R¹⁰ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XIV) is provided:

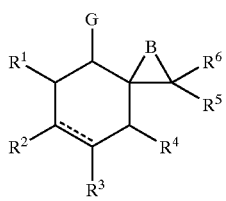

(XIV)

or its pharmaceutically acceptable salt or prodrug thereof, wherein:

The dotted line indicates the presence of either a single or double bond, wherein the valences of a single bond are completed by hydrogens;

B is O, S, NR⁷ or CR⁷R⁸;

G is OR¹¹, NR¹¹R¹² or SR¹¹;

R¹, R², R³, R⁴, R⁵ and R⁶ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or XR⁹ (wherein X=O, S or NR¹⁰);

alternatively, one or more of R¹ and R², R² and R³, R³ and R⁴, R⁴ and R⁵, or R⁵ and R⁶, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each R⁷, R⁸, R⁹, R¹⁰, R¹¹ and R¹² is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XV) is provided:

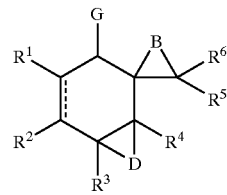

(XV)

or its pharmaceutically acceptable salt or prodrug thereof, wherein:

The dotted line indicates the presence of either a single or double bond, wherein the valences of a single bond are completed by hydrogens;

B and D are independently O, S, NR⁷ or CR⁷R⁸;

G is OR¹¹, NR¹¹R¹² or SR¹¹;

R¹, R², R³, R⁴, R⁵ and R⁶ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or XR⁹ (wherein X=O, S or NR¹⁰);

alternatively, one or more of R¹ and R², R² and R³, R³ and R⁴, R⁴ and R⁵, or R⁵ and R⁶, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each R⁷, R⁸, R⁹, R¹⁰, R¹¹ and R¹² is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XVI) is provided:

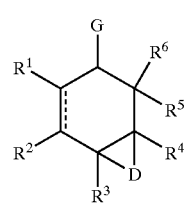

(XVI)

or its pharmaceutically acceptable salt or prodrug thereof, wherein:

The dotted line indicates the presence of either a single or double bond, wherein the valences of a single bond are completed by hydrogens;

D is O, S, NR⁷ or CR⁷R⁸;

G is OR¹¹, NR¹¹R¹² or SR¹¹;

R¹, R², R³, R⁴, R⁵ and R⁶ are independently hydrogen, aLkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XVII) is provided:

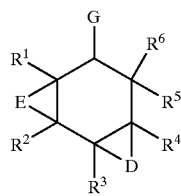

(XVII)

or its pharmaceutically acceptable salt or prodrug thereof, wherein:

The dotted line indicates the presence of either a single or double bond, wherein the valences of a single bond are completed by hydrogens;

D and E are independently O, S, $NR^7$ or $CR^7R^8$;

G is $OR^{11}$, $NR^{11}R^{12}$ or $SR^{11}$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XVIII) is provided:

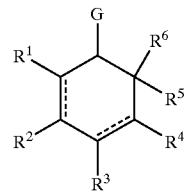

(XVIII)

or its pharmaceutically acceptable salt or prodrug thereof, wherein:

The dotted line indicates the presence of either a single or double bond, wherein the valences of a single bond are completed by hydrogens;

G is $OR^{11}$, $NR^{11}R^{12}$ or $SR^{11}$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XIX) is provided:

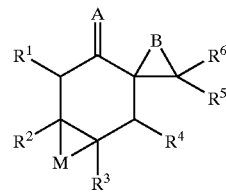

(XIX)

or its pharmaceutically acceptable salt or prodrug thereof, wherein:

The dotted line indicates the presence of either a single or double bond, wherein the valences of a single bond are completed by hydrogens;

A, B and M are independently O, S, $NR^7$ or $CR^7R^8$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$ and $R^{10}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In another embodiment of the present invention a structure of the formula (XX) is provided:

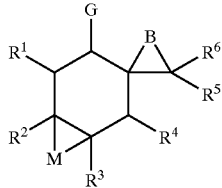

(XX)

or its pharmaceutically acceptable salt or prodrug thereof, wherein:

The dotted line indicates the presence of either a single or double bond, wherein the valences of a single bond are completed by hydrogens;

B and M are independently O, S, $NR^7$ or $CR^7R^8$;

G is $OR^{11}$, $NR^{11}R^{12}$ or $SR^{11}$;

$R^1$, $R^2$, $R^3$, $R^4$, $R^5$ and $R^6$ are independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, carbonyl, carboxylic acid, ester, carbamate, amide, amine, hydroxyl, alkoxide, nitro, cyano, azide, sulfonyl, sulfanyl, sulfinyl, sulfamonyl, phosphonyl, phosphinyl, phosphoryl, phosphine, a residue of a natural or synthetic amino acid, a residue of a natural or synthetic carbohydrate or $XR^9$ (wherein X=O, S or $NR^{10}$);

alternatively, one or more of $R^1$ and $R^2$, $R^2$ and $R^3$, $R^3$ and $R^4$, $R^4$ and $R^5$, or $R^5$ and $R^6$, come together to form a bridged compound, preferably as a 3, 5, 6 or 7 membered ring, to form a cycloalkyl, cycloalkenyl, cycloalkynyl, aryl, heterocyclic, heteroaryl or heteroaromatic; and each $R^7$, $R^8$, $R^9$, $R^{10}$, $R^{11}$ and $R^{12}$ is independently hydrogen, alkyl, alkenyl, alkynyl, cycloalkyl, cycloalkenyl, cycloalkynyl, aryl, alkaryl, arylalkyl, heterocyclic, heteroaryl, heteroaromatic, alkcarbonyl, a residue of a natural or synthetic amino acid or a residue of a natural or synthetic carbohydrate.

In a sub-embodiment, a structure of the formula (I) is given wherein the compound or its pharmaceutically acceptable salts or prodrug is defined as follows:

A and B are independently O, S, $NR^7$ or $CR^7R^8$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and R, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=O, B=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=O, B=$NR^{10}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=O, B=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=O, B=S.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=S, B=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=S, B=$NR^8$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=S, B=$CR^8R^9$.

$R^1$ is selected independently from the groups that include hydrogen, alkyl, cycloalkyl, aryl, alkaryl, arylalkyl, heterocyclic, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=S, B=S.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

$A=CR^8R^9$; B=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

$A=CR^8R^9$, $B=NR^{10}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

$A=CR^8R^9$, $B=CR^{21}R^{22}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (I) is given wherein the compound or its pharmaceutically acceptable salts or prodrug is defined as follows:

A=CR$^8$R$^9$, B=S.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$O or CR$^{15}$R$^{16}$NR$^{17}$;

the dotted line indicates the presence of either a single or double bond, wherein in the presence of a single bond, the valences are completed with hydrogens.

In a particular embodiment of the present invention, the compounds of the formula (I) are the following species:

(I)

| A | B | R$^1$ | R$^2$ | R$^3$ | R$^4$ | R$^5$ | R$^6$ |
|---|---|---|---|---|---|---|---|
| O | O | Me | H | H | H | Me | Me |
| O | O | i-Pr | H | H | H | Me | Me |
| O | O | Ph | H | H | H | Me | Me |
| O | O | Me | Me | H | H | Me | Me |
| O | O | i-Pr | Me | H | H | Me | Me |
| O | O | Ph | Me | H | H | Me | Me |
| O | O | Me | H | Me | H | Me | Me |
| O | O | i-Pr | H | Me | H | Me | Me |
| O | O | Ph | H | Me | H | Me | Me |
| O | O | Me | H | H | Me | Me | Me |
| O | O | i-Pr | H | H | Me | Me | Me |
| O | O | Ph | H | H | Me | Me | Me |
| O | O | Me | H | CH$_2$Ph | H | Me | Me |
| O | O | i-Pr | H | CH$_2$Ph | H | Me | Me |
| O | O | Ph | H | CH$_2$Ph | H | Me | Me |
| O | CH$_2$ | Me | H | H | H | Me | Me |
| O | CH$_2$ | i-Pr | H | H | H | Me | Me |
| O | CH$_2$ | Ph | H | H | H | Me | Me |
| O | CH$_2$ | Me | Me | H | H | Me | Me |
| O | CH$_2$ | i-Pr | Me | H | H | Me | Me |
| O | CH$_2$ | Ph | Me | H | H | Me | Me |
| O | CH$_2$ | Me | H | Me | H | Me | Me |
| O | CH$_2$ | i-Pr | H | Me | H | Me | Me |
| O | CH$_2$ | Ph | H | Me | H | Me | Me |
| O | CH$_2$ | Me | H | H | Me | Me | Me |
| O | CH$_2$ | i-Pr | H | H | Me | Me | Me |
| O | CH$_2$ | Ph | H | H | Me | Me | Me |
| O | CH$_2$ | Me | H | CH$_2$Ph | H | Me | Me |
| O | CH$_2$ | i-Pr | H | CH$_2$Ph | H | Me | Me |
| O | CH$_2$ | Ph | H | CH$_2$Ph | H | Me | Me |

In a sub-embodiment, a structure of the formula (II) is given wherein the compound or its pharmaceutically acceptable salts or prodrug is defined as follows:

A=O, B=O, D=O;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{11}$ (X=O, NR$^{12}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{18}$ (X=O, NR$^{19}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$O or CR$^{15}$R$^{16}$NR$^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=O, B=NR$^{10}$, D=O;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{11}$ (X=O, NR$^{12}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, and R$^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{18}$ (X=O, NR$^{19}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$O or CR$^{15}$R$^{16}$NR$^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=O, B=CR$^8$R$^9$, D=O;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{11}$ (X=O, NR$^{12}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ independently are selected from the groups that include hydrogen, alkyl, alkenyl, alkynyl, cycloalkenyl, cycloalkyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=O, B=S, D=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, aLkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=$CR^8R^9$, B=O, D=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=$CR^8R^9$, B=$CR^{18}R^{19}$, and D=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=$CR^8R^9$, B=$CR^{18}R^{19}$, and D=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=$CR^8R^9$, B=S, and D=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=O, B=O, D=$CR^8R^9$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=O, B=$NR^{10}$, D=$CR^8R^9$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=O, B=$CR^8R^9$, D=$CR^{18}R^{19}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=O, B=S, D=$CR^8R^9$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ (X=O, $NR^{12}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ (X=O, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

A=$CR^8R^9$; B=O, D=$CR^{18}R^{19}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ ($X=O$, $NR^{12}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ ($X=O$, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

$A=CR^8R^9$, $B=NR^{10}$, $D=CR^{18}R^{19}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ ($X=O$, $NR^{12}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ ($X=O$, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

$A=CR^8R^9$, $B=CR^{18}R^{19}$, $D=CR^{20}R^{21}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ ($X=O$, $NR^{12}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ ($X=O$, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In another sub-embodiment, a structure of the formula (II) is given wherein the compound or its pharmaceutically acceptable salts or prodrug is defined as follows:

$A=CR^8R^9$, $B=S$, $D=CR^{18}R^{19}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{11}$ ($X=O$, $NR^{12}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{18}$ ($X=O$, $NR^{19}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$; and the dotted line indicates the presence of either a single or double bond, wherein the presence of a single bond, the valences are completed by hydrogens.

In a particular embodiment of the present invention, the compounds of the formula (II) are the following species:

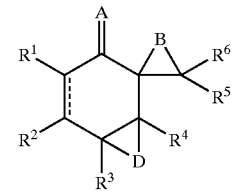

(II)

| A | B | D | $R^1$ | $R^2$ | $R^3$ | $R^4$ | $R^5$ | $R^6$ |
|---|---|---|---|---|---|---|---|---|
| O | O | O | Me | H | H | H | Me | Me |
| O | O | O | i-Pr | H | H | H | Me | Me |
| O | O | O | Ph | H | H | H | Me | Me |
| O | O | O | Me | Me | H | H | Me | Me |
| O | O | O | i-Pr | Me | H | H | Me | Me |
| O | O | O | Ph | Me | H | H | Me | Me |
| O | O | O | Me | H | Me | H | Me | Me |
| O | O | O | i-Pr | H | Me | H | Me | Me |
| O | O | O | Ph | H | Me | H | Me | Me |
| O | O | O | Me | H | H | Me | Me | Me |
| O | O | O | i-Pr | H | H | Me | Me | Me |
| O | O | O | Ph | H | H | Me | Me | Me |
| O | O | O | Me | H | $CH_2Ph$ | H | Me | Me |
| O | O | O | i-Pr | H | $CH_2Ph$ | H | Me | Me |
| O | O | O | Ph | H | $CH_2Ph$ | H | Me | Me |

-continued (II)

[Structure: cyclohexanone-type ring with positions A (top, =R¹ substituent region), B, D, and substituents R¹–R⁶]

| A | B | D | R¹ | R² | R³ | R⁴ | R⁵ | R⁶ |
|---|---|---|----|----|----|----|----|----|
| O | CH₂ | O | Me | H | H | H | Me | Me |
| O | CH₂ | O | i-Pr | H | H | H | Me | Me |
| O | CH₂ | O | Ph | H | H | H | Me | Me |
| O | CH₂ | O | Me | Me | H | H | Me | Me |
| O | CH₂ | O | i-Pr | Me | H | H | Me | Me |
| O | CH₂ | O | Ph | Me | H | H | Me | Me |
| O | CH₂ | O | Me | H | Me | H | Me | Me |
| O | CH₂ | O | i-Pr | H | Me | H | Me | Me |
| O | CH₂ | O | Ph | H | Me | H | Me | Me |
| O | CH₂ | O | Me | H | H | Me | Me | Me |
| O | CH₂ | O | i-Pr | H | H | Me | Me | Me |
| O | CH₂ | O | Ph | H | H | Me | Me | Me |
| O | CH₂ | O | Me | H | CH₂Ph | H | Me | Me |
| O | CH₂ | O | i-Pr | H | CH₂Ph | H | Me | Me |
| O | CH₂ | CH₂ | Ph | H | CH₂Ph | H | Me | Me |
| O | CH₂ | CH₂ | Me | H | H | H | Me | Me |
| O | CH₂ | CH₂ | i-Pr | H | H | H | Me | Me |
| O | CH₂ | CH₂ | Ph | H | H | H | Me | Me |
| O | CH₂ | CH₂ | Me | Me | H | H | Me | Me |
| O | CH₂ | CH₂ | i-Pr | Me | H | H | Me | Me |
| O | CH₂ | CH₂ | Ph | Me | H | H | Me | Me |
| O | CH₂ | CH₂ | Me | H | Me | H | Me | Me |
| O | CH₂ | CH₂ | i-Pr | H | Me | H | Me | Me |
| O | CH₂ | CH₂ | Ph | H | Me | H | Me | Me |
| O | CH₂ | CH₂ | Me | H | H | Me | Me | Me |
| O | CH₂ | CH₂ | i-Pr | H | H | Me | Me | Me |
| O | CH₂ | CH₂ | Ph | H | H | Me | Me | Me |
| O | CH₂ | CH₂ | Me | H | CH₂Ph | H | Me | Me |
| O | CH₂ | CH₂ | i-Pr | H | CH₂Ph | H | Me | Me |
| O | CH₂ | CH₂ | Ph | H | CH₂Ph | H | Me | Me |

In a sub-embodiment, a structure of the formula (III) is given wherein the compound or its pharmaceutically acceptable salts or prodrug is defined as follows:

A=O, B=O, E=O and D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$NR^{20}$, E=O, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^8R^9$, E=O, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=S, E=O, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=O, E=S, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$NR^{10}$, E=S, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^8R^9$, E=S, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=S, E=S, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=O, E=$CR^8R^9$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$NR^{10}$, E=$CR^8R^9$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^{21}R^{22}$, E=$CR^8R^9$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=S, E=$CR^8R^9$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$NR^{10}$, E=$NR^{23}$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^8R^9$, E=$NR^{10}$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=S, E=$NR^{10}$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=O, E=$NR^{10}$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^8R^9$, E=$NR^{10}$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=$CR^8R^9$, B=O, E=O, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=$CR^8R^9$, B=$NR^{10}$, E=O, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=$CR^8R^9$, B=$CR^{20}R^{21}$, E=O, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=S$, $E=O$, $D=O$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=O$, $E=S$, $D=O$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=NR^{10}$, $E=S$, $D=O$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=CR^{20}R^{21}$, $E=S$, $D=O$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=S$, $E=S$, $D=O$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=CR$^8$, B=O, E=CR$^{20}$R$^{21}$, D=O.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

In another sub-embodiment, a structure of the formula (III) is given wherein the compound or its pharmaceutically acceptable salts or prodrug is defined as follows:

A=CR$^8$R$^9$, B=NR$^{10}$, E=CR$^{20}$R$^{21}$, D=O.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

In another sub-embodiment, a structure of the formula (III) is given wherein the compound or its pharmaceutically acceptable salts or prodrug is defined as follows:

A=CR$^8$R$^9$, B=CR$^{20}$R$^{21}$, E=CR$^{22}$R$^{23}$, D=O.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

In another sub-embodiment, a structure of the formula (III) is given wherein the compound or its pharmaceutically acceptable salts or prodrug is defined as follows:

A=CR$^8$R$^9$, B=S, E=CR$^{20}$R$^{21}$, D=O.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

A=CR$^7$R$^8$; B=O.

E=NR$^7$, D=O.

In another sub-embodiment, a structure of the formula (III) is given wherein the compound or its pharmaceutically acceptable salts or prodrug is defined as follows:

A=CR$^8$R$^9$, B=O, E=NR$^{10}$, D=O.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

In another sub-embodiment, a structure of the formula (III) is given wherein the compound or its pharmaceutically acceptable salts or prodrug is defined as follows:

A=CR$^8$R$^9$, B=NR$^{10}$, E=NR$^{24}$, D=O.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=$CR^8R^9$, B=$CR^{20}R^{21}$, E=$NR^{10}$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=$CR^8R^9$, B=S, B=$NR^{10}$, D=O.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=O, E=O, D=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$NR^{10}$, E=O, D=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^8R^9$, E=O, D=$CR^{20}R^{21}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=S, E=O, D=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=O, E=S, D=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$NR^{10}$, E=S, D=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^8R^9$, E=S, D=$CR^{20}R^{21}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=S, E=S, D=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=O, E=$CR^8R^9$, D=$CR^{20}R^{21}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$NR^{10}$, E=$CR^8R^9$, D=$CR^{20}R^{21}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=$CR^8R^9$, E=$CR^{20}R^{21}$, D=$CR^{24}R^{25}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=S, E=$CR^8R^9$, D=$CR^{20}R^{21}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=O, E=$NR^{10}$, D=$CR^8R^9$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

A=O, B=NR$^{10}$, E=NR$^{13}$, D=CR$^8$R$^9$.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, aLkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

A=O, B=CR$^7$R$^8$.

E=NR$^7$, D=CR$^7$R$^8$.

In another sub-embodiment, a structure of the formula (III) is given wherein the compound or its pharmaceutically acceptable salts or prodrug is defined as follows:

A=O, B=CR$^8$R$^9$, E=NR$^{10}$, D=CR$^{20}$R$^{21}$.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

In another sub-embodiment, a structure of the formula (III) is given wherein the compound or its pharmaceutically acceptable salts or prodrug is defined as follows:

A=O, B=S, E=NR$^{10}$, D=CR$^8$R$^9$.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

A=CR$^7$R$^8$; B=O.

E=O, D=CR$^7$R$^8$.

In another sub-embodiment, a structure of the formula (III) is given wherein the compound or its pharmaceutically acceptable salts or prodrug is defined as follows:

A=CR$^8$R$^9$, B=O, E=O, D=CR$^{20}$R$^{21}$.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

In another sub-embodiment, a structure of the formula (III) is given wherein the compound or its pharmaceutically acceptable salts or prodrug is defined as follows:

A=CR$^8$R$^9$, B=NR$^{10}$, E=O, D=CR$^{20}$R$^{21}$.

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$.

In another sub-embodiment, a structure of the formula (III) is given wherein the compound or its pharmaceutically acceptable salts or prodrug is defined as follows:

A=CR$^8$R$^9$, B=CR$^{20}$R$^{21}$, E=O, D=CR$^{24}$R$^{25}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, B=S, E=O, $D=CR^{20}R^{21}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, B=O, E=S, $D=CR^{20}R^{21}$.

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=NR^{10}$, E=S, $D=CR^{21}R^{22}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=CR^{20}R^{21}$, E=S, $D=CR^{24}R^{25}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, B=S, E=S, $D=CR^{20}R^{21}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=O$, $E=CR^{20}R^{21}$, $D=CR^{24}R^{25}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=NR^{10}$, $E=CR^2R^2$, $D=CR^{24}R^{25}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=CR^{20}R^{21}$, $E=CR^{24}R^{25}$, $D=CR^{26}R^{27}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=S$, $E=CR^{21}R^{22}$, $D=CR^{24}R^{25}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=O$, $E=NR^{10}$, $D=CR^{21}R^{22}R$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=NR^{10}$, $E=NR^{23}$, $D=CR^{21}R^{22}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=CR^{21}R^{22}$, $E=NR^{10}$, $D=CR^{24}R^{25}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In another sub-embodiment, a structure of the formula (III) is given wherein the compound or its pharmaceutically acceptable salts or prodrug is defined as follows:

$A=CR^8R^9$, $B=S$, $E=NR^{10}$, $D=CR^{21}R^{22}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$.

In a particular embodiment of the present invention, the compounds of the formula (III) are the following species:

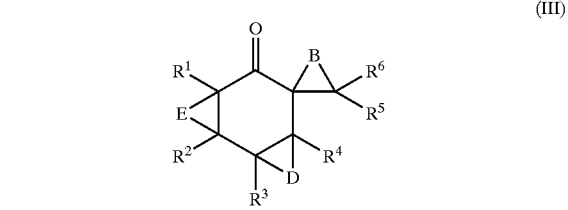

(III)

| B | D | E | $R^1$ | $R^2$ | $R^3$ | $R^4$ | $R^5$ | $R^6$ |
|---|---|---|---|---|---|---|---|---|
| O | O | O | Me | H | H | H | Me | Me |
| O | O | O | i-Pr | H | H | H | Me | Me |
| O | O | O | Ph | H | H | H | Me | Me |
| O | O | O | Me | Me | H | H | Me | Me |
| O | O | O | i-Pr | Me | H | H | Me | Me |
| O | O | O | Ph | Me | H | H | Me | Me |
| O | O | O | Me | H | Me | H | Me | Me |
| O | O | O | i-Pr | H | Me | H | Me | Me |
| O | O | O | Ph | H | Me | H | Me | Me |
| O | O | O | Me | H | H | Me | Me | Me |
| O | O | O | i-Pr | H | H | Me | Me | Me |
| O | O | O | Ph | H | H | Me | Me | Me |
| O | O | O | Me | H | $CH_2Ph$ | H | Me | Me |
| O | O | O | i-Pr | H | $CH_2Ph$ | H | Me | Me |
| O | O | O | Ph | H | $CH_2Ph$ | H | Me | Me |
| $CH_2$ | O | O | Me | H | H | H | Me | Me |
| $CH_2$ | O | O | i-Pr | H | H | H | Me | Me |
| $CH_2$ | O | O | Ph | H | H | H | Me | Me |
| $CH_2$ | O | O | Me | Me | H | H | Me | Me |
| $CH_2$ | O | O | i-Pr | Me | H | H | Me | Me |
| $CH_2$ | O | O | Ph | Me | H | H | Me | Me |
| $CH_2$ | O | O | Me | H | Me | H | Me | Me |
| $CH_2$ | O | O | i-Pr | H | Me | H | Me | Me |
| $CH_2$ | O | O | Ph | H | Me | H | Me | Me |
| $CH_2$ | O | O | Me | H | H | Me | Me | Me |
| $CH_2$ | O | O | i-Pr | H | H | Me | Me | Me |
| $CH_2$ | O | O | Ph | H | H | Me | Me | Me |
| $CH_2$ | O | O | Me | H | $CH_2Ph$ | H | Me | Me |
| $CH_2$ | O | O | i-Pr | H | $CH_2Ph$ | H | Me | Me |
| $CH_2$ | O | O | Ph | H | $CH_2Ph$ | H | Me | Me |
| $CH_2$ | $CH_2$ | O | Ph | H | $CH_2Ph$ | H | Me | Me |
| $CH_2$ | $CH_2$ | O | Me | H | H | H | Me | Me |
| $CH_2$ | $CH_2$ | O | i-Pr | H | H | H | Me | Me |
| $CH_2$ | $CH_2$ | O | Ph | H | H | H | Me | Me |
| $CH_2$ | $CH_2$ | O | Me | Me | H | H | Me | Me |
| $CH_2$ | $CH_2$ | O | i-Pr | Me | H | H | Me | Me |
| $CH_2$ | $CH_2$ | O | Ph | Me | H | H | Me | Me |
| $CH_2$ | $CH_2$ | O | Me | H | Me | H | Me | Me |
| $CH_2$ | $CH_2$ | O | i-Pr | H | Me | H | Me | Me |
| $CH_2$ | $CH_2$ | O | Ph | H | Me | H | Me | Me |
| $CH_2$ | $CH_2$ | O | Me | H | H | Me | Me | Me |
| $CH_2$ | $CH_2$ | O | i-Pr | H | H | Me | Me | Me |
| $CH_2$ | $CH_2$ | O | Ph | H | H | Me | Me | Me |
| $CH_2$ | $CH_2$ | O | Me | H | $CH_2Ph$ | H | Me | Me |
| $CH_2$ | $CH_2$ | O | i-Pr | H | $CH_2Ph$ | H | Me | Me |

-continued

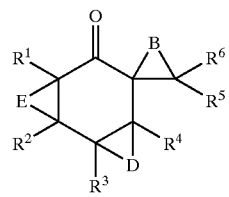

(III)

| B | D | E | R¹ | R² | R³ | R⁴ | R⁵ | R⁶ |
|---|---|---|----|----|----|----|----|----|
| CH₂ | CH₂ | O | Ph | H | CH₂Ph | H | Me | Me |
| CH₂ | O | CH₂ | Me | H | H | H | Me | Me |
| CH₂ | O | CH₂ | i-Pr | H | H | H | Me | Me |
| CH₂ | O | CH₂ | Ph | H | H | H | Me | Me |
| CH₂ | O | CH₂ | Me | Me | H | H | Me | Me |
| CH₂ | O | CH₂ | i-Pr | Me | H | H | Me | Me |
| CH₂ | O | CH₂ | Ph | Me | H | H | Me | Me |
| CH₂ | O | CH₂ | Me | H | Me | H | Me | Me |
| CH₂ | O | CH₂ | i-Pr | H | Me | H | Me | Me |
| CH₂ | O | CH₂ | Ph | H | Me | H | Me | Me |
| CH₂ | O | CH₂ | Me | H | H | Me | Me | Me |
| CH₂ | O | CH₂ | i-Pr | H | H | Me | Me | Me |
| CH₂ | O | CH₂ | Ph | H | H | Me | Me | Me |
| CH₂ | O | CH₂ | Me | H | CH₂Ph | H | Me | Me |
| CH₂ | O | CH₂ | i-Pr | H | CH₂Ph | H | Me | Me |
| CH₂ | O | CH₂ | Ph | H | CH₂Ph | H | Me | Me |

In a sub-embodiment, a structure of the formula (IV) is given wherein the compound or its pharmaceutically acceptable salts or prodrug is defined as follows:

A is O, S or $NR^7$;

B and E are independently selected from $CR^8R^9$, O, S or $NR^{10}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$; and the dotted line indicates the presence of either a single or double bond, wherein in the presence of a single bond, the valences are completed by hydrogens.

In another sub-embodiment, a structure of the formula (IV) is given wherein the compound or its pharmaceutically acceptable salts or prodrug is defined as follows:

A=O, B=O, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=$NR^{10}$, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=$CR^8R^9$, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=S, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=O, E=S;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=$NR^{10}$, E=S;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=$CR^8R^9$, E=S;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=S, E=S;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O; B=O, E=$CR^8R^9$;

$R^1$ is selected independently from the groups that include hydrogen, alkyl, cycloalkyl, aryl, alkaryl, arylalkyl, heterocyclic, ester, alkoarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=$NR^{10}$, E=$CR^7R^8$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=$CR^8R^9$R, E=$CR^{21}R^{22}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=S, E=$CR^8R^9$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O; B=O, E=NR$^{10}$;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups thalt include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=NR$^{10}$, E=NR$^{23}$;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbaiate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=CR$^8$R$^9$, E=NR$^{10}$;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O, B=S, E=NR$^{10}$;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

A=O; B=O, E=O;

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$; B=O, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, almide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or Prodrug is defined as follows:

$A=CR^8R^9$, $B=NR^{10}$, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups thait include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single oir double bond, wherein in the presence of a single bond, the valences are completed with hydrogens.

In another sub-embodiment, a structure of the formula (IV) is given wherein the compound or its phannaceutically acceptable salts or prodrug is defined as follows:

$A=CR^8R^9$, $B=CR^{21}R^{22}$, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, B=S, E=O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, B=O, E=S;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, $B=NR^{10}$, $E=S$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^7R^8$, $B=CR^7R^8$, $E=S$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or Prodrug is defined as follows:

$A=CR^8R^9$, $B=S$, $E=S$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$; $B=O$, $E=CR^{21}R^{22}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, $B=NR^{10}$, $E=CR^{21}R^{22}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, $B=CR^{21}R^{22}$, $E=CR^{24}R^{25}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, B=S, $E=CR^{21}R^{22}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$; B=O, $E=NR^{10}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^7R^8$, $B=NR^{10}$, $E=NR^{23}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}O$ or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, $B=CR^{21}R^{22}$, $E=NR^{10}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}O$ or $CR^{15}R^{16}NR^{17}$;

the dotted line indicates the presence of either a single or double bond, wherein in the presence of a single bond, the valences are completed with hydrogens.

In another sub-embodiment, a structure of the formula (IV) is given wherein the compound or its pharmaceutically acceptable salts or prodrug is defined as follows:

$A=CR^8R^9$, $B=S$, $E=NR^{10}$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}O$ or $CR^{15}R^{16}NR^{17}$;

the dotted line indicates the presence of either a single or double bond, wherein in the presence of a single bond, the valences are completed with hydrogens.

In a particular embodiment of the present invention, the compounds of the formula (IV) are the following species:

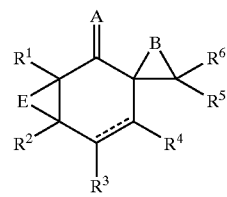

(IV)

| A | B | D | $R^1$ | $R^2$ | $R^3$ | $R^4$ | $R^5$ | $R^6$ |
|---|---|---|---|---|---|---|---|---|
| O | O | O | Me | H | H | H | Me | Me |
| O | O | O | i-Pr | H | H | H | Me | Me |
| O | O | O | Ph | H | H | H | Me | Me |
| O | O | O | Me | Me | H | H | Me | Me |
| O | O | O | i-Pr | Me | H | H | Me | Me |
| O | O | O | Ph | Me | H | H | Me | Me |
| O | O | O | Me | H | Me | H | Me | Me |
| O | O | O | i-Pr | H | Me | H | Me | Me |
| O | O | O | Ph | H | Me | H | Me | Me |
| O | O | O | Me | H | H | Me | Me | Me |
| O | O | O | i-Pr | H | H | Me | Me | Me |
| O | O | O | Ph | H | H | Me | Me | Me |
| O | O | O | Me | H | $CH_2Ph$ | H | Me | Me |
| O | O | O | i-Pr | H | $CH_2Ph$ | H | Me | Me |
| O | O | O | Ph | H | $CH_2Ph$ | H | Me | Me |
| O | $CH_2$ | O | Me | H | H | H | Me | Me |
| O | $CH_2$ | O | i-Pr | H | H | H | Me | Me |
| O | $CH_2$ | O | Ph | H | H | H | Me | Me |
| O | $CH_2$ | O | Me | Me | H | H | Me | Me |
| O | $CH_2$ | O | i-Pr | Me | H | H | Me | Me |
| O | $CH_2$ | O | Ph | Me | H | H | Me | Me |
| O | $CH_2$ | O | Me | H | Me | H | Me | Me |
| O | $CH_2$ | O | i-Pr | H | Me | H | Me | Me |
| O | $CH_2$ | O | Ph | H | Me | H | Me | Me |
| O | $CH_2$ | O | Me | H | H | Me | Me | Me |
| O | $CH_2$ | O | i-Pr | H | H | Me | Me | Me |
| O | $CH_2$ | O | Ph | H | H | Me | Me | Me |
| O | $CH_2$ | O | Me | H | $CH_2Ph$ | H | Me | Me |
| O | $CH_2$ | O | i-Pr | H | $CH_2Ph$ | H | Me | Me |
| O | $CH_2$ | O | Ph | H | $CH_2Ph$ | H | Me | Me |

In a sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}O$ or $CR^{15}R^{16}NR^{17}$;

the dotted line indicates the presence of either a single or double bond, wherein in the presence of a single bond, the valences are completed with hydrogens.

$G=OR^{26}$, $B=O$, $E=O$, and $D=O$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$OR^{26}$, B=$NR^8$, E=O and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$OR^{26}$, B=$CR^8R^9$, E=O and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$OR^{26}$, B=S, E=O and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$OR^{26}$, B=O, E=S, D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=NR^{10}$, $E=S$ and $D=O$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=CR^8R^9$, $E=S$, $D=O$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ and independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=S$, $E=S$, $D=O$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=O$, $E=CR^8R^9$ and $D=O$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or $S$);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=NR^{10}$, $E=CR^8R^9$ and $D=O$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or $S$);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=CR^8R^9$, $E=CR^{21}R^{22}$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, B=S, $E=CR^8R^9$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=NR^{10}$, $E=NW^{23}$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=CR^8R^9$, $E=NR^{10}$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}{=}CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, B=S, $E=NR^{10}$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$; B=O, E=$NR^{10}$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, B=$CR^8R^9$, E=$NR^{10}$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$; B=O, E=O and D=$CR^8R^9$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, B=$NR^{10}$, E=O and D=$CR^8R^9$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=CR^8R^9$, $E=O$, $D=CR^{21}R^{22}$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=S$, $E=O$, and $D=CR^8R^9$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=O$, $E=S$ and $D=CR^8R^9$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=NR^{10}$, $E=S$, $D=CR^8R^9$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=CR^8R^9$, $E=S$, and $D=CR^{21}R^{22}$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, B=S, E=S and $D=CR^8R^9$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$; B=O, $E=CR^8R^9$ and $D=CR^{21}R^{22}$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=NR^{10}$, $E=CR^9R^8$ and $D=CR^{21}R^{22}$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=CR^9R^8$, $E=CR^{21}R^{22}$ and $D=CR^{25}R^{24}$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, B=S, $E=CR^9R^8$ and $D=CR^{12}R^{22}$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$; B=O, $E=NR^{10}$ and $D=CR^9R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=NR^{10}$, $E=NR^{23}$ and $D=CR^9R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, $B=CR^9R^8$, $E=NR^{10}$ and $D=CR^{21}R^{22}$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=OR^{26}$, B=S, $E=NR^{10}$ and $D=CR^9R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{28}R^{19}$, B=O, E=O, D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$, $B=NR^{10}$, E=O and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$, $B=CR^9R^8$, E=O and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$, B=S, E=O and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$; B=O, E=S, D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$, $B=NR^{10}$, E=S and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$, $B=CR^9R^8$, E=S and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$, B=S, E=S and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$; B=O, $E=CR^9R^8$ and D=O.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^{27}R^{28}$, $B=NR^{10}$, $E=CR^9R^8$ and D=O.

In another sub-embodiment, a structure of the formula (V) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);
- $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);
- $R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;
- the dotted line indicates the presence of either a single or double bond, wherein in the presence of a single bond, the valences are completed with hydrogens.
- $G=NR^{27}R^{28}$, $B=CR^9R^8$, $E=CR^{21}R^{22}$ and $D=O$.

In another sub-embodiment, a structure of the formula (V) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);
- $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);
- $R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;
- the dotted line indicates the presence of either a single or double bond, wherein in the presence of a single bond, the valences are completed with hydrogens.
- $G=NR^{27}R^{28}$, $B=S$, $E=CR^9R^8$ and $D=O$.

In another sub-embodiment, a structure of the formula (V) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);
- $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);
- $R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;
- the dotted line indicates the presence of either a single or double, bond, wherein in the presence of a single bond, the valences are completed with hydrogens.
- $G=NR^{27}R^{28}$, $B=O$, $E=NR^{10}$ and $D=O$.

In another sub-embodiment, a structure of the formula (V) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);
- $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);
- $R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;
- the dotted line indicates the presence of either a single or double bond, wherein in the presence of a single bond, the valences are completed with hydrogens.
- $G=NR^{27}R^{28}$, $B=NR^{10}$, $E=NR^{23}$ and $D=O$.

In another sub-embodiment, a structure of the formula (V) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ ($X=O$, $NR^{14}$ or S);
- $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ ($X=O$, $NR^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

G=NR$^{27}$R$^{28}$, B=CR$^9$R, E=NR$^{10}$ and D=O.

In another sub-embodiment, a structure of the formula (V) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

G=NR$^7$R$^8$, B=S, E=NR$^7$ and D=O.

In another sub-embodiment, a structure of the formula (V) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S).

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

G=NR$^7$R$^8$, B=O, E=O and D=CR$^7$R$^8$.

In another sub-embodiment, a structure of the formula (V) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

G=NR$^7$R$^8$, B=NR$^8$, E=O, and D=CR$^7$R$^8$.

In another sub-embodiment, a structure of the formula (V) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^{11}$ (X=O, NR$^{12}$ or S);

R$^1$ and R$^2$, R$^2$ and R$^3$, R$^3$ and R$^4$, R$^4$ and R$^5$ and R$^5$ and R$^6$ can also each be comprised of one or two CR$^{13}$R$^{14}$ groups, connected by a tether, independently selected from CR$^{15}$R$^{16}$, CR$^{15}$R$^{16}$CR$^{17}$R$^{18}$, CR$^{15}$=CR$^{16}$, CR$^{15}$R$^{16}$ O or CR$^{15}$R$^{16}$NR$^{17}$;

the dotted line indicates the presence of either a single or double bond, wherein in the presence of a single bond, the valences are completed with hydrogens.

G=NR$^7$R$^8$, B=CR$^7$R$^8$, E=O, and D=CR$^7$R$^8$.

In another sub-embodiment, a structure of the formula (V) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^{13}$ (X=O, NR$^{14}$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$NR^7R^8$, B=S, E=O and D=$CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$NR^7R^8$, B=O, E=S and D=$CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$NR^7R^8$, B=$NR^8$, E=S and D=$CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$NR^7R^8$, B=$CR^7R^8$, E=S and D=$CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}$=$CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

G=$NR^7R^8$, B=S, E=S and D=$CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^7R^8$, B=O, $E=CR^7R^8$ and $D=CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^7R^8$, $B=NR^8$, $E=CR^7R^8$ and $D=CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^7R$, $B=CR^7R^8$, $E=CR^7R^8$ and $D=CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

$G=NR^7R^8$, B=S, $E=CR^7R^8$ and $D=CR^7R^8$.

In another sub-embodiment, a structure of the formula (V) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

R¹ and R², R² and R³, R³ and R⁴, R⁴ and R⁵ and R⁵ and R⁶ can also each be comprised of one or two CR¹³R¹⁴ groups, connected by a tether, independently selected from CR¹⁵R¹⁶, CR¹⁵R¹⁶CR¹⁷R¹⁸, CR¹⁵=CR¹⁶, CR¹⁵R¹⁶ O or CR¹⁵R¹⁶NR¹⁷;

the dotted line indicates the presence of either a single or double bond, wherein in the presence of a single bond, the valences are completed with hydrogens.

G=NR⁷R⁸, B=O, E=NR⁷ and D=CR⁷R⁸.

In another sub-embodiment, a structure of the formula (V) is given wherein the compound or its pharmaceutically acceptable salts or prodrug is defined as follows:

R¹ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR¹³ (X=O, NR¹⁴ or S);

R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²² and R²³ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR¹¹ (X=O, NR¹² or S);

R¹ and R², R² and R³, R³ and R⁴, R⁴ and R⁵ and R⁵ and R⁶ can also each be comprised of one or two CR¹³R¹⁴ groups, connected by a tether, independently selected from CR¹⁵R¹⁶, CR¹⁵R¹⁶CR¹⁷R¹⁸, CR¹⁵=CR¹⁶, CR¹⁵R¹⁶ O or CR¹⁵R¹⁶NR¹⁷;

the dotted line indicates the presence of either a single or double bond, wherein in the presence of a single bond, the valences are completed with hydrogens.

G=NR⁷R⁸, B=NR⁸, E=NR⁷ and D=CR⁷R⁸.

In another sub-embodiment, a structure of the formula (V) is given wherein the compound or its pharmaceutically acceptable salts or prodrug is defined as follows:

R¹ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR¹³ (X=O, NR¹⁴ or S);

R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²² and R²³ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR¹¹ (X=O, NR¹² or S);

R¹ and R², R² and R³, R³ and R⁴, R⁴ and R⁵ and R⁵ and R⁶ can also each be comprised of one or two CR¹³R¹⁴ groups, connected by a tether, independently selected from CR¹⁵R¹⁶, CR¹⁵R¹⁶CR¹⁷R¹⁸, CR¹⁵=CR¹⁶, CR¹⁵R¹⁶ O or CR¹⁵R¹⁶NR¹⁷;

the dotted line indicates the presence of either a single or double bond, wherein in the presence of a single bond, the valences are completed with hydrogens.

G=NR⁷R⁸, B=CR⁷R⁸, E=NR⁷ and D=CR⁷R⁸.

In another sub-embodiment, a structure of the formula (V) is given wherein the compound or its pharmaceutically acceptable salts or prodrug is defined as follows:

R¹ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR¹³ (X=O, NR¹⁴ or S);

R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²² and R²³ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR¹¹ (X=O, NR¹² or S);

R¹ and R², R² and R³, R³ and R⁴, R⁴ and R⁵ and R⁵ and R⁶ can also each be comprised of one or two CR¹³R¹⁴ groups, connected by a tether, independently selected from CR¹⁵R¹⁶, CR¹⁵R¹⁶CR¹⁷R¹⁸, CR¹⁵=CR¹⁶, CR¹⁵R¹⁶ O or CR¹⁵R¹⁶NR¹⁷;

the dotted line indicates the presence of either a single or double bond, wherein in the presence of a single bond, the valences are completed with hydrogens.

G=NR⁷R⁸, B=S, E=NR⁷ and D=CR⁷R⁸.

In a particular embodiment of the present invention, the compounds of the formula (V) are the following species:

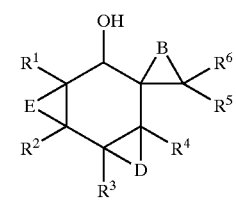

(V)

| B | D | E | R¹ | R² | R³ | R⁴ | R⁵ | R⁶ |
|---|---|---|----|----|----|----|----|----|
| O | O | O | Me | H | H | H | Me | Me |
| O | O | O | i-Pr | H | H | H | Me | Me |
| O | O | O | Ph | H | H | H | Me | Me |
| O | O | O | Me | Me | H | H | Me | Me |
| O | O | O | i-Pr | Me | H | H | Me | Me |
| O | O | O | Ph | Me | H | H | Me | Me |
| O | O | O | Me | H | Me | H | Me | Me |
| O | O | O | i-Pr | H | Me | H | Me | Me |
| O | O | O | Ph | H | Me | H | Me | Me |
| O | O | O | Me | H | H | Me | Me | Me |
| O | O | O | i-Pr | H | H | Me | Me | Me |
| O | O | O | Ph | H | H | Me | Me | Me |
| O | O | O | Me | H | CH₂Ph | H | Me | Me |
| O | O | O | i-Pr | H | CH₂Ph | H | Me | Me |
| O | O | O | Ph | H | CH₂Ph | H | Me | Me |
| CH₂ | O | O | Me | H | H | H | Me | Me |
| CH₂ | O | O | i-Pr | H | H | H | Me | Me |
| CH₂ | O | O | Ph | H | H | H | Me | Me |
| CH₂ | O | O | Me | Me | H | H | Me | Me |
| CH₂ | O | O | i-Pr | Me | H | H | Me | Me |
| CH₂ | O | O | Ph | Me | H | H | Me | Me |
| CH₂ | O | O | Me | H | Me | H | Me | Me |
| CH₂ | O | O | i-Pr | H | Me | H | Me | Me |
| CH₂ | O | O | Ph | H | Me | H | Me | Me |
| CH₂ | O | O | Me | H | H | Me | Me | Me |
| CH₂ | O | O | i-Pr | H | H | Me | Me | Me |
| CH₂ | O | O | Ph | H | H | Me | Me | Me |

-continued

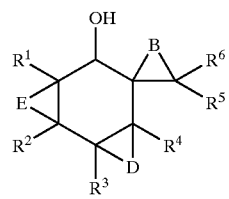

(V)

| B | D | E | $R^1$ | $R^2$ | $R^3$ | $R^4$ | $R^5$ | $R^6$ |
|---|---|---|---|---|---|---|---|---|
| CH$_2$ | O | O | Me | H | CH$_2$Ph | H | Me | Me |
| CH$_2$ | O | O | i-Pr | H | CH$_2$Ph | H | Me | Me |
| CH$_2$ | O | O | Ph | H | CH$_2$Ph | H | Me | Me |
| CH$_2$ | CH$_2$ | O | Ph | H | CH$_2$Ph | H | Me | Me |
| CH$_2$ | CH$_2$ | O | Me | H | H | H | Me | Me |
| CH$_2$ | CH$_2$ | O | i-Pr | H | H | H | Me | Me |
| CH$_2$ | CH$_2$ | O | Ph | H | H | H | Me | Me |
| CH$_2$ | CH$_2$ | O | Me | Me | H | H | Me | Me |
| CH$_2$ | CH$_2$ | O | i-Pr | Me | H | H | Me | Me |
| CH$_2$ | CH$_2$ | O | Ph | Me | H | H | Me | Me |
| CH$_2$ | CH$_2$ | O | Me | H | Me | H | Me | Me |
| CH$_2$ | CH$_2$ | O | i-Pr | H | Me | H | Me | Me |
| CH$_2$ | CH$_2$ | O | Ph | H | Me | H | Me | Me |
| CH$_2$ | CH$_2$ | O | Me | H | H | Me | Me | Me |
| CH$_2$ | CH$_2$ | O | i-Pr | H | H | Me | Me | Me |
| CH$_2$ | CH$_2$ | O | Ph | H | H | Me | Me | Me |
| CH$_2$ | CH$_2$ | O | Me | H | CH$_2$Ph | H | Me | Me |
| CH$_2$ | CH$_2$ | O | i-Pr | H | CH$_2$Ph | H | Me | Me |
| CH$_2$ | CH$_2$ | O | Ph | H | CH$_2$Ph | H | Me | Me |
| CH$_2$ | CH$_2$ | O | Ph | H | CH$_2$Ph | H | Me | Me |
| CH$_2$ | O | CH$_2$ | Me | H | H | H | Me | Me |
| CH$_2$ | O | CH$_2$ | i-Pr | H | H | H | Me | Me |
| CH$_2$ | O | CH$_2$ | Ph | H | H | H | Me | Me |
| CH$_2$ | O | CH$_2$ | Me | Me | H | H | Me | Me |
| CH$_2$ | O | CH$_2$ | i-Pr | Me | H | H | Me | Me |
| CH$_2$ | O | CH$_2$ | Ph | Me | H | H | Me | Me |
| CH$_2$ | O | CH$_2$ | Me | H | Me | H | Me | Me |
| CH$_2$ | O | CH$_2$ | i-Pr | H | Me | H | Me | Me |
| CH$_2$ | O | CH$_2$ | Ph | H | Me | H | Me | Me |
| CH$_2$ | O | CH$_2$ | Me | H | H | Me | Me | Me |
| CH$_2$ | O | CH$_2$ | i-Pr | H | H | Me | Me | Me |
| CH$_2$ | O | CH$_2$ | Ph | H | H | Me | Me | Me |
| CH$_2$ | O | CH$_2$ | Me | H | CH$_2$Ph | H | Me | Me |
| CH$_2$ | O | CH$_2$ | i-Pr | H | CH$_2$Ph | H | Me | Me |
| CH$_2$ | O | CH$_2$ | Ph | H | CH$_2$Ph | H | Me | Me |

In a sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

The dotted line indicates the presence of either a single or double bond;

B is selected from the groups that include $CR^7R^8$, O, S or $NR^7$;

G is selected from the groups that include $OR^7$, $NR^7R^8$ or $SR^7$.

In another sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$; and The dotted line indicates the presence of either a single or double bond;

B is O;

G is $OR^7$.

In another sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

The dotted line indicates the presence of either a single or double bond;

B is O;

G is $NR^7R^8$.

In another sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and The dotted line indicates the presence of either a single or double bond;

B is O;

is G is $SR^7$.

In another sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$.

The dotted line indicates the presence of either a single or double bond;

B is $CR^7R^8$;

G $OR^7$.

In another sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and The dotted line indicates the presence of either a single or double bond;

B is $CR^7R^8$;

G is $NR^7R^8$.

In another sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

B is $CR^7R^8$;

G is $SR^7$.

In another sub-embodiment, a structure of the formula (VI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R^4$, $R^4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR^8$, $CR_7R_8O$ and $CR_7R_8NR_7$;

The dotted line indicates the presence of either a single or double bond;

B is S;

G is $OR^7$.

In another sub-embodiment, a structure of the formula (VI) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamoyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

B is S;

G is NR$^7$R$^8$.

In another sub-embodiment, a structure of the formula (VI) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamoyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

B is S;

G is SR$^7$.

In another sub-embodiment, a structure of the formula (VI) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamoyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$; and The dotted line indicates the presence of either a single or double bond;

B is NR$^7$;

G is OR$^7$.

In another sub-embodiment, a structure of the formula (VI) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamoyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

B is NR$^7$;

G is NR$^7$R$^8$.

In another sub-embodiment, a structure of the formula (VI) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamoyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

B is $NR^7$;
G is $SR^7$.

In a particular embodiment of the present invention, the compounds of the formula (VI) are the following species:

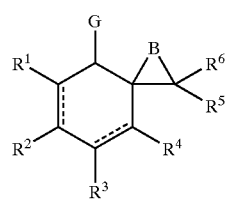

(VI)

| G | B | $R^1$ | $R^2$ | $R^3$ | $R^4$ | $R^5$ | $R^6$ |
|---|---|---|---|---|---|---|---|
| OH | O | Me | H | H | H | Me | Me |
| OH | O | i-Pr | H | H | H | Me | Me |
| OH | O | Ph | H | H | H | Me | Me |
| OH | O | Me | Me | H | H | Me | Me |
| OH | O | i-Pr | Me | H | H | Me | Me |
| OH | O | Ph | Me | H | H | Me | Me |
| OH | O | Me | H | Me | H | Me | Me |
| OH | O | i-Pr | H | Me | H | Me | Me |
| OH | O | Ph | H | Me | H | Me | Me |
| OH | O | Me | H | H | Me | Me | Me |
| OH | O | i-Pr | H | H | Me | Me | Me |
| OH | O | Ph | H | H | Me | Me | Me |
| OH | O | Me | H | $CH_2Ph$ | H | Me | Me |
| OH | O | i-Pr | H | $CH_2Ph$ | H | Me | Me |
| OH | O | Ph | H | $CH_2Ph$ | H | Me | Me |
| OH | $CH_2$ | Me | H | H | H | Me | Me |
| OH | $CH_2$ | i-Pr | H | H | H | Me | Me |
| OH | $CH_2$ | Ph | H | H | H | Me | Me |
| OH | $CH_2$ | Me | Me | H | H | Me | Me |
| OH | $CH_2$ | i-Pr | Me | H | H | Me | Me |
| OH | $CH_2$ | Ph | Me | H | H | Me | Me |
| OH | $CH_2$ | Me | H | Me | H | Me | Me |
| OH | $CH_2$ | i-Pr | H | Me | H | Me | Me |
| OH | $CH_2$ | Ph | H | Me | H | Me | Me |
| OH | $CH_2$ | Me | H | H | Me | Me | Me |
| OH | $CH_2$ | i-Pr | H | H | Me | Me | Me |
| OH | $CH_2$ | Ph | H | H | Me | Me | Me |
| OH | $CH_2$ | Me | H | $CH_2Ph$ | H | Me | Me |
| OH | $CH_2$ | i-Pr | H | $CH_2Ph$ | H | Me | Me |
| OH | $CH_2$ | Ph | H | $CH_2Ph$ | H | Me | Me |

In a sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7$=$CR_8$, $CR_7R_8O$ and $CR_7R_8NR_7$.

The dotted line indicates the presence of either a single or double bond;

B is selected from the groups that include $CR^7R^8$, O, S or $NR^7$;

A is selected from the groups that include O, $NR^7$ or S.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7$=$CR_8$, $CR_7R_8O$ and $CR_7R_8NR_7$; and The dotted line indicates the presence of either a single or double bond;

B is O;

A is O.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7$=$CR_8$, $CR_7R_8O$ and $CR_7R_8NR_7$.

The dotted line indicates the presence of either a single or double bond;

B is O;

A is $NR^7$.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$; and The dotted line indicates the presence of either a single or double bond;

B is O;

A is S.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$.

The dotted line indicates the presence of either a single or double bond;

B is $CR^7R^8$;

A is O.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$; and The dotted line indicates the presence of either a single or double bond;

B is $CR^7R^8$;

A is $NR^7$.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

The dotted line indicates the presence of either a single or double bond;

B is $CR^7R^8$;

A is S.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$;

The dotted line indicates the presence of either a single or double bond;

B is S;

A is O.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

B is S;

A is $NR^7$.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

B is S;

A is S.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

B is $NR^7$;

A is O.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

B is $NR^7$;

A is $NR^7$.

In another sub-embodiment, a structure of the formula (VII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

B is $NR^7$;

A is S.

In a particular embodiment of the present invention, the compounds of the formula (VII) are the following species:

(VII)

[Structure shown: cyclohexene ring with substituents R¹ (on carbon bearing =A), R² (vinyl position), R³ (vinyl position), R⁴, and a spiro cyclopropane (B) with R⁵ and R⁶]

| A | B | R¹ | R² | R³ | R⁴ | R⁵ | R⁶ |
|---|---|---|---|---|---|---|---|
| O | O | Me | H | H | H | Me | Me |
| O | O | i-Pr | H | H | H | Me | Me |
| O | O | Ph | H | H | H | Me | Me |
| O | O | Me | Me | H | H | Me | Me |
| O | O | i-Pr | Me | H | H | Me | Me |
| O | O | Ph | Me | H | H | Me | Me |
| O | O | Me | H | Me | H | Me | Me |
| O | O | i-Pr | H | Me | H | Me | Me |
| O | O | Ph | H | Me | H | Me | Me |
| O | O | Me | H | H | Me | Me | Me |
| O | O | i-Pr | H | H | Me | Me | Me |
| O | O | Ph | H | H | Me | Me | Me |
| O | O | Me | H | CH₂Ph | H | Me | Me |
| O | O | i-Pr | H | CH₂Ph | H | Me | Me |
| O | O | Ph | H | CH₂Ph | H | Me | Me |
| O | CH₂ | Me | H | H | H | Me | Me |
| O | CH₂ | i-Pr | H | H | H | Me | Me |
| O | CH₂ | Ph | H | H | H | Me | Me |
| O | CH₂ | Me | Me | H | H | Me | Me |
| O | CH₂ | i-Pr | Me | H | H | Me | Me |
| O | CH₂ | Ph | Me | H | H | Me | Me |
| O | CH₂ | Me | H | Me | H | Me | Me |
| O | CH₂ | i-Pr | H | Me | H | Me | Me |
| O | CH₂ | Ph | H | Me | H | Me | Me |
| O | CH₂ | Me | H | H | Me | Me | Me |
| O | CH₂ | i-Pr | H | H | Me | Me | Me |
| O | CH₂ | Ph | H | H | Me | Me | Me |
| O | CH₂ | Me | H | CH₂Ph | H | Me | Me |
| O | CH₂ | i-Pr | H | CH₂Ph | H | Me | Me |
| O | CH₂ | Ph | H | CH₂Ph | H | Me | Me |

In a sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

E and B are selected from the groups that include $CR^7R^8$, O, S or $NR^7$;

G is selected from the groups that include $OR^7$, $NR^7R^8$ or $SR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$; and B=O, E=O and G=$OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

B=O, E=$NR^8$ and G=$OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$; and B=O, E=$CR^7R^8$, and G=$OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$.

B=O, E=S and G=$OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR_7R^8$, $CR^7{=}CR^8$, $CR^7R^8O$ and $CR^7R^8NR^7$; and B=O, E=O and G=$NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

B=O, E=$NR^8$ and G=$NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$;

B=O, E=$CR^7R^8$ and G=$NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$;

B=O, E=S and G=$NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$; and $B=CR^7R^8$, $E=O$ and $G=OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$B=CR^7R^8$, $E=NR^8$ and $G=OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$B=CR^7R^8$, $E=CR^7R^8$ and $G=OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$B=CR^7R^8$, $E=S$. and $G=OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$B=CR^7R^8$, $E=O$ and $G=NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$B=CR^7R^8$, $E=NR^8$ and $G=NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$B=CR^7R^8$, $E=CR^7R^8$ and $G=NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$B=CR^7R^8$, E=S and $G=NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=S, E=O and $G=OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=S, $E=NR^8$ and $G=OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=S, $E=C^7R^8$ and $G=OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=S, E=S. and $G=OR^7$.

In another sub-embodiment, a structure of the formula (VIII) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

B=S, E=O and G=NR$^7$R$^8$.

In another sub-embodiment, a structure of the formula (VIII) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

B=S, E=NR$^8$ and G=NR$^7$R$^8$.

In another sub-embodiment, a structure of the formula (VIII) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

B=S, E=CR$^7$R$^8$ and G=NR$^7$R$^8$.

In another sub-embodiment, a structure of the formula (VIII) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

B=S, E=S and G=NR$^7$R$^8$.

In another sub-embodiment, a structure of the formula (VIII) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

B=NR$^7$, E=O and G=OR$^7$.

In another sub-embodiment, a structure of the formula (VIII) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=$NR^7$, E=$NR^8$ and G=$OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=$NR^7$, E=$CR^7R^8$ and G=$OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=$NR^7$, E=S. and G=$OR^7$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=$NR^7$, E=O and G=$NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=$NR^7$, E=$NR^8$ and G=$NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B=$NR^7$, E=$CR^7R^8$ and G=$NR^7R^8$.

In another sub-embodiment, a structure of the formula (VIII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$B=NR^7$, $E=S$ and $G=NR^7R^8$.

In a particular embodiment of the present invention, the compounds of the formula (VIII) are the following species:

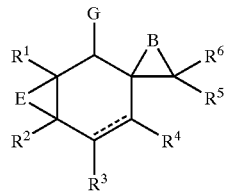

(VIII)

| G | B | E | $R^1$ | $R^2$ | $R^3$ | $R^4$ | $R^5$ | $R^6$ |
|---|---|---|-------|-------|-------|-------|-------|-------|
| OH | O | O | Me | H | H | H | Me | Me |
| OH | O | O | i-Pr | H | H | H | Me | Me |
| OH | O | O | Ph | H | H | H | Me | Me |
| OH | O | O | Me | Me | H | H | Me | Me |
| OH | O | O | i-Pr | Me | H | H | Me | Me |
| OH | O | O | Ph | Me | H | H | Me | Me |
| OH | O | O | Me | H | Me | H | Me | Me |
| OH | O | O | i-Pr | H | Me | H | Me | Me |
| OH | O | O | Ph | H | Me | H | Me | Me |
| OH | O | O | Me | H | H | Me | Me | Me |
| OH | O | O | i-Pr | H | H | Me | Me | Me |
| OH | O | O | Ph | H | H | Me | Me | Me |
| OH | O | O | Me | H | $CH_2Ph$ | H | Me | Me |
| OH | O | O | i-Pr | H | $CH_2Ph$ | H | Me | Me |
| OH | O | O | Ph | H | $CH_2Ph$ | H | Me | Me |
| OH | $CH_2$ | O | Me | H | H | H | Me | Me |
| OH | $CH_2$ | O | i-Pr | H | H | H | Me | Me |
| OH | $CH_2$ | O | Ph | H | H | H | Me | Me |
| OH | $CH_2$ | O | Me | Me | H | H | Me | Me |
| OH | $CH_2$ | O | i-Pr | Me | H | H | Me | Me |
| OH | $CH_2$ | O | Ph | Me | H | H | Me | Me |
| OH | $CH_2$ | O | Me | H | Me | H | Me | Me |
| OH | $CH_2$ | O | i-Pr | H | Me | H | Me | Me |
| OH | $CH_2$ | O | Ph | H | Me | H | Me | Me |
| OH | $CH_2$ | O | Me | H | H | Me | Me | Me |
| OH | $CH_2$ | O | i-Pr | H | H | Me | Me | Me |
| OH | $CH_2$ | O | Ph | H | H | Me | Me | Me |
| OH | $CH_2$ | O | Me | H | $CH_2Ph$ | H | Me | Me |
| OH | $CH_2$ | O | i-Pr | H | $CH_2Ph$ | H | Me | Me |
| OH | $CH_2$ | O | Ph | H | $CH_2Ph$ | H | Me | Me |
| OH | O | $CH_2$ | Me | H | H | H | Me | Me |
| OH | O | $CH_2$ | i-Pr | H | H | H | Me | Me |
| OH | O | $CH_2$ | Ph | H | H | H | Me | Me |
| OH | O | $CH_2$ | Me | Me | H | H | Me | Me |
| OH | O | $CH_2$ | i-Pr | Me | H | H | Me | Me |
| OH | O | $CH_2$ | Ph | Me | H | H | Me | Me |
| OH | O | $CH_2$ | Me | H | Me | H | Me | Me |
| OH | O | $CH_2$ | i-Pr | H | Me | H | Me | Me |
| OH | O | $CH_2$ | Ph | H | Me | H | Me | Me |
| OH | O | $CH_2$ | Me | H | H | Me | Me | Me |
| OH | O | $CH_2$ | i-Pr | H | H | Me | Me | Me |
| OH | O | $CH_2$ | Ph | H | H | Me | Me | Me |
| OH | O | $CH_2$ | Me | H | $CH_2Ph$ | H | Me | Me |
| OH | O | $CH_2$ | i-Pr | H | $CH_2Ph$ | H | Me | Me |
| OH | O | $CH_2$ | Ph | H | $CH_2Ph$ | H | Me | Me |

In a sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

The dotted line indicates the presence of either a single or double bond;

E is selected from the groups that include $CR^7R^8$, O, S or $NR^7$;

G is selected from the groups that include $OR^7$, $NR^7R^8$ or $SR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$; and The dotted line indicates the presence of either a single or double bond;

E is O;

G is $OR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

The dotted line indicates the presence of either a single or double bond;

E is O;

G is $NR^7R^8$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and The dotted line indicates the presence of either a single or double bond;

E is O;

G is $SR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$.

The dotted line indicates the presence of either a single or double bond;

E is $CR^7R^8$;

G $OR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and The dotted line indicates the presence of either a single or double bond;

E is $CR^7R^8$;

G is $NR^7R^8$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $CR^7R^8$;

G is $SR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

The dotted line indicates the presence of either a single or double bond;

E is S;

G is $OR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is S;

G is $NR^7R^8$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is S;

G is $SR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $NR^7$;

G is $OR^7$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $NR^7$;

G is $NR^7R^8$.

In another sub-embodiment, a structure of the formula (IX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $NR^7$;

G is $SR^7$.

In a particular embodiment of the present invention, the compounds of the formula (IX) are the following species:

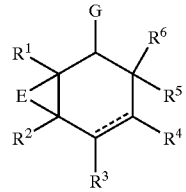

(IX)

| G | E | $R^1$ | $R^2$ | $R^3$ | $R^4$ | $R^5$ | $R^6$ |
|---|---|---|---|---|---|---|---|
| OH | O | Me | H | H | H | Me | Me |
| OH | O | i-Pr | H | H | H | Me | Me |
| OH | O | Ph | H | H | H | Me | Me |
| OH | O | Me | Me | H | H | Me | Me |
| OH | O | i-Pr | Me | H | H | Me | Me |
| OH | O | Ph | Me | H | H | Me | Me |
| OH | O | Me | H | Me | H | Me | Me |
| OH | O | i-Pr | H | Me | H | Me | Me |
| OH | O | Ph | H | Me | H | Me | Me |
| OH | O | Me | H | H | Me | Me | Me |
| OH | O | i-Pr | H | H | Me | Me | Me |
| OH | O | Ph | H | H | Me | Me | Me |
| OH | O | Me | H | $CH_2Ph$ | H | Me | Me |
| OH | O | i-Pr | H | $CH_2Ph$ | H | Me | Me |
| OH | O | Ph | H | $CH_2Ph$ | H | Me | Me |
| OH | $CH_2$ | Me | H | H | H | Me | Me |
| OH | $CH_2$ | i-Pr | H | H | H | Me | Me |
| OH | $CH_2$ | Ph | H | H | H | Me | Me |
| OH | $CH_2$ | Me | Me | H | H | Me | Me |
| OH | $CH_2$ | i-Pr | Me | H | H | Me | Me |
| OH | $CH_2$ | Ph | Me | H | H | Me | Me |
| OH | $CH_2$ | Me | H | Me | H | Me | Me |
| OH | $CH_2$ | i-Pr | H | Me | H | Me | Me |
| OH | $CH_2$ | Ph | H | Me | H | Me | Me |
| OH | $CH_2$ | Me | H | H | Me | Me | Me |
| OH | $CH_2$ | i-Pr | H | H | Me | Me | Me |
| OH | $CH_2$ | Ph | H | H | Me | Me | Me |
| OH | $CH_2$ | Me | H | $CH_2Ph$ | H | Me | Me |
| OH | $CH_2$ | i-Pr | H | $CH_2Ph$ | H | Me | Me |
| OH | $CH_2$ | Ph | H | $CH_2Ph$ | H | Me | Me |

In a sub-embodiment, a structure of the formula (X) is given wherein the compound or its pharmaceutically acceptable salts or prodrug is defined as follows:

A is O;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (X) is given wherein the compound or its pharmaceutically acceptable salts or prodrug is defined as follows:

A is $NR^7$;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S);

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^5=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens.

In another sub-embodiment, a structure of the formula (X) is given wherein the compound or its pharmaceutically acceptable salts or prodrug is defined as follows:

A is S;

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^{13}$ (X=O, $NR^{14}$ or S);

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently are selected from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^{11}$ (X=O, $NR^{12}$ or S)

$R^1$ and $R^2$, $R^2$ and $R^3$, $R^3$ and $R^4$, $R^4$ and $R^5$ and $R^5$ and $R^6$ can also each be comprised of one or two $CR^{13}R^{14}$ groups, connected by a tether, independently selected from $CR^{15}R^{16}$, $CR^{15}R^{16}CR^{17}R^{18}$, $CR^{15}=CR^{16}$, $CR^{15}R^{16}$ O or $CR^{15}R^{16}NR^{17}$;

the dotted line indicates the presence of either a single or double bond, wherein in the presence of a single bond, the valences are completed with hydrogens, In a sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$, and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

The dotted line indicates the presence of either a single or double bond;

E is selected from the groups that include $CR^7R^8$, O, S or $NR^7$;

A is selected from the groups that include O, $NR^7$ or S.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$; and The dotted line indicates the presence of either a single or double bond;

E is O;

A is O.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

The dotted line indicates the presence of either a single or double bond;

E is O;

A is $NR^7$.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and The dotted line indicates the presence of either a single or double bond;

E is O;

A is S.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2, R^3, R^4, R^5, R^6, R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$($X=O$, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$.

The dotted line indicates the presence of either a single or double bond;

E is $CR^7R^8$;

A is O.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and The dotted line indicates the presence of either a single or double bond;

E is $CR^7R^8$;

A is $NR^7$.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $CR^7R^8$;

A is S.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R^6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

The dotted line indicates the presence of either a single or double bond;

E is S;

A is O.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is S;

A is $NR^7$.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is S;

A is S.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $NR^7$;

A is O.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R^1$ and $R^2$, $R^2$ and $R^3$, $R^3$ and $R^4$, $R^4$ and $R^4$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $NR^7$;

A is $NR^8$.

In another sub-embodiment, a structure of the formula (XI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

The dotted line indicates the presence of either a single or double bond;

E is $NR^7$;

A is S.

In a particular embodiment of the present invention, the compounds of the formula (XI) are the following species:

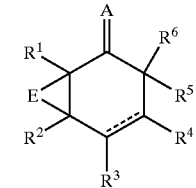

(XI)

| A | E | $R^1$ | $R^2$ | $R^3$ | $R^4$ | $R^5$ | $R^6$ |
|---|---|---|---|---|---|---|---|
| O | O | Me | H | H | H | Me | Me |
| O | O | i-Pr | H | H | H | Me | Me |
| O | O | Ph | H | H | H | Me | Me |
| O | O | Me | Me | H | H | Me | Me |
| O | O | i-Pr | Me | H | H | Me | Me |
| O | O | Ph | Me | H | H | Me | Me |
| O | O | Me | H | Me | H | Me | Me |
| O | O | i-Pr | H | Me | H | Me | Me |
| O | O | Ph | H | Me | H | Me | Me |
| O | O | Me | H | H | Me | Me | Me |
| O | O | i-Pr | H | H | Me | Me | Me |
| O | O | Ph | H | H | Me | Me | Me |
| O | O | Me | H | $CH_2Ph$ | H | Me | Me |
| O | O | i-Pr | H | $CH_2Ph$ | H | Me | Me |
| O | O | Ph | H | $CH_2Ph$ | H | Me | Me |
| O | $CH_2$ | Me | H | H | H | Me | Me |
| O | $CH_2$ | i-Pr | H | H | H | Me | Me |
| O | $CH_2$ | Ph | H | H | H | Me | Me |
| O | $CH_2$ | Me | Me | H | H | Me | Me |
| O | $CH_2$ | i-Pr | Me | H | H | Me | Me |
| O | $CH_2$ | Ph | Me | H | H | Me | Me |
| O | $CH_2$ | Me | H | Me | H | Me | Me |
| O | $CH_2$ | i-Pr | H | Me | H | Me | Me |
| O | $CH_2$ | Ph | H | Me | H | Me | Me |
| O | $CH_2$ | Me | H | H | Me | Me | Me |
| O | $CH_2$ | i-Pr | H | H | Me | Me | Me |
| O | $CH_2$ | Ph | H | H | Me | Me | Me |
| O | $CH_2$ | Me | H | $CH_2Ph$ | H | Me | Me |
| O | $CH_2$ | i-Pr | H | $CH_2Ph$ | H | Me | Me |
| O | $CH_2$ | Ph | H | $CH_2Ph$ | H | Me | Me |

In a sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

E and D are selected from the groups that include $CR^7R^8$, O, S or $NR^7$;

A is selected from the groups that include O, $NR^7$ or S.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$; and D=O, E=O and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

D=O, E=$NR^8$ and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$; and D=O, E=$CR^7R^8$, and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2$, $R^3$, $R^4$, $R^5$, $R^6$, $R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8N^7$.

D=O, E=S and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR_7R^8$, $CR^7=CR^8$, $CR^7R^8O$ and $CR^7R^8NR^7$; and D=O, E=O and A=$NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=O, E=$NR^8$ and A=$NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

D=O, E=$CR^7R^8$ and A=$NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

D=O, E=S and A=$NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=$CR^7R^8$, E=O and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=$CR^7R^8$, E=$NR^8$ and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=CR^7R^8$, $E=CR^7R^8$ and $A=O$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=CR^7R^8$, $E=S$. and $A=O$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^3$, $CR^7R^8O$ and $CR^7R^8NR^7$;

$D=CR^7R^8$, $E=O$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=CR^7R^8$, $E=NR^8$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=CR^7R^8$, $E=CR^7R^8$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=CR^7R^8$, $E=S$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=S, E=O and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=S, E=$NR^8$ and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=S, E=$CR^7R^8$ and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=S, E=S. and A=O.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=S, E=O and A=$NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

D=S, E=$NR^8$ and A=$NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^3NR^7$;

$D=S$, $E=CR^7R^8$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7(X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=S$, $E=S$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R_3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=O$ and $A=O$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=NR^8$ and $A=O$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=CR^7R^8$ and $A=O$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=S$. and $A=O$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=O$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=NR^8$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=CR^7R^8$ and $A=NR^7$.

In another sub-embodiment, a structure of the formula (XII) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$D=NR^7$, $E=S$ and $A=NR^7$.

In a particular embodiment of the present invention, the compounds of the formula (XII) are the following species:

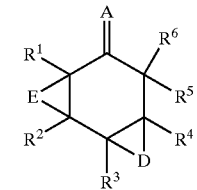

(XII)

| A | D | E | $R^1$ | $R^2$ | $R^3$ | $R^4$ | $R^5$ | $R^6$ |
|---|---|---|---|---|---|---|---|---|
| O | O | O | Me | H | H | H | Me | Me |
| O | O | O | i-Pr | H | H | H | Me | Me |
| O | O | O | Ph | H | H | H | Me | Me |
| O | O | O | Me | Me | H | H | Me | Me |
| O | O | O | i-Pr | Me | H | H | Me | Me |
| O | O | O | Ph | Me | H | H | Me | Me |
| O | O | O | Me | H | Me | H | Me | Me |
| O | O | O | i-Pr | H | Me | H | Me | Me |
| O | O | O | Ph | H | Me | H | Me | Me |
| O | O | O | Me | H | H | Me | Me | Me |
| O | O | O | i-Pr | H | H | Me | Me | Me |
| O | O | O | Ph | H | H | Me | Me | Me |
| O | O | O | Me | H | $CH_2Ph$ | H | Me | Me |
| O | O | O | i-Pr | H | $CH_2Ph$ | H | Me | Me |
| O | O | O | Ph | H | $CH_2Ph$ | H | Me | Me |
| O | O | $CH_2$ | Me | H | H | H | Me | Me |
| O | O | $CH_2$ | i-Pr | H | H | H | Me | Me |
| O | O | $CH_2$ | Ph | H | H | H | Me | Me |

-continued (XII)

$$\text{(structure with ring: A at top, R}^6\text{, R}^1\text{, E, R}^5\text{, R}^2\text{, R}^4\text{, D, R}^3\text{)}$$

| A | D | E | R¹ | R² | R³ | R⁴ | R⁵ | R⁶ |
|---|---|---|----|----|----|----|----|----|
| O | O | CH₂ | Me | Me | H | H | Me | Me |
| O | O | CH₂ | i-Pr | Me | H | H | Me | Me |
| O | O | CH₂ | Ph | Me | H | H | Me | Me |
| O | O | CH₂ | Me | H | Me | H | Me | Me |
| O | O | CH₂ | i-Pr | H | Me | H | Me | Me |
| O | O | CH₂ | Ph | H | Me | H | Me | Me |
| O | O | CH₂ | Me | H | H | Me | Me | Me |
| O | O | CH₂ | i-Pr | H | H | Me | Me | Me |
| O | O | CH₂ | Ph | H | H | Me | Me | Me |
| O | O | CH₂ | Me | H | CH₂Ph | H | Me | Me |
| O | O | CH₂ | i-Pr | H | CH₂Ph | H | Me | Me |
| O | O | CH₂ | Ph | H | CH₂Ph | H | Me | Me |
| O | CH₂ | CH₂ | Me | H | H | H | Me | Me |
| O | CH₂ | CH₂ | i-Pr | H | H | H | Me | Me |
| O | CH₂ | CH₂ | Ph | H | H | H | Me | Me |
| O | CH₂ | CH₂ | Me | Me | H | H | Me | Me |
| O | CH₂ | CH₂ | i-Pr | Me | H | H | Me | Me |
| O | CH₂ | CH₂ | Ph | Me | H | H | Me | Me |
| O | CH₂ | CH₂ | Me | H | Me | H | Me | Me |
| O | CH₂ | CH₂ | i-Pr | H | Me | H | Me | Me |
| O | CH₂ | CH₂ | Ph | H | Me | H | Me | Me |
| O | CH₂ | CH₂ | Me | H | H | Me | Me | Me |
| O | CH₂ | CH₂ | i-Pr | H | H | Me | Me | Me |
| O | CH₂ | CH₂ | Ph | H | H | Me | Me | Me |
| O | CH₂ | CH₂ | Me | H | CH₂Ph | H | Me | Me |
| O | CH₂ | CH₂ | i-Pr | H | CH₂Ph | H | Me | Me |
| O | CH₂ | CH₂ | Ph | H | CH₂Ph | H | Me | Me |

In a sub-embodiment, a structure of the formula (XIII) is given wherein the compound or its pharmaceutically acceptable salts or prodrug is defined as follows:

$R^1$ selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

The dotted line indicates the presence of either a single or double bond;

D is selected from the groups that include $CR^7R^8$, O, S or $NR^7$;

A is selected from the groups that include O, $NR^7$ or S.

In another sub-embodiment, a structure of the formula (XIII) is given wherein the compound or its pharmaceutically acceptable salts or prodrug is defined as follows:

$R_1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$; and The dotted line indicates the presence of either a single or double bond;

D is O;

A is O.

In another sub-embodiment, a structure of the formula (XIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

The dotted line indicates the presence of either a single or double bond;

D is O;

A is $NR^7$.

In another sub-embodiment, a structure of the formula (XIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$; and The dotted line indicates the presence of either a single or double bond;

D is O;

A is S.

In another sub-embodiment, a structure of the formula (XIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, by alkcarbonyl, carbonyl, halide, a residue of a natural or synthetic amino acid, or carbohydrate or $XR^7$ (X=O, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$.

The dotted line indicates the presence of either a single or double bond;

D is $CR^7R^8$;

A O.

In another sub-embodiment, a structure of the formula (XIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR_7R^8$, $CR^7{=}CR^8$, $CR^7R^8O$ and $CR^7R^8NR^7$; and The dotted line indicates the presence of either a single or double bond;

D is $CR^7R^8$;

A is $NR^7$.

In another sub-embodiment, a structure of the formula (XIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

The dotted line indicates the presence of either a single or double bond;

D is $CR^7R^8$;

A is S.

In another sub-embodiment, a structure of the formula (XIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$;

The dotted line indicates the presence of either a single or double bond;

D is S;

A is O.

In another sub-embodiment, a structure of the formula (XIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

D is S;

A is NR$^7$.

In another sub-embodiment, a structure of the formula (XIII) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

D is S;

A is S.

In another sub-embodiment, a structure of the formula (XIII) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

D is NR$^7$;

A is O.

In another sub-embodiment, a structure of the formula (XIII) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^5$, CR$^7$R$^8$O and CR$^7$R$^8$NR$^7$;

The dotted line indicates the presence of either a single or double bond;

D is NR$^7$;

A is NR$^8$.

In another sub-embodiment, a structure of the formula (XIII) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be one or two CR$^7$R$^8$ groups, connected by a tether, selected from groups that include CR$^7$R$^8$, CR$^7$R$^8$CR$^7$R$^8$, CR$^7$=CR$^8$, CR$^7$R$^8$O and CR$^7$R$^8$NR$^7$;

The dotted line indicates the presence of either a single or double bond;

D is NR$^7$;

A is S.

In a particular embodiment of the present invention, the compounds of the formula (XIII) are the following species:

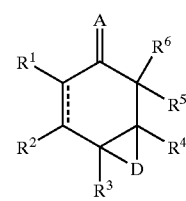

(XIII)

| A | D | R$^1$ | R$^2$ | R$^3$ | R$^4$ | R$^5$ | R$^6$ |
|---|---|---|---|---|---|---|---|
| O | O | Me | H | H | H | Me | Me |
| O | O | i-Pr | H | H | H | Me | Me |
| O | O | Ph | H | H | H | Me | Me |

-continued

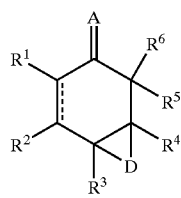

(XIII)

| A | D | $R^1$ | $R^2$ | $R^3$ | $R^4$ | $R^5$ | $R^6$ |
|---|---|---|---|---|---|---|---|
| O | O | Me | Me | H | H | Me | Me |
| O | O | i-Pr | Me | H | H | Me | Me |
| O | O | Ph | Me | H | H | Me | Me |
| O | O | Me | H | Me | H | Me | Me |
| O | O | i-Pr | H | Me | H | Me | Me |
| O | O | Ph | H | Me | H | Me | Me |
| O | O | Me | H | H | Me | Me | Me |
| O | O | i-Pr | H | H | Me | Me | Me |
| O | O | Ph | H | H | Me | Me | Me |
| O | O | Me | H | $CH_2Ph$ | H | Me | Me |
| O | O | i-Pr | H | $CH_2Ph$ | H | Me | Me |
| O | O | Ph | H | $CH_2Ph$ | H | Me | Me |
| O | $CH_2$ | Me | H | H | H | Me | Me |
| O | $CH_2$ | i-Pr | H | H | H | Me | Me |
| O | $CH_2$ | Ph | H | H | H | Me | Me |
| O | $CH_2$ | Me | Me | H | H | Me | Me |
| O | $CH_2$ | i-Pr | Me | H | H | Me | Me |
| O | $CH_2$ | Ph | Me | H | H | Me | Me |
| O | $CH_2$ | Me | H | Me | H | Me | Me |
| O | $CH_2$ | i-Pr | H | Me | H | Me | Me |
| O | $CH_2$ | Ph | H | Me | H | Me | Me |
| O | $CH_2$ | Me | H | H | Me | Me | Me |
| O | $CH_2$ | i-Pr | H | H | Me | Me | Me |
| O | $CH_2$ | Ph | H | H | Me | Me | Me |
| O | $CH_2$ | Me | H | $CH_2Ph$ | H | Me | Me |
| O | $CH_2$ | i-Pr | H | $CH_2Ph$ | H | Me | Me |
| O | $CH_2$ | Ph | H | $CH_2Ph$ | H | Me | Me |

In a sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also be comprised of one or two $CR_7R_8$ groups, connected by a tether, selected independently from groups that include $CR_7R_8$, $CR_7R_8CR_7R_8$, $CR_7=C_8$, $CR_7R_8O$ and $CR_7R_8NR_7$.

the dotted line indicates the presence of either a single or double bond;

B is selected from the groups that include $CR^7R^8$, O, S or $NR^7$;

G is selected from the groups that include $OR^7$, $NR^7R^8$ or $SR^7$.

In another sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$; and the dotted line indicates the presence of either a single or double bond;

B is O;

G is $OR^7$.

In another sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

the dotted line indicates the presence of either a single or double bond;

B is O;

G is $NR^7R^8$.

In another sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$; and the dotted line indicates the presence of either a single or double bond;

B is O;

G is SR$^7$.

In another sub-embodiment, a structure of the formula (XIV) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S).

R$^2$, R$^3$, R$^4$, R$^5$, R$^6$, R$^7$ and R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S).

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$.

the dotted line indicates the presence of either a single or double bond;

B is CR$^7$R$^8$;

G OR$^7$.

In another sub-embodiment, a structure of the formula (XIV) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$_7$R$^8$, CR$^7$=CR$^8$, CR$^7$R$^8$O and CR$^7$R$^8$NR$^7$; and the dotted line indicates the presence of either a single or double bond;

B is CR$^7$R$^8$;

G is NR$^7$R$^8$.

In another sub-embodiment, a structure of the formula (XIV) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

the dotted line indicates the presence of either a single or double bond;

B is CR$^7$R$^8$;

G is SR$^7$.

In another sub-embodiment, a structure of the formula (XIV) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$_1$ and R$_2$, R$_2$ and R$_3$, R$_3$ and R$_4$, R$_4$ and R$_5$ and R$_5$ and R$_6$ can also each be comprised of one or two CR$_7$R$_8$ groups, connected by a tether, selected independently from groups that include CR$_7$R$_8$, CR$_7$R$_8$CR$_7$R$_8$, CR$_7$=CR$_8$, CR$_7$R$_8$O and CR$_7$R$_8$NR$_7$;

the dotted line indicates the presence of either a single or double bond;

B is S;

G is OR$^7$.

In another sub-embodiment, a structure of the formula (XIV) is given wherein the compound or its pharmaceutically acceptable salts or prodrug is defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

B is S;

G is $NR^7R^8$.

In another sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

B is S;

G is $SR^7$.

In another sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

B is $NR^7$;

G is $OR^7$.

In another sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

B is $NR^7$;

G is $NR^7R^8$.

In another sub-embodiment, a structure of the formula (XIV) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

B is $NR^7$;

G is $SR^7$.

In a particular embodiment of the present invention, the compounds of the formula (XIV) are the following species:

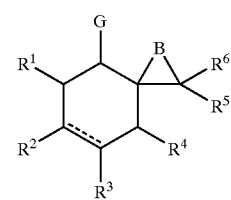

(XIV)

| G | B | $R^1$ | $R^2$ | $R^3$ | $R^4$ | $R^5$ | $R^6$ |
|---|---|---|---|---|---|---|---|
| OH | O | Me | H | H | H | Me | Me |
| OH | O | i-Pr | H | H | H | Me | Me |
| OH | O | Ph | H | H | H | Me | Me |

-continued (XIV)

| G | B | R¹ | R² | R³ | R⁴ | R⁵ | R⁶ |
|---|---|---|---|---|---|---|---|
| OH | O | Me | Me | H | H | Me | Me |
| OH | O | i-Pr | Me | H | H | Me | Me |
| OH | O | Ph | Me | H | H | Me | Me |
| OH | O | Me | H | Me | H | Me | Me |
| OH | O | i-Pr | H | Me | H | Me | Me |
| OH | O | Ph | H | Me | H | Me | Me |
| OH | O | Me | H | H | Me | Me | Me |
| OH | O | i-Pr | H | H | Me | Me | Me |
| OH | O | Ph | H | H | Me | Me | Me |
| OH | O | Me | H | CH₂Ph | H | Me | Me |
| OH | O | i-Pr | H | CH₂Ph | H | Me | Me |
| OH | O | Ph | H | CH₂Ph | H | Me | Me |
| OH | CH₂ | Me | H | H | H | Me | Me |
| OH | CH₂ | i-Pr | H | H | H | Me | Me |
| OH | CH₂ | Ph | H | H | H | Me | Me |
| OH | CH₂ | Me | Me | H | H | Me | Me |
| OH | CH₂ | i-Pr | Me | H | H | Me | Me |
| OH | CH₂ | Ph | Me | H | H | Me | Me |
| OH | CH₂ | Me | H | Me | H | Me | Me |
| OH | CH₂ | i-Pr | H | Me | H | Me | Me |
| OH | CH₂ | Ph | H | Me | H | Me | Me |
| OH | CH₂ | Me | H | H | Me | Me | Me |
| OH | CH₂ | i-Pr | H | H | Me | Me | Me |
| OH | CH₂ | Ph | H | H | Me | Me | Me |
| OH | CH₂ | Me | H | CH₂Ph | H | Me | Me |
| OH | CH₂ | i-Pr | H | CH₂Ph | H | Me | Me |
| OH | CH₂ | Ph | H | CH₂Ph | H | Me | Me |

In a sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7$=$CR_8$, $CR_7R_8O$ and $CR_7R_8NR_7$.

the dotted line indicates the presence of either a single or double bond;

B and D are selected from the groups that include $CR^7R^8$, O, S or $NR^7$;

G is selected from the groups that include $OR^7$, $NR^7R^8$ or $SR^7$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7$=$CR_8$, $CR_7R_8O$ and $CR_7R_8NR_7$; and the dotted line indicates the presence of either a single or double bond;

D=O, B=O and G=$OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7$=$CR_8$, $CR_7R_8O$ and $CR_7R_8NR_7$.

the dotted line indicates the presence of either a single or double bond;

D=O, B=$NR^8$ and G=$OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and the dotted line indicates the presence of either a single or double bond;

D=O, B=$CR^7R^8$, and G=$OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2$, $R^3$, $R^4$, $R^5$, $R^6$, $R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$.

the dotted line indicates the presence of either a single or double bond;

D=O, B=S and G=$OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R_6$, $R_7$, $R_8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR_7R^8$, $CR^7=CR^8$, $CR^7R^8O$ and $CR^7R^8NR^7$; and the dotted line indicates the presence of either a single or double bond;

D=O, B=O and G=$NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

D=O, B=$NR^8$ and G=$NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

the dotted line indicates the presence of either a single or double bond;

D=O, B=$CR^7R^8$ and G=$NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

the dotted line indicates the presence of either a single or double bond;

D=O, B=S and G=$NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=CR^7R^8$, $B=O$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^5$, $CR^7R^8CR^7R^8$, $CR^7=CR^8$, $CR^7R^8O$ and $CR^7R^8NR^7$;

the dotted line indicates the presence of either a single or double bond;

$D=CR^7R^8$, $B=NR^8$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=CR^7R^8$, $B=CR^7R^8$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=CR^7R^8$, $B=S$. and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=CR^7R$, $B=O$ and $G=NR^7R$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=CR^7R^8$, $B=NR^8$ and $G=NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^5NR^7$;

the dotted line indicates the presence of either a single or double bond;

$D=C^7R^8$, $B=CR^7R^8$ and $G=NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=CR^7R^8$, $B=S$ and $G=NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^5$, $CR^7=CR^8$, $CR^7R^8O$ and $CR^7R^8NR^7$;

the dotted line indicates the presence of either a single or double bond;

$D=S$, $B=O$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=S$, $B=NR^8$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=S$, $B=CR^7R^8$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=S$, $B=S$. and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^{R8}O$ and $CR^7R^8NR^7$;

the dotted line indicates the presence of either a single or double bond;

$D=S$, $B=O$ and $G=NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=S$, $B=NR^8$ and $G=NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=S$, $B=CR^7R^8$ and $G=NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=S$, $B=S$ and $G=NR^7R^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=NR^7$, $B=O$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8N^7$;

the dotted line indicates the presence of either a single or double bond;

$D=NR^7$, $B=NR^8$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=NR^7$, $B=CR^7R^8$ and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

the dotted line indicates the presence of either a single or double bond;

$D=NR^7$, $B=S$. and $G=OR^8$.

In another sub-embodiment, a structure of the formula (XV) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=NR^8$ or S);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

the dotted line indicates the presence of either a single or double bond;

D=NR$^7$, B=O and G=NR$^7$R$^8$.

In another sub-embodiment, a structure of the formula (XV) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

the dotted line indicates the presence of either a single or double bond;

D=NR$^7$, B=NR$^8$ and G=NR$^7$R$^8$.

In another sub-embodiment, a structure of the formula (XV) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

the dotted line indicates the presence of either a single or double bond;

D=NR$^7$, B=CR$^7$R$^8$ and G=NR$^7$R$^8$.

In another sub-embodiment, a structure of the formula (XV) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

the dotted line indicates the presence of either a single or double bond;

D=NR$^7$, B=S and G=NR$^7$R$^8$.

In a particular embodiment of the present invention, the compounds of the formula (XV) are the following species:

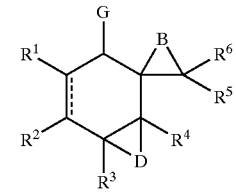

| G | B | D | R$^1$ | R$^2$ | R$^3$ | R$^4$ | R$^5$ | R$^6$ |
|---|---|---|---|---|---|---|---|---|
| OH | O | O | Me | H | H | H | Me | Me |
| OH | O | O | i-Pr | H | H | H | Me | Me |
| OH | O | O | Ph | H | H | H | Me | Me |
| OH | O | O | Me | Me | H | H | Me | Me |
| OH | O | O | i-Pr | Me | H | H | Me | Me |
| OH | O | O | Ph | Me | H | H | Me | Me |
| OH | O | O | Me | H | Me | H | Me | Me |
| OH | O | O | i-Pr | H | Me | H | Me | Me |
| OH | O | O | Ph | H | Me | H | Me | Me |
| OH | O | O | Me | H | H | Me | Me | Me |
| OH | O | O | i-Pr | H | H | Me | Me | Me |
| OH | O | O | Ph | H | H | Me | Me | Me |
| OH | O | O | Me | H | CH$_2$Ph | H | Me | Me |
| OH | O | O | i-Pr | H | CH$_2$Ph | H | Me | Me |
| OH | O | O | Ph | H | CH$_2$Ph | H | Me | Me |
| OH | CH$_2$ | O | Me | H | H | H | Me | Me |
| OH | CH$_2$ | O | i-Pr | H | H | H | Me | Me |
| OH | CH$_2$ | O | Ph | H | H | H | Me | Me |
| OH | CH$_2$ | O | Me | Me | H | H | Me | Me |
| OH | CH$_2$ | O | i-Pr | Me | H | H | Me | Me |
| OH | CH$_2$ | O | Ph | Me | H | H | Me | Me |
| OH | CH$_2$ | O | Me | H | Me | H | Me | Me |
| OH | CH$_2$ | O | i-Pr | H | Me | H | Me | Me |
| OH | CH$_2$ | O | Ph | H | Me | H | Me | Me |
| OH | CH$_2$ | O | Me | H | H | Me | Me | Me |
| OH | CH$_2$ | O | i-Pr | H | H | Me | Me | Me |
| OH | CH$_2$ | O | Ph | H | H | Me | Me | Me |
| OH | CH$_2$ | O | Me | H | CH$_2$Ph | H | Me | Me |
| OH | CH$_2$ | O | i-Pr | H | CH$_2$Ph | H | Me | Me |
| OH | CH$_2$ | O | Ph | H | CH$_2$Ph | H | Me | Me |
| OH | O | CH$_2$ | Me | H | H | H | Me | Me |
| OH | O | CH$_2$ | i-Pr | H | H | H | Me | Me |
| OH | O | CH$_2$ | Ph | H | H | H | Me | Me |
| OH | O | CH$_2$ | Me | Me | H | H | Me | Me |
| OH | O | CH$_2$ | i-Pr | Me | H | H | Me | Me |
| OH | O | CH$_2$ | Ph | Me | H | H | Me | Me |
| OH | O | CH$_2$ | Me | H | Me | H | Me | Me |
| OH | O | CH$_2$ | i-Pr | H | Me | H | Me | Me |
| OH | O | CH$_2$ | Ph | H | Me | H | Me | Me |
| OH | O | CH$_2$ | Me | H | H | Me | Me | Me |
| OH | O | CH$_2$ | i-Pr | H | H | Me | Me | Me |
| OH | O | CH$_2$ | Ph | H | H | Me | Me | Me |
| OH | O | CH$_2$ | Me | H | CH$_2$Ph | H | Me | Me |
| OH | O | CH$_2$ | i-Pr | H | CH$_2$Ph | H | Me | Me |
| OH | O | CH$_2$ | Ph | H | CH$_2$Ph | H | Me | Me |

In a sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

The dotted line indicates the presence of either a single or double bond;

D is selected from the groups that include $CR^7R^8$, O, S or $NR^7$;

G is selected from the groups that include $OR^7$, $NR^7R^8$ or $SR^7$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$; and The dotted line indicates the presence of either a single or double bond;

D is O;

G is $OR^7$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

The dotted line indicates the presence of either a single or double bond;

D is O;

G is $NR^7R^8$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and The dotted line indicates the presence of either a single or double bond;

D is O;

G is $SR^7$.

In another sub-embodiment, a structure of the formula (XVI) is given wherein the compound or its pharmaceutically acceptable salts or prodrug is defined as follows:

$R^1$ is selected independently from the groups that include hydrogen, allyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^2, R^3, R^4, R^5, R^6, R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$.

The dotted line indicates the presence of either a single or double bond;

D is $CR^7R^8$;

G $OR^7$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$; and The dotted line indicates the presence of either a single or double bond;

D is $CR^7R^8$;

G is $NR^7R^8$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

The dotted line indicates the presence of either a single or double bond;

D is $CR^7R^8$;

G is $SR^7$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$;

The dotted line indicates the presence of either a single or double bond;

D is S;

G is $OR^7$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^5$, $CR^7R^8O$ and $CR^7R^8NR^7$;

The dotted line indicates the presence of either a single or double bond;

D is S;

G is $NR^7R^8$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

The dotted line indicates the presence of either a single or double bond;

D is S;

G is $SR^7$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^5$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

The dotted line indicates the presence of either a single or double bond;

D is $NR^7$;

G is $OR^7$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

The dotted line indicates the presence of either a single or double bond;

D is $NR^7$;

G is $NR^7R^8$.

In another sub-embodiment, a structure of the formula (XVI) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

The dotted line indicates the presence of either a single or double bond;

D is $NR^7$;

G is $SR^7$.

In a sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^1, R^2, R^3, R^4, R^5, R^6, R^7, R^8, R^9, R^{10}, R^{12}, R^{13}, R^{14}, r^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

D and E are selected from the groups that include $CR^7R^8$, O, S or $NR^7$;

G is selected from the groups that include $OR^7$, $NR^7R^8$ or $SR^7$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$; and E=O, D=O and G=$OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

$E=O$, $D=NR^8$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and $E=O$, $D=CR^7R^8$, and $G=OR^8$.

In another sub-embodiment, a structure of the formula (XVII) is given wherein the to compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^2, R^3, R^4, R^5, R^6, R^7$ and $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8N^7$.

$E=O$, $D=S$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR_7R^8$, $CR^7=CR^8$, $CR^7R^8O$ and $CR^7R^8NR^7$; and $E=O$, $D=O$ and $G=NR^7R^8$.

In another sub-embodiment, a structure of the formula (XVH) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^5$, $CR^7R^8O$ and $CR^7R^8NR^7$;

$E=O$, $D=NR^8$ and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or $S$);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

$E=O$, $D=CR^7R^8$ and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or $S$);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or $S$);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

$E=O$, $D=S$ and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or $S$);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or $S$);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=CR^7R^8$, $D=O$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or $S$);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or $S$);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=CR^7R^8$, $D=NR^8$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or $S$);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or $S$);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=CR^7R^8$, $D=CR^7R^8$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or $S$);

$R^2$, $R^3$, $R^4$, $R^5$, $R^6$, $R^7$, $R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or $S$);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=CR^7R^8$, $D=S$, and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$E=CR^7R^8$, $D=O$ and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$E=CR^7R^8$, $D=NR^8$ and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$E=CR^7R^8$, $D=CR^7R^8$ and $G=NR^7R$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$E=CR^7R^8$, $D=S$ and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$E=S$, $D=O$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

$E=S$, $D=NR^8$ and $G=OR^8$.

In another sub-embodiment, a structure of the formula (XVII) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);
- $R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, and $CR^7R^8NR^7$;
- E=S, D=$CR^7R^8$ and G=$OR^8$.

In another sub-embodiment, a structure of the formula (XVII) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);
- $R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);
- $R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;
- E=S, D=S. and G=$OR^8$.

In another sub-embodiment, a structure of the formula (XVII) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);
- $R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);
- $R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;
- E=S, D=O and G=$NR^7R^8$.

In another sub-embodiment, a structure of the formula (XVII) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);
- $R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);
- $R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7RN^8R^7$;
- E=S, D=$NR^8$ and G=$NR^7R^8$.

In another sub-embodiment, a structure of the formula (XVII) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);
- $R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);
- $R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;
- E=S, D=$CR^7R^8$ and G=$NR^7R^8$.

In another sub-embodiment, a structure of the formula (XVII) is given wherein the compound or its pharmaceutically acceptable salts or prodrug is defined as follows:

- $R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $Xk^7$ ($X=O$, $NR^8$ or S);
- $R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);
- $R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;
- E=S, D=S and G=$N^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=NR^7$, D=O and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=NR^7$, $D=NR^8$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=NR^7$, $D=CR^7R^8$ and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=NR^7$, D=S. and $G=OR^8$.

In another sub-embodiment, a structure of the formula (XVII) is given wherein the compound or its pharmaceutically acceptable salts or prodrug is defined as follows:

$R^1$ is selected independently from the groups that include hydrogen, allyl, cycloalkyl, aryl, alkaryl, arylalkyl, heterocyclic, ester, alkcarbonyl, carbonyl, halide, a residue of a natural or synthetic amino acid, or carbohydrate or is (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=NR^7$, D=O and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$E=NR^7$, $D=NR^8$ and $G=NR^7R^8$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^5$, $CR^7R^8O$ and $CR^7R^8NR^7$;

$E=NR^7$, $D=CR^7R^8$ and $G=NR^7R^5$.

In another sub-embodiment, a structure of the formula (XVII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, to a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^5NR^7$;

$E=NR^7$, D=S and $G=NR^7R^8$.

In a sub-embodiment, a structure of the formula (XVIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

The dotted line indicates the presence of either a single or double bond, wherein the presence of a single bond, the valences are completed by hydrogens;

G is $OR^7$.

In another sub-embodiment, a structure of the formula (XVIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$, and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

The dotted line indicates the presence of either a single or double bond, wherein the presence of a single bond, the valences are completed by hydrogens;

G is $NR^7R^8$.

In another sub-embodiment, a structure of the formula (XVIII) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

The dotted line indicates the presence of either a single or double bond, wherein the presence of a single bond, the valences are completed by hydrogens;

G is $SR^7$.

In a sub-embodiment, a structure of the formula (XIX) is given wherein the compound or its pharmaceutically acceptable salts or prodrug is defined as follows:

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R^1$ and $R^2$, $R^2$ and $R^3$ $R^3$ and $R^4$, $R^4$ and $R^5$, and $R^5$ and $R^6$ can also each be comprise of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

B and M are selected from the groups that include $CR^7R^8O$, S or $NR^7$; and

A is selected from the groups that include O, $NR^7$ or S.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

B and M are selected from the groups that include $CR^7R_8$, O, S or $NR_7$;

A is selected from the groups that include O, $NR^7$ or S.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$; and M=O, B=O and A=O.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

M=O, B=$NR^8$ and A=O.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R_4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and M=O, B=$CR^7R^8$, and A=O.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$.

$M=O$, $B=S$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$; and $M=O$, $B=O$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=O$, $B=NR^8$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

$M=O$, $B=CR^7R^8$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=O$, $B=S$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^5$, $CR^7R^8O$ and $CR^7R^8NR^7$;

$M=CR^7R^8$, $B=O$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=NR^8$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=CR^7R^8$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=S$. and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^5$, $CR^7=CR^8$, $CR^7R^8O$ and $CR^7R^8NR^7$;

$M=CR^7R^8$, $B=O$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=NR^8$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=CR^7R^8$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^4$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=S$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=S$, $B=O$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=S$, $B=NR^8$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=S$, $B=CR^7R^8$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=S. and A=O.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=O and A=$NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=$NR^8$ and A=$NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=$CR^7R^8$ and A=$NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=S and A=$NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=$NR^7$, B=O and A=O.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^5$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=NR^8$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=CR^7R^8$ and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=S$. and $A=O$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=O$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=NR^8$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7 (X=O, NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=CR^7R^8$ and $A=NR^7$.

In another sub-embodiment, a structure of the formula (XIX) is given wherein the compound or its pharmaceutically acceptable salts or prodrug is defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ $(X=O, NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ $(X=O, NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=S$ and $A=NR^7$.

In a particular embodiment of the present invention, the compounds of the formula (XIX) are the following species:

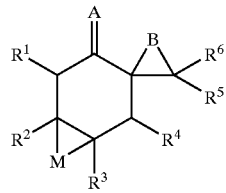

(XIX)

| A | B | M | $R^1$ | $R^2$ | $R^3$ | $R^4$ | $R^5$ | $R^6$ |
|---|---|---|---|---|---|---|---|---|
| O | O | O | Me | H | H | H | Me | Me |
| O | O | O | i-Pr | H | H | H | Me | Me |
| O | O | O | Ph | H | H | H | Me | Me |
| O | O | O | Me | Me | H | H | Me | Me |
| O | O | O | i-Pr | Me | H | H | Me | Me |
| O | O | O | Ph | Me | H | H | Me | Me |
| O | O | O | Me | H | Me | H | Me | Me |
| O | O | O | i-Pr | H | Me | H | Me | Me |
| O | O | O | Ph | H | Me | H | Me | Me |
| O | O | O | Me | H | H | Me | Me | Me |
| O | O | O | i-Pr | H | H | Me | Me | Me |
| O | O | O | Ph | H | H | Me | Me | Me |
| O | O | O | Me | H | $CH_2Ph$ | H | Me | Me |
| O | O | O | i-Pr | H | $CH_2Ph$ | H | Me | Me |
| O | O | O | Ph | H | $CH_2Ph$ | H | Me | Me |
| O | $CH_2$ | O | Me | H | H | H | Me | Me |
| O | $CH_2$ | O | i-Pr | H | H | H | Me | Me |
| O | $CH_2$ | O | Ph | H | H | H | Me | Me |
| O | $CH_2$ | O | Me | Me | H | H | Me | Me |
| O | $CH_2$ | O | i-Pr | Me | H | H | Me | Me |
| O | $CH_2$ | O | Ph | Me | H | H | Me | Me |

-continued

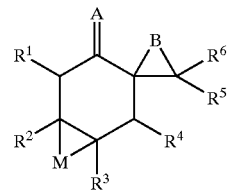

(XIX)

| A | B | M | $R^1$ | $R^2$ | $R^3$ | $R^4$ | $R^5$ | $R^6$ |
|---|---|---|---|---|---|---|---|---|
| O | $CH_2$ | O | Me | H | Me | H | Me | Me |
| O | $CH_2$ | O | i-Pr | H | Me | H | Me | Me |
| O | $CH_2$ | O | Ph | H | Me | H | Me | Me |
| O | $CH_2$ | O | Me | H | H | Me | Me | Me |
| O | $CH_2$ | O | i-Pr | H | H | Me | Me | Me |
| O | $CH_2$ | O | Ph | H | H | Me | Me | Me |
| O | $CH_2$ | O | Me | H | $CH_2Ph$ | H | Me | Me |
| O | $CH_2$ | O | i-Pr | H | $CH_2Ph$ | H | Me | Me |
| O | $CH_2$ | O | Ph | H | $CH_2Ph$ | H | Me | Me |

In a sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ $(X=O, NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ $(X=O, NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$.

B and M are selected from the groups that include $CR^7R^8$, O, S or $NR^7$;

G is selected from the groups that include $OR^7$, $NR^7R^8$ or $SR^7$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ $(X=O, NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ $(X=O, NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$; and M=O, B=O and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7{=}CR_8$, $CR_7R_8O$ and $CR_7R_8NR_7$.

M=O, B=$NR^8$ and G=$OR^8$.

In another sub-embodiment, a structure of the fonnula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^5$, $CR^7{=}CR^8$, $CR^7R^8O$ and $CR^7R^8NR^7$; and M=O, B=$CR^7R^8$, and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S).

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S).

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$.

M=O, B=S and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^5$ groups, connected by a tether, selected independently from groups that include $CR^7R^8$, $CR^7R^8CR_7R^8$, $CR^7{=}CR^8$, $CR^7R^8O$ and $CR^7R^8NR^7$; and M=O, B=O and G=$NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7{=}CR^8$, $CR^7R^8O$ and $CR^7R^8NR^7$;

M=O, B=$NR^8$ and G=$NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

$M=O$, $B=CR^7R^8$ and $G=NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$($X=O$, $NR^8$ or S);

$R_1$ and $R_2$, $R_2$ and $R_3$, $R_3$ and $R_4$, $R_4$ and $R_5$ and $R_5$ and $R_6$ can also each be comprised of one or two $CR_7R_8$ groups, connected by a tether, selected independently from groups that include $CR_7R_8$, $CR_7R_8CR_7R_8$, $CR_7=CR_8$, $CR_7R_8O$ and $CR_7R_8NR_7$;

$M=O$, $B=S$ and $G=NR^7R$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=O$ and $G=OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=NR^8$ and $G=OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ ($X=O$, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=CR^7R^8$, $B=CR^7R^8$ and $G=OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ ($X=O$, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$($X=O$, $NR^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

M=CR$^7$R$^8$, B=S. and G=OR$^8$.

In another sub-embodiment, a structure of the formula (XX) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^1$, R$^2$, R$^3$, R$^4$, R$^5$, R$^6$, R$^7$, R$^8$, R$^9$, R$^{10}$, R$^{12}$, R$^{13}$, R$^{14}$, R$^{15}$, R$^{16}$, R$^{17}$, R$^{18}$ and R$^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$(X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

M=CR$^7$R$^8$, B=O and G=NR$^7$R$^8$.

In another sub-embodiment, a structure of the formula (XX) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^1$, R$^2$, R$^3$, R$^4$, R$^5$, R$^6$, R$^7$, R$^8$, R$^9$, R$^{10}$, R$^{12}$, R$^{13}$, R$^{14}$, R$^{15}$, R$^{16}$, R$^{17}$, R$^{18}$ and R$^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$(X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

M=CR$^7$R$^8$, B=NR$^8$ and G=NR$^7$R$^8$.

In another sub-embodiment, a structure of the formula (XX) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^1$, R$^2$, R$^3$, R$^4$, R$^5$, R$^6$, R$^7$, R$^8$, R$^9$, R$^{10}$, R$^{12}$, R$^{13}$, R$^{14}$, R$^{15}$, R$^{16}$, R$^{17}$, R$^{18}$ and R$^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

M=CR$^7$R$^8$, B=CR$^7$R$^8$ and G=NR$^7$R$^8$.

In another sub-embodiment, a structure of the formula (XX) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^2$, R$^3$, R$^4$, R$^5$, R$^6$, R$^7$, R$^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$ and R$^2$, R$^2$ and R$^3$, R$^3$ and R$^4$, R$^4$ and R$^5$ and R$^5$ and R$^6$ can also each be comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

M=CR$^7$R$^8$, B=S and G=NR$^7$R$^8$.

In another sub-embodiment, a structure of the formula (XX) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR$^7$ (X=O, NR$^8$ or S);

R$^1$, R$^2$, R$^3$, R$^4$, R$^5$, R$^6$, R$^7$, R$^8$, R$^9$, R$^{10}$, R$^{12}$, R$^{13}$, R$^{14}$, R$^{15}$, R$^{16}$, R$^{17}$, R$^{18}$ and R$^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or XR$^7$ (X=O, NR$^8$ or S);

R$^1$, R$^2$, R$^3$, R$^4$, R$^5$, R$^6$, R$^7$, R$^8$, R$^9$, R$^{10}$, R$^{12}$, R$^{13}$, R$^{14}$, R$^{15}$, R$^{16}$, R$^{17}$, R$^{18}$ and R$^{19}$ are comprised of one or two CR$^7$R$^8$ groups, connected by a tether, selected independently from groups that include CR$^7$R$^8$, CR$^7$R$^8$CR$^7$R$^8$, CR$^7$=CR$^8$, CR$^7$R$^8$O and CR$^7$R$^8$NR$^7$;

M=S, B=O and G=OR$^8$.

In another sub-embodiment, a structure of the formula (XX) is given wherein the compound or its pharmaceutically acceptable salts or prodrug are defined as follows:

R$^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=$NR^8$ and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=$CR^7R^8$ and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=S. and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^5NR^7$;

M=S, B=O and G=$NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^2, R^3, R^4, R^5, R^6, R^7, R^8$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=$NR^8$ and G=$NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=S, B=$CR^7R^8$ and G=$NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=$NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$(X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^5$, $CR^7R^8O$ and $CR^7R^8NR^7$;

M=S, B=S and G=$NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=$NR^7$, B=O and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=$NR^7$, B=$NR^8$ and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=$NR^7$, B=$CR^7R^8$ and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

M=$NR^7$, B=S. and G=$OR^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or XR X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $Xk^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, B=O and $G=NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=NR^8$ and $G=NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, $B=CR^7R^8$ and $G=NR^7R^8$.

In another sub-embodiment, a structure of the formula (XX) is given wherein the compound or its pharmaceutically acceptable salts or prodrug are defined as follows:

$R^1$ is selected independently from the groups that include hydrogen, alkyl, cycloalkyl, aryl, alkaryl, arylalkyl, heterocyclic, ester, alkcarbonyl, carbonyl, halide, a residue of a natural or synthetic amino acid, or carbohydrate or $XR^7$ (X=O, $NR^8$ or S);

$R^1, R^2, R^3, R^4, R^5, R^6, R^7, R^8, R^9, R^{10}, R^{12}, R^{13}, R^{14}, R^{15}, R^{16}, R^{17}, R^{18}$ and $R^{19}$ are selected independently from the groups that include hydrogen, alkyl, alkenyl, alkynyl, cycloalkyl, cycloalkenyl, aryl, alkaryl, arylalkyl, heterocyclic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, halide, a residue of a natural or synthetic amino acid, or carbohydrate or $XR^7$ (X=O, $NR^8$ or S);

$R^1$ and $R^2$, $R^2$ and $R^3$, $R^3$ and $R^4$, $R^4$ and $R^5$ and $R^5$ and $R^6$ can also each be comprised of one or two $CR^7R^8$ groups, connected by a tether, selected independently from groups that include $CR^7R^8$, $CR^7R^8CR^7R^8$, $CR^7=CR^8$, $CR^7R^8O$ and $CR^7R^8NR^7$;

$M=NR^7$, B=S and $G=NR^7R^8$.

In a particular embodiment of the present invention, the compounds of the formula (XX) are the following species:

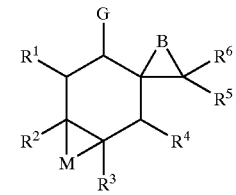

(XX)

| G | B | M | $R^1$ | $R^2$ | $R^3$ | $R^4$ | $R^5$ | $R^6$ |
|---|---|---|---|---|---|---|---|---|
| OH | O | O | Me | H | H | H | Me | Me |
| OH | O | O | i-Pr | H | H | H | Me | Me |
| OH | O | O | Ph | H | H | H | Me | Me |
| OH | O | O | Me | Me | H | H | Me | Me |
| OH | O | O | i-Pr | Me | H | H | Me | Me |
| OH | O | O | Ph | Me | H | H | Me | Me |
| OH | O | O | Me | H | Me | H | Me | Me |
| OH | O | O | i-Pr | H | Me | H | Me | Me |
| OH | O | O | Ph | H | Me | H | Me | Me |
| OH | O | O | Me | H | H | Me | Me | Me |
| OH | O | O | i-Pr | H | H | Me | Me | Me |
| OH | O | O | Ph | H | H | Me | Me | Me |
| OH | O | O | Me | H | $CH_2Ph$ | H | Me | Me |
| OH | O | O | i-Pr | H | $CH_2Ph$ | H | Me | Me |
| OH | O | O | Ph | H | $CH_2Ph$ | H | Me | Me |
| OH | $CH_2$ | O | Me | H | H | H | Me | Me |
| OH | $CH_2$ | O | i-Pr | H | H | H | Me | Me |
| OH | $CH_2$ | O | Ph | H | H | H | Me | Me |
| OH | $CH_2$ | O | Me | Me | H | H | Me | Me |
| OH | $CH_2$ | O | i-Pr | Me | H | H | Me | Me |
| OH | $CH_2$ | O | Ph | Me | H | H | Me | Me |
| OH | $CH_2$ | O | Me | H | Me | H | Me | Me |
| OH | $CH_2$ | O | i-Pr | H | Me | H | Me | Me |
| OH | $CH_2$ | O | Ph | H | Me | H | Me | Me |
| OH | $CH_2$ | O | Me | H | H | Me | Me | Me |
| OH | $CH_2$ | O | i-Pr | H | H | Me | Me | Me |
| OH | $CH_2$ | O | Ph | H | H | Me | Me | Me |
| OH | $CH_2$ | O | Me | H | $CH_2Ph$ | H | Me | Me |
| OH | $CH_2$ | O | i-Pr | H | $CH_2Ph$ | H | Me | Me |
| OH | $CH_2$ | O | Ph | H | $CH_2Ph$ | H | Me | Me |
| OH | O | $CH_2$ | Me | H | H | H | Me | Me |
| OH | O | $CH_2$ | i-Pr | H | H | H | Me | Me |
| OH | O | $CH_2$ | Ph | H | H | H | Me | Me |
| OH | O | $CH_2$ | Me | Me | H | H | Me | Me |
| OH | O | $CH_2$ | i-Pr | Me | H | H | Me | Me |
| OH | O | $CH_2$ | Ph | Me | H | H | Me | Me |

-continued (XX)

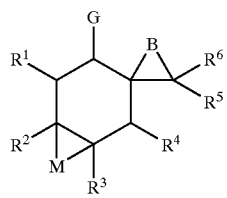

| G | B | M | R¹ | R² | R³ | R⁴ | R⁵ | R⁶ |
|---|---|---|---|---|---|---|---|---|
| OH | O | CH₂ | Me | H | Me | H | Me | Me |
| OH | O | CH₂ | i-Pr | H | Me | H | Me | Me |
| OH | O | CH₂ | Ph | H | Me | H | Me | Me |
| OH | O | CH₂ | Me | H | H | Me | Me | Me |
| OH | O | CH₂ | i-Pr | H | H | Me | Me | Me |
| OH | O | CH₂ | Ph | H | H | Me | Me | Me |
| OH | O | CH₂ | Me | H | CH₂Ph | H | Me | Me |
| OH | O | CH₂ | i-Pr | H | CH₂Ph | H | Me | Me |
| OH | O | CH₂ | Ph | H | CH₂Ph | H | Me | Me |

II. Definitions

It should be understood that the various possible stereoisomers of the groups mentioned above and herein are within the meaning of the individual terms and examples, unless otherwise specified. As an illustrative example, "1-methyl-butyl" exists in both the (R) and the (S) form, thus, both (R)-1-methyl-butyl and (S)-1-methyl-butyl is covered by the term "1-methyl-butyl," unless otherwise specified. Several biological compounds are designed by the (D) and the (L) form, rather than the (R) and the (S) form, respectively, based on the stereochemistry around the 4' carbon. As an another illustrative example, "glycine" exists in both the (D) and the (L) form; therefore, both (D)-glycine and (L)-glycine are covered by the term "glycine" unless otherwise specified.

As used herein, the term "isolated enantiomer" refers to a composition that includes at least approximately 95% to 100%, or more preferably, over 97% of a single enantiomer of that compound.

As used herein, the term "substantially free of" or "substantially in the absence of" refers to a composition that includes at least 85 or 90% by weight, preferably 95% to 98% by weight, and even more preferably 99% to 100% by weight, of the designated enantiomer of that compound.

The term "independently" is used herein to indicate that the variable that is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

The term alkyl, as used herein, unless otherwise specified, refers to a saturated straight, branched, or cyclic, primary, secondary, or tertiary hydrocarbon, typically of $C_1$ too $C_{18}$ and specifically includes methyl, ethyl, propyl, isopropyl, butyl, isobutyl, t-butyl, pentyl, cyclopentyl, isopentyl, neopentyl, hexylisohexyl, cyclohexyl, cyclohexylmethyl, 3-methylpentyl, 2,2-dimethylbutyl and 2,3-dimethylbutyl. The alkyl group can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms.

The term alkylene or alkenyl refers to a saturated hydrocarbyldiyl radical of straight or branched configuration, including but not limited to those that have from one to ten carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like. The alkylene group or other divalent moiety disclosed herein can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art or organic synthesis. Suitable protecting groups are described, for example, in Greene, et al., "Protective Groups in Organic Synthesis," John Wiley and Sons, Second Edition, 1991, hereby incorporated by reference.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, halo, nitro, cyano, sulfonic acid, sulfate, phosphonic acid, phosphate or phosphonate, either unprotected, or protected as necessary, as known to those skilled in the art, for example, as taught in Greene, et al., "Protective Groups in Organic Synthesis," John Wiley and Sons, Second Edition, 1991.

The term aralkyl, as used herein, and unless otherwise specified, refers to an aryl group as defined above linked to the molecule through an alkyl group as defined above. The term alkaryl or alkylaryl as used herein, and unless otherwise specified, refers to an alkyl group as defined above linked to the molecule through an aryl group as defined above. In each of these groups, the alkyl group can be optionally substituted as describe above and the aryl group can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included within the scope of the term aryl are phenyl; naphthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like.

The term halo or halogen, as used herein includes chloro, bromo, iodo and fluoro.

The term heteroatom, as used herein, refers to oxygen, sulfur, nitrogen or phosphorus.

The term alkylamino or arylamino refers to an amino group that has one or two alkyl or aryl substituents, respectively.

The term alkoxy, as used herein, and unless otherwise specified, refers to a moiety of the structure —O-alkyl, wherein alkyl is as defined above.

The term acyl refers to moiety of the formula —C(O)R', wherein R' is alkyl; aryl, alkaryl, aralkyl, heteroaromatic, heterocyclic, alkoxyalkyl including methoxymethyl; arylalkyl including benzyl; aryloxyalkyl, such as phenoxymethyl; aryl including phenyl optionally substituted with halo groups $C_1$ to $C_4$ alkyl or $C_1$ to $C_4$ alkoxy or the residue of an amino acid.

As used herein, a leaving group means a functional group that is cleaved from the molecule to which it is attached under appropriate conditions.

The term heteroaryl or heteroaromatic, as used herein, refers to an aromatic that includes at least one sulfur, oxygen, nitrogen or phosphorus in the aromatic ring. The term heterocyclic refers to a nonaromatic cyclic group wherein there is at least one heteroatom, such as oxygen, sulfur, nitrogen or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, or imidazole. The heteroaromatic group can be optionally substituted as described above for aryl. The heterocyclic group can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference. The heteroaromatic can be partially or totally hydrogenated as desired. As a non-limiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term amino acid includes naturally occurring and synthetic amino acids, and includes but is not limited to, alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl and histidinyl.

The term "ether," as used herein, refers to oxygen that is disubstituted with independent alkyl groups or two alkyl groups that together formed a ring or a bridge. Some non-limiting examples include 4-(tetrahydrobenzimidazol-1-yl)butoxy, 5-(tetra-hydrobenzimidazol-1-yl)pentoxy, ethoxy, n-propoxy or isoproproxy. The ethers also can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "amide," as used herein, refers to a carbonyl moiety wherein the non-alkyl moiety is formed from an amine. Some non-limiting examples are formylamino, acetylamino, propionylamino, butanoylamino, isobutanoylamino, pentanoylamino, 3-methyl-butanoylamino, hexanoylamino, methoxycarbonylamino, ethoxycarbonylamino, n-propoxycarbonylamino, isopropoxycarbonylamino, benzamido, cyclopentylcarbonyl-amido, cyclohexylcarbonylamido, cycloheptylcarbonyl-amido, phenylacetylamido, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "sulfamoyl" is a hexavalent sulfur covalently bound to at least two oxygens and a nitrogen. Some non-limiting examples include methanesulphonylamino, ethanesulphonylamino, n-propanesulphonylamino, isopropanesulphonylamino, n-butane-sulphonylamino, N-ethyl-phenylmethanesulphonylamido, N-ethyl-2-phenylethane-sulphonylamido, N-ethyl-3-phenylpropanesulphonylamido, N-ethyl-naphthalen-1-yl-sulphonamido or N-ethyl-naphthalen-2-yl-sulphonylamido. The sulfamoyl group also can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "thio" refers to a sulfur covalently bound to a hydrogen or a carbon based group. Some non-limiting examples include methylmercapto, ethylmercapto, n-propylmercapto, isopropylmercapto or n-butylmercapto, ethylthio, n-propylthio or isopropylthio group. The thio group also can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "ester" refers to a carbonyl flanked by an alkoxy group and a carbon based group. Some non-limiting examples include hydroxycarbonyl, methoxycarbonyl, ethoxycarbonyl, n-propyloxycarbonyl, isopropyloxycarbonyl, n-butyloxycarbonyl, isobutyloxycarbonyl, tert-butyloxycarbonyl or 1-(cinnamyloxycarbonyloxy)-ethoxycarbonyl. The ester group also can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "urethane" or "carbamate" refers to —OC(O)NR$^4$R$^5$ in which R$^4$ and R$^5$ are independently selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the carbamide optimally comprise a phenyl group. The term "lower carbamide" refers to an carbamide group in which the non-carbonyl moiety is a lower alkyl. The carbamide group also can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term carbohydrate, used herein refers to mono, di, tri, oligo, and poly saccharides consisting of furanose and pyranose sugars such as threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, or cellulose. The carbohydrate moiety as disclosed herein can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term alkylheteroaryl refers to an alkyl group substituted by a heteroaryl substituent.

The term host, as used herein, refers to a multicellular organism in which the symptoms of an autoimmune or inflammatory disorder, including animals, and preferably a human. The term host specifically refers to animals, in particular, primates (including chimpanzees) and humans, in which autoimmune and inflammatory disorders occur. In most animal applications of the present invention, the host is a human patient. Veterinary applications, in certain indications, however, are clearly anticipated by the present invention (such as chimpanzees).

III. Pharmaceutically Acceptable Salt Formulations

Modifications of the active compound can affect the bioavailability and rate of metabolism of the active species, thus providing control over the delivery of the active species. Further, the modifications can affect the activity of the compound, in some cases increasing the activity over the parent compound. This can easily be assessed by preparing the derivative and testing its activity according to the methods described herein, or other method known to those skilled in the art.

In cases where compounds are sufficiently basic or acidic to form stable nontoxic acid or base salts, administration of the compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess anti-inflammatory activity, or are metabolized to a compound that exhibits such activity.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of the compound. Examples of substituent groups that can replace one or more hydrogens on the compound are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed compounds to achieve a desired effect.

IV. Autoimmune and Inflammatory Diseases

The compounds of the present invention can be used to treat any disorder that is mediated by LO. Dysfunction in LO production is implicated in a wide variety of disease states, including but not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, and conjunctivitis.

Nonlimiting examples of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus.

Human endothelial disorders mediated by LO include psoriasis, eczematous dermatitis, Kaposi's sarcoma as well as proliferative disorders of smooth muscle cells.

In yet another embodiment, the compounds disclosed herein can be selected to treat anti-inflammatory conditions that are mediated by mononuclear leukocytes.

In one embodiment, the compounds of the present invention are selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

V. Combination and Alternation Therapy

Any of the compounds disclosed herein can be administered in combination or alternation with a second biologically active agent to increase its effectiveness against the target disorder.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted as that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps third, agent that induces a different biological pathway from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the condition.

Any method of alternation can be used that provides treatment to the patient. Nonlimiting examples of alternation patterns include 1–6 weeks of administration of an effective amount of one agent followed by 1–6 weeks of administration of an effective amount of a second agent. The alternation schedule can include periods of no treatment. Combination therapy generally includes the simultaneous administration of an effective ratio of dosages of two or more active agents.

Illustrative examples of specific agents that can be used in combination or alternation with the compounds of the present invention are described below in regard to asthma and arthritis. The agents set out below or others can alternatively be used to treat a host suffering from any of the other disorders listed in Section IV or that are mediated by LO, and preferably 15-LO.

Asthma

In one embodiment, the compound of the present invention is administered in combination or alternation with heparin, frusemide, ranitidine, an agent that effects respiratory function, such as DNAase, or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-$D_4$-receptor antagonists such as Accolate (zafirlukast), Ziflo (zileuton), leukotriene $C_1$ or $C_2$ antagonists and inhibitors of leukotriene synthesis such as zileuton for the treatment of asthma, or an inducible nitric oxide synthase inhibitor.

In another embodiment, the active compound is administered in combination or alternation with one or more other prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

In another embodiment, the active compound is administered in combination or alternation with one or more other $\beta_2$-adrenergic agonist(s) ($\beta$ agonists). Examples of $\beta_2$-adrenergic agonists ($\beta$ agonists) that can be used in alternation or combination therapy include but are not limited to albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Aldlometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Forrnocortal, Halcinonide, Halobetasol Propionate, Halometasone, Hydrocortamnate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other antihistamine(s) ($H_1$ receptor antagonists). Examples of antihistamines ($H_1$ receptor antagonists) that can be used in alternation or combination therapy include alkylamines, ethanolamines, ethylenediamines, piperazines, piperidines or phenothiazines. Some non-limiting examples of antihistamines are Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphenhydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

Alternatively, the compound of the present invention is administered in combination or alternation with (a) xanthines and methylxanthines, such as Theo-24 (theophylline, Slo-Phyllin, Uniphyllin, Slobid, Theo-Dur), Choledyl (oxitriphylline), aminophylline;
(b) anticholinergic agents (antimuscarinic agents) such as belladonna alkaloids, Atrovent (ipratropium bromide), atropine, oxitropium bromide;
(c) phosphodiesterase inhibitors such as zardaverine;
(d) calcium antagonists such as nifedipine; or
(e) potassium activators such as cromakalim for the treatment of asthma.

Arthritic Disorders

In one embodiment, the compound of the present invention can also be administered in combination or alternation with apazone, amitriptyline, chymopapain, collegenase, cyclobenzaprine, diazepam, fluoxetine, pyridoxine, ademetionine, diacerein, glucosamine, hylan (hyaluronate), misoprostol, paracetamol, superoxide dismutase mimics, TNFα receptor antagonists, TNFα antibodies, P38 Kinase inhibitors, tricyclic antidepressants, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-$D_4$-receptor antagonists such as Accolate (zafirlukast), Ziflo (zileuton), leukotriene $C_1$, $C_2$ antagonists and inhibitors of leukotriene synthesis such as zileuton for the treatment of arthritic disorders, inducible nitric oxide sythase inhibitors.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamnethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine hydrochloride, Bomyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

VI. Pharmaceutical Compositions

The described derivative of triptolide can be formulated as pharmaceutical compositions and administered for any of the disorders described herein, including autoimmune and inflammitory disorders, in a host, including a human, in any of a variety of forms adapted to the chosen route of administration, including systemically, such as orally, or parenterally, by intravenous, intramuscular, topical, transdermal or subcutaneous routes.

The derivative of triptolide (or prodrug thereof) is included in the pharmaceutically acceptable carrier or diluent in an amount sufficient to deliver to a patient a therapeutically effective amount of compound to treat autoimmune or anti-inflammatory disorders or the symptoms thereof in vivo without causing serious toxic effects in the patient treated.

A preferred dose of the derivatives of triptolide for all of the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the prodrug can be calculated based on the weight of the parent derivative to be delivered.

The derivatives of triptolide are conveniently administered in units of any suitable dosage form, including but not limited to one containing 7 to 3000 mg, preferably 70 to 1400 mg of active ingredient per unit dosage form. An oral dosage of 50–1000 mg is usually convenient, and more typically, 50–500 mg.

Ideally the derivatives of triptolide should be administered to achieve peak plasma concentrations of the active compound of from about 0.2 to 70 $\mu$M, preferably about 1.0 to 10 $\mu$M. This may be achieved, for example, by the intravenous injection of an appropriate concentration of the active ingredient, optionally in saline, or administered as a bolus of the active ingredient.

The concentration of the derivative of triptolide in the drug composition will depend on absorption, inactivation and excretion rates of the extract as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The derivative of triptolide may be administered at once, or may be divided into a number of smaller doses to be administered at varying intervals of time.

A preferred mode of administration of the derivative of triptolide is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The derivative of triptolide can be administered as a component of an elixir, suspension, syrup, wafer, chewing gum or the like. A syrup may contain, in addition to the active compounds, sucrose as a sweetening agent and certain preservatives, dyes and colorings and flavors. The derivatives of triptolide can also be mixed with other active materials that do not impair the desired action, or with materials that supplement the desired action, such as antibiotics, antifungal, anti-inflammatories, or other anti-autoimmune compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In another embodiment, the derivatives of triptolide are prepared with carriers that will protect the derivatives against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VII. Synthesis of the Active Compounds

Formylation of a Substituted Phenol

The starting material for this process is a substituted phenol (A), which can be purchased or can be prepared by any known means to those of ordinary skill in the art. In one embodiment, formylation of the compound of formula (A) results in the formation of an aldehyde of formula (B). The said substituted phenol can be coupled with a paraformaldehyde in a compatible solvent at a suitable temperature with the appropriate coupling reagent to yield the corresponding aldehyde. Possible coupling reagents are any reagents that promote coupling, including but not limited to $SnCl_4$, $BF_3$, $AlCl_3$, $FeI_3$, or $ZnCl_2$, preferably $SnCl_4$.

The formylation reaction can be carried out at any temperature that achieves the desired result, i.e., that is suitable for the reaction to proceed at an acceptable rate without promoting decomposition or excessive side products. The preferred temperature is room temperature.

Any reaction solvent can be selected that can achieve the necessary temperature, can solubilize the reaction components and inert to the reagents. Nonlimiting examples are any aprotic solvent including, but not limited to the alkyl solvents, such as hexane and cyclohexane, toluene, acetone, ethyl acetate, dithianes, triethylamine (TEA), tetrahydrofuran (THF), dioxane, acetonitrile, dichloromethane, dichloroethane, diethyl ether, pyridine, dimethylformamide (DMF), dimethylsulfoxide (DMSO), dimethylacetamide or any combination thereof, though preferably TEA.

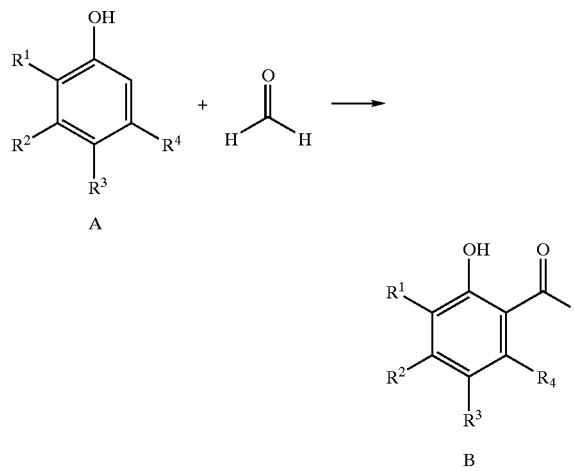

wherein $R^1$, $R^3$, and $R^4$ are selected independently from the groups that include hydrogen, alkyl, alkenyl, alkynyl, cycloalkyl, cycloalkenyl, cycloalkynyl, aryl, alkaryl, arylalkyl, heterocyclic, heteroaryl, heteroaromatic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, a residue of a natural or synthetic amino acid, or carbohydrate or $XR^7$ (X=O, $NR^8$ or S).

Reduction of Aldehyde

In another embodiment of the present invention, reducing the compound of formula B results in the formation of the alcohol of formula C using a reducing agent such as $NaBH_4$. The reduction reaction can be carried out at any temperature that achieves the desired result, i.e., that is suitable for the reaction to proceed at an acceptable rate without promoting decomposition or excessive side products. The preferred temperature is room temperature.

Any reaction solvent can be selected that can achieve the necessary temperature, can solubilize the reaction components and inert to the reagents. Nonlimiting examples are any aprotic solvent including, but not limited to the alkyl solvents, such as hexane and cyclohexane, toluene, acetone, ethyl acetate, dithianes, triethylamine (TEA), tetrahydrofuran (THF), dioxane, acetonitrile, dichloromethane, dichloroethane, diethyl ether, pyridine, dimethylformamide (DMF), dimethylsulfoxide (DMSO), dimethylacetamide or any combination thereof, though preferably TEA.

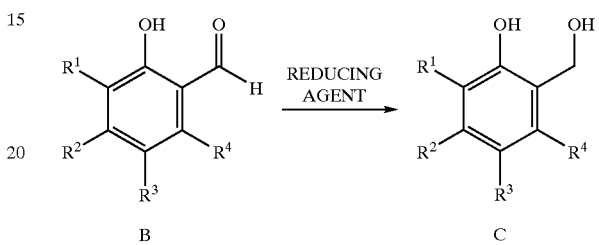

wherein $R^1$, $R^3$, and $R^4$ are selected independently from the groups that include hydrogen, alkyl, alkenyl, alkynyl, cycloalkyl, cycloalkenyl, cycloalkynyl, aryl, alkaryl, arylalkyl, heterocyclic, heteroaryl, heteroaromatic, sulfonyl, sulfanyl, sulfinyl, sulfamonyl, carboxylic acid, amide, nitro, cyano, azide, phosphonyl, phosphinyl, phosphoryl, phosphine, carbamate, ester, alkcarbonyl, carbonyl, a residue of a natural or synthetic amino acid, or carbohydrate or $XR^7$ (X=O, $NR^8$ or S).

Coupling of a Substituted Phenol

Alternatively, the substituted phenol can be formed using a ketone. Again, the starting material for this process is a substituted phenol (A), which can be purchased or can be prepared by any known means to those of ordinary skill in the art. In one embodiment, the compound of formula (A), is optionally protected, with an appropriate protecting group, as taught by Greene et al. *Protective Groups in Organic Synthesis*, John Wiley and Sons, Second Edition, 1991. Coupling of this optionally protected alcohol with an appropriate ketone results in the direct formation of an alcohol of formula (C'). The said substituted phenol can be coupled with the ketone in a compatible solvent at a suitable temperature with the appropriate base to yield the corresponding aldehyde. Possible coupling reagents are any reagents that promote coupling, including but not limited to lithiates, including, BuLi.

The formylation reaction can be carried out at any temperature that achieves the desired result, i.e., that is suitable for the reaction to proceed at an acceptable rate without promoting decomposition or excessive side products. The preferred temperature is room temperature.

Any reaction solvent can be selected that can achieve the necessary temperature, can solubilize the reaction components and inert to the reagents. Nonlimiting examples are any aprotic solvent including, but not limited to the alkyl solvents, such as hexane and cyclohexane, toluene, acetone, ethyl acetate, dithianes, triethylamine (TEA), tetrahydrofuran (THF), dioxane, acetonitrile, dichloromethane, dichloroethane, diethyl ether, pyridine, dimethylformamide (DMF), dimethylsulfoxide (DMSO), dimethylacetamide or any combination thereof, though preferably TEA.

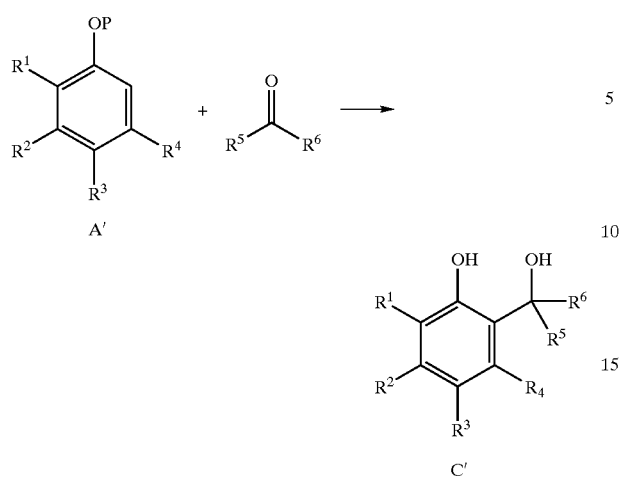

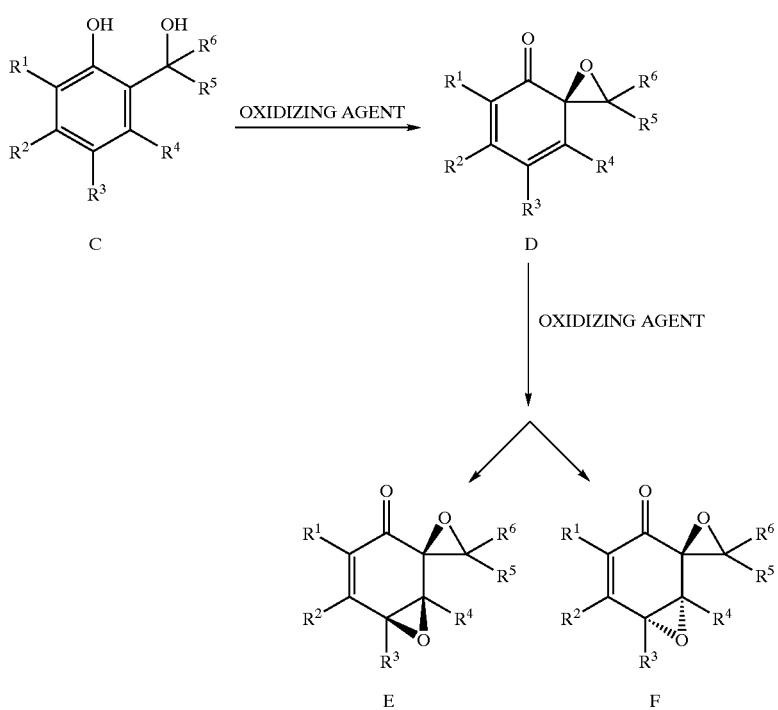

Any reaction solvent can be selected that can achieve the necessary temperature, can solubilize the reaction components and inert to the reagents. Nonlimiting examples are any aprotic solvent including, but not limited to the alkyl solvents, such as hexane and cyclohexane, toluene, acetone, ethyl acetate, dithianes, triethylamine (TEA), tetrahydrofuran (THF), dioxane, acetonitrile, dichloromethane, dichloroethane, diethyl ether, pyridine, dimethylformamide (DMF), dimethylsulfoxide (DMSO), dimethylacetamide or any combination thereof, though preferably TEA.

Formation of Epoxides

In yet a further embodiment of the present invention, the epoxidation of the compounds of formula (C) or (C') yields compound (D). In another embodiment of the present invention, the compound of formula (D) is subjected to further oxidation resulting in the compound of formula (E) and (F). The formation of the monoepoxide (D) results from oxidizing the alcohol of formula (C) with an oxidizing agent such as sodium periodate ($NaIO_4$). Upon further oxidation of the monoepoxide (D) using oxidizing agents such as mCPBA give rise to the compound of formula (E) and (F). The oxidation reaction can be carried out at any temperature that achieves the desired result, i.e., that is suitable for the reaction to proceed at an acceptable rate without promoting decomposition or excessive side products. The preferred temperature is room temperature.

It is yet a further embodiment of the present in invention to further oxidize the compounds of formula (E) or (F) to give the stereoselective compounds of formula (G) or (H) respectively. Treating the compounds of formula (E) or (F) with an oxidizing agent such as hydrogen peroxide/NaOH yield the triepoxide (G) or (H) respectively. The oxidation reaction can be carried out at any temperature that achieves the desired result, i.e., that is suitable for the reaction to proceed at an acceptable rate without promoting decomposition or excessive side products. The preferred temperature is room temperature.

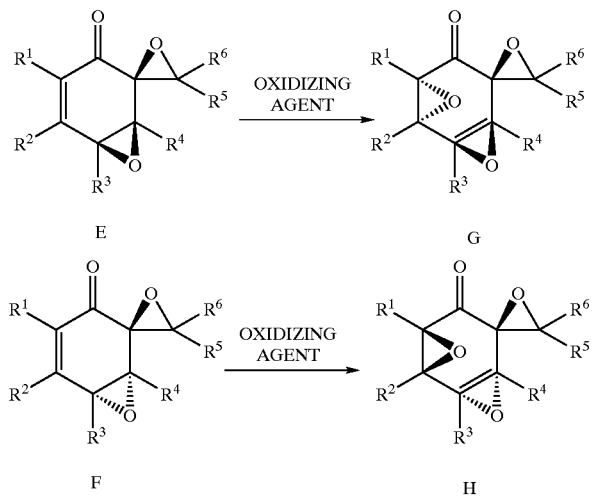

E

G

F

H

It is also a further embodiment of the present invention to provide for the compound of formula (J). The monoepoxide compound of formula (D) can be further oxidized to give the diepoxide compound of formula (J) using oxidizing agents such as hydrogen peroxide/NaOH. The oxidation reaction can be carried out at any temperature that achieves the desired result, i.e., that is suitable for the reaction to proceed at an acceptable rate without promoting decomposition or excessive side products. The preferred temperature is room temperature.

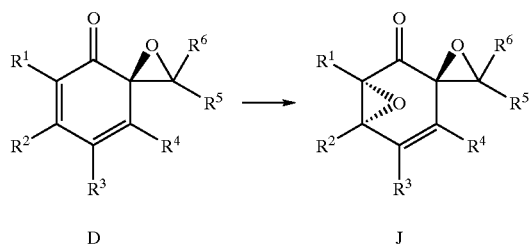

D

J

In another embodiment of the invention, the sulfur analogs are desired. Therefore, the sulfur analogs corresponding to the compounds of the invention can be prepared following the same foregoing general methods, beginning with the corresponding sulfur containing starting material.

Formation of Cyclopropyls

In yet a further embodiment of the present invention, the cyclopropanation of the compounds of formula (C) or (C') yields compound (K). The formation of compound (K) results from eliminating the alcohol of formula (C) with an acid to form the alkene. The alkene can be reacted with the appropriate carbene to form the cyclopropane (K). The appropriate carbene can be made by any means known in the art. In particular, the carbene can be made via α-elimination. For example, dichlorocarbene can be made by treatment of chloroform with a base. Alternatively, the carbene can be made via the Simmons-Smith procedure with Zn—Cu, or Zn and Cu—X (wherein X is a halide), and in particular Zn and Cu—X in the presence of $TiX_4$. The carbene also can be made by the disintegration of certain types of double bonds, such as the photolysis of a ketene, the isoelectronic decomposition of diazoalkanes, and the decomposition of diazirines (which are isometric with diazoalkanes). Alternatively, ylides, such as $R_2P{\equiv}CR^7$, $R_2S(O)$—$CR^7R^8$, such as Trost's and Corey's sulfur ylides, or $R(NR_2)S(O)$—$CR^7R^8$, that mimic a carbene, or transition metal-carbene complexes, such as $L_nM{=}CR^7R^8$, wherein M is a metal and L is a ligand, and in particular, when M is Fe, may also be used to form the desired cyclopropane.

Regardless, the coupling reaction with the carbene can be carried out at any temperature that achieves the desired result, i.e., that is suitable for the reaction to proceed at an acceptable rate without promoting decomposition or excessive side products. The preferred temperature is room temperature. In the same way, any of the carbon—carbon pi bonds in compound (C) or (C') can be reacted with the appropriate carbene to form the desired cyclopropane.

Any reaction solvent can be selected that can achieve the necessary temperature, can solubilize the reaction components and inert to the reagents. Nonlimiting examples are any aprotic solvent including, but not limited to the alkyl solvents, such as hexane and cyclohexane, toluene, acetone, ethyl acetate, dithianes, triethylamine (TEA), tetrahydrofuran (THF), dioxane, acetonitrile, dichloromethane, dichloroethane, diethyl ether, pyridine, dimethylformamide (DMF), dimethylsulfoxide (DMSO), dimethylacetamide or any combination thereof, though preferably TEA.

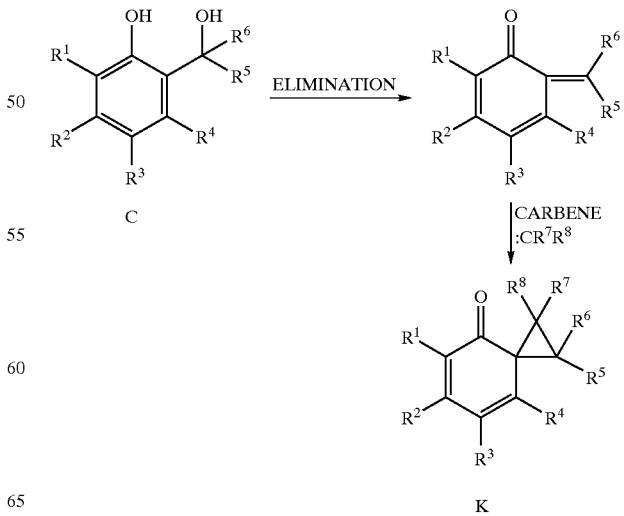

C

K

EXAMPLE 1

Synthesis of Substituted Benzyl Alcohols

To a magnetically stirred solution of the phenol (20 mmol) in toluene (10 mL), triethylamine (8 mmol) was added followed by SnCl$_4$ (2 mmol). After stirring for 0.5 h at room temperature, paraformaldehyde (40 mmol) was added and the slurry heated to 95° C. for 16 h. The reaction mixture was cooled and poured into water (40 mL) and acidified to pH12 with 1 N HCl. The aqueous layer was extracted with diethyl ether (3×60 mL). The combined organics were washed with brine, dried (sodium sulphate) and concentrated under vacuo. The crude product (B) was subjected to reduction with NaBH$_4$ (1.5 equivalents) in MeOH at 0° C. After stirring the reaction for 1 h, the reaction mixture was quenched with a saturated solution of ammonium chloride and acidified to pH 4 with 1 N HCl. MeOH was removed under vacuum and the aqueous layer extracted with ethyl acetate (2×50 mL). The combined organics were washed with brine, dried (sodium sulfate) and concentrated under vacuo. Flash chromatography using 1:4::ethyl acetate:hexanes yielded the desired product C in moderate yield over 2 steps (35–60%).

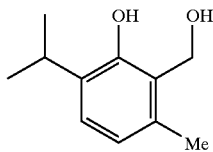

$^1$H NMR (CDCl$_3$): 7.9 (br s, 1H), 7.06 (d, 1H, J=7.8 Hz), 6.7 (d, 1H, J=7.8 Hz), 4.94 (s, 2H), 3.3 (m, 1H), 2.24 (s, 3H), 1,24 (d, 6H, J=6.9 Hz). $^{13}$C NMR (CDCl$_3$): 154.02, 133.90, 132.89, 125.62, 122.19, 121.90, 61.38, 26.75, 22.98, 19.40.

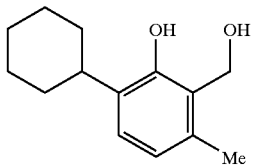

$^1$H NMR (CDCl$_3$): 7.92 (br s, 1H), 7.04 (d, 1H, J=7.8 Hz), 4.93 (s, 2H), 2.9 (m, 1H), 2.23 (s, 3H), 1.8 (m, 6H), 1.36 (m, 4H).

$^{13}$C NMR (CDCl$_3$): 153.91, 133.11, 132.85, 126.12, 122.20, 121.90, 61.33, 36.88, 33.5, 27.35, 26.69, 19.39.

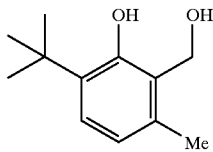

$^1$H NMR (CDCl$_3$): 8.1 (br s, 1H), 7.15 (d, 1H, J=7.8 Hz), 6.67 (d, 1H, J=7.8 Hz), 4.92 (s, 2H), 2.25 (s, 3H), 1.43 (s, 9H).

$^{13}$C NMR (CDCl$_3$): 156.17, 135.36, 133.54, 126.43, 123.06, 121.55, 61.26, 34.69, 29.84, 19.26.

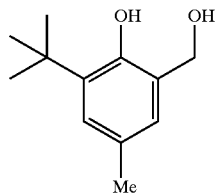

$^1$H NMR (CDCl$_3$): 7.48 (s, 1H), 7.02 (s, 1H), 6.68 (s, 1H), 4.78 (s, 2H), 2.22 (s, 3H), 1.38 (s, 9H).
$^{13}$C NMR (CDCl$_3$): 153.15, 137.19, 128.41, 127.79, 126.49, 124.80, 65.20, 34.76, 29.81, 20.85

EXAMPLE 2

Formation of Monoepoxide Using Sodium Periodate

To a magnetically stirred solution of C (2 mmol) in MeOH (12 mL), a solution of NaIO$_4$ (2.2 mmol) in 3 mL water was added dropwise at 0° C. After one minute of stirring a precipitate began to appear. After stirring for another 20 minutes the precipitate was filtered and washed with CHCl$_3$. Water was added and the aqueous layer was extracted with chloroform. The combined organics were washed with brine, dried (sodium sulfate) and concentrated under vacuo. Purification by flash chromatography using 1:7::ethyl acetate:hexanes yielded the desired product (D, 80%).

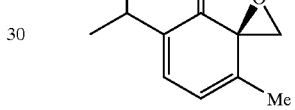

$^1$H NMR (CDCl$_3$): 6.87 (d, 1H, J=6.6 Hz), 6.3 (m, 1H), 3.22 (d, 1H, J=8.1 Hz), 3.15 (d, 1H, J=8.1 Hz), 2.9 (m, 1H), 1.79 (d, 3H, J=1.5 Hz), 1.08 (d, 3H, J=2.1 Hz), 1.05 (d, 3H, J=2.1 Hz).
$^{13}$C NMR (CDCl$_3$): 195.31, 144.45, 141.75, 135.62, 124.02, 59.27, 58.81, 26.45, 22.14, 21.88, 16.42.

$^1$H NMR (CDCl$_3$): 6.8 (m, 1H), 6.23 (m, 1H), 3.14 (m, 1H), 3.05 (m, 1H), 2.52 (m, 1H), 1.65 (m, 8H), 1.27 (m, 2H), 1.1 (m, 3H)
$^{13}$C NMR (CDCl$_3$): 195.41, 144.30, 140.89, 136.13, 124.10, 59.12, 58.70, 35.79, 32.56, 32.31, 26.68, 26.59, 26.28, 16.15.

$^1$H NMR (CDCl$_3$): 6.94 (d, 1H, J 6.3 Hz), 6.27 (d, 1H, J=6.3 Hz), 3.14 (AB quartet, 2H, J=8.1 Hz), 1.79 (s, 3H), 1.21 (s, 9H).
$^{13}$C NMR (CDCl$_3$): 195.07, 145.18, 143.06, 136.44, 123.98, 59.85, 58.44, 34.34, 29.14, 16.19.

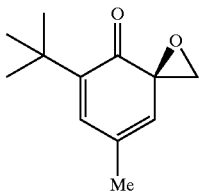

¹H NMR (CDCl₃): 6.79 (d, 1H, J=2.1 Hz), 5.68 (d, 1H, J=2.1 Hz), 3.23 (d, 1H, J=8.1 Hz), 3.01 (d, 1H, J=8.1 Hz), 1.98 (s, 3H), 1.20 (s, 9H).

¹³C NMR (CDCl₃): 194.42, 144.74, 140.25, 135.79, 130.94, 58.92, 57.26, 34.55, 29.23, 22.00.

EXAMPLE 3

Formation of Diepoxides from the Monoepoxides Using mCPBA

To a magnetically stirred solution of D (1 mmol) in methylene chloride (10 mL), mCPBA was added and the reaction mixture stirred for 14 h. The mixture was diluted with methylene chloride and washed twice with saturated sodium carbonate. The combined organics were washed with brine, dried (sodium sulfate) and concentrated under vacuo. Purification by flash chromatography using 1:7::ethyl acetate:hexanes yielded 2 products that were separated. Stereochemical assignments were made by comparison with literature data. Typically the higher $R_F$ spot was assigned the stereochemistry F and the lower $R_F$ spot was assigned the stereochemistry E. The combined yield for the reaction was typically 70%.

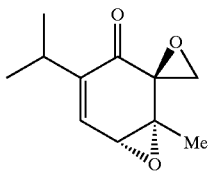

¹H NMR (CDCl₃): 6.95 (d, 1H, J=4.5 Hz), 3.46 (d, 1H, J=4.5 Hz), 3.42 (d, 1H, J=6.6 Hz), 3.1 (d, 1H, J=6.6 Hz), 2.85 (m, 1H), 1.31 (s, 3H), 1.04 (d, 3H, J=5.1 Hz), 1.02 (d, 3H, J=5.1 Hz).

¹³C NMR (CDCl₃): 190.71, 149.44, 136.89, 61.39, 55.66, 54.43, 50.11, 27.40, 21.67, 21.64, 16.16.

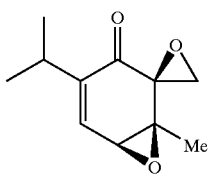

¹H NMR (CDCl₃): 6.9 (d, 1H, J=4.5 Hz), 3.51 (d, 1H, J=4.8 Hz), 2.96 (d, 1H, J=6.3 Hz), 2.87 (d, 1H, J=6.3 Hz), 2.79 (m, 1H), 1.32 (s, 3H), 1.06 (d, 3H, J=6.9 Hz), 0.97 (d, 3H, J=6.9 Hz).

¹³C NMR (CDCl₃): 191.06, 150.00, 136.40, 59.62, 57.92, 54.55, 52.66, 27.51, 21.69, 21.55, 15.63.

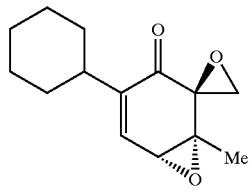

¹H NMR (CDCl₃): 6.89 (d, 1H, J=3.3 Hz), 3.44 (d, 1H, J=3.3 Hz), 3.38 (d, 1H, J=4.8 Hz), 3.09 (d, 1H, J=4.8 Hz), 2.49 (m, 1H), 1.71 (m, 5H), 1.3 (s, 3H), 1.33–1.03 (m, 5H).

¹³C NMR (CDCl₃): 190.89, 148.72, 137.42, 61.3, 55.59, 54.42, 50.04, 36.85, 32.25, 26.58, 26.56, 26.26, 16.02.

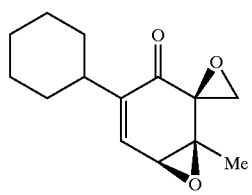

¹H NMR (CDCl₃): 6.83 (d, 1H, J=3.6 Hz), 3.5 (d, 1H, J=3.6 Hz), 2.94 (m, 1H), 2.82 (m, 1H), 2.45 (br t, 1H), 1.73–1.52 (m, 5H), 1.13 (s, 3H), 1.26–0.96 (m, 5H)

¹³C NMR (CDCl₃): 191.27, 149.21, 136.87, 59.58, 57.76, 54.52, 36.85, 32.31, 31.99, 26.50, 26.41, 26.14, 15.39.

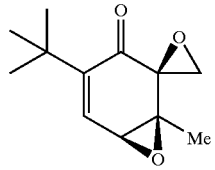

¹H NMR (CDCl₃): 6.92 (d, 1H, J=3.3 Hz), 3.49 (d, 1H, J=3.3 Hz), 2.89 (d, 1H, J=4.2 Hz), 2.79 (d, 1H, J=4.2 Hz), 1.31 (s, 3H), 1.14 (s, 9H).

¹³C NMR (CDCl₃): 191.21, 151.52, 136.77, 60.76, 57.35, 54.44, 51.60, 35.05, 28.90, 14.97.

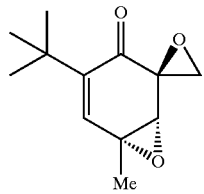

¹H NMR (CDCl₃): 6.78 (s, 1H), 3.44 (d, 1H, J=6.6 Hz), 3.21 (s, 1H), 3.03 (d, 1H, J=6.6 Hz), 1.57 (s, 3H), 1.12 (s, 9H).

¹³C NMR (CDCl₃): 190.07, 149.46, 142.55, 63.23, 54.31, 54.00, 51.34, 35.16, 29.05, 21.07.

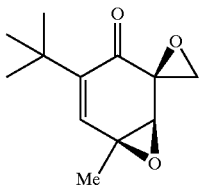

$^1$H NMR (CDCl$_3$): 6.72 (s, 1H), 3.13 (s, 1H), 2.89 (s, 2H), 1.57 (s, 3H), 1.09 (s, 9H).

$^{13}$C NMR (CDCl$_3$): 190.07, 150.01, 142.08, 60.59, 58.08, 54.85, 52.96, 35.03, 28.98, 21.11.

EXAMPLE 4

Oxidation of Monoepoxides and Diepoxides to Diepoxides and Triepoxides Respectively Using Hydrogen Peroxide To a magnetically stirred solution of D or F or E (1 mmol) in MeOH (10 mL) at room temperature, 1 N NaOH (0.47 mL) was added followed immediately by the addition of 30% H$_2$O$_2$ (1.5 mmol). After 40 minutes of stirring at room temperature, water was added (40 mL) and the aqueous layer extracted with ethyl acetate (3×60 mL). The combined organics were washed with brine, dried (sodium sulfate) and concentrated under vacuo. Flash chromatography using 1;6::ethyl acetate:hexanes yielded the desired product J, H or G respectively in moderate yield (60%).

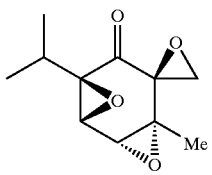

$^1$H NMR (CDCl$_3$): 3.81 (d, 1H, J=2.4 Hz), 3.62 (d, 1H, J=2.4 Hz), 3.38 (d, 1H, J=5.2 Hz), 2.9 (d, 1H, J=5.2 Hz), 2.39 (m, 1H), 1.23 (s, 3H), 0.96 (d, 3H, J=6.8 Hz), 0.87(d, 3H, J=6.8 Hz).

$^{13}$C NMR (CDCl$_3$): 198.03, 66.15, 59.2, 58.72, 58.5, 56.59, 47.43, 26.02, 18.24, 16.37, 15.62.

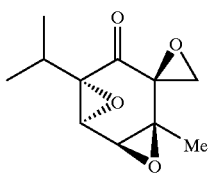

$^1$H NMR (CDCl$_3$): 3.85 (d, 1H, J=2.8 Hz), 3.67(d, 1H, J=2.8 Hz), 2.95 (d, 1H, J=5.2 Hz), 2.74 (d, 1H, J=5.2 Hz), 2.4 (m, 1H), 1.23 (s, 3H), 0.96 (d, 3H, J=6.8 Hz), 0.87 (d, 3H, J=6.8 Hz)

$^{13}$C NMR (CDCl$_3$): 197.67, 67.22, 60.32, 59.53, 58.43, 50.69, 25.75, 18.11, 16.65, 14.73.

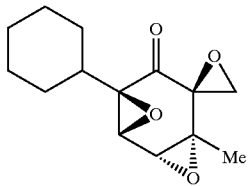

$^1$H NMR (CDCl$_3$): 3.84 (d, 1H, J=2.8 Hz), 3.61 (d, 1H, J=2.8 Hz), 3.36 (d, 1H, J=4.2 Hz), 2.98 (d, 1H, J=4.2 Hz), 2.12 (m, 1H), 1.74–1.58 (m, 5H), 1.23 (s, 3H), 1.28–0.87 (m, 5H).

$^{13}$C NMR (CDCl$_3$): 198.04, 65.85, 59.27, 58.78, 58.44, 56.68, 47.42, 35.07, 28.53, 26.49, 26.24, 26.00, 25.91, 15.57.

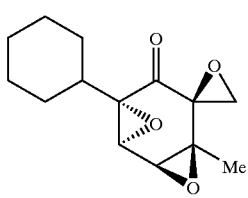

$^1$H NMR (CDCl$_3$): 3.88 (d, 1H, J=2.8 Hz), 3.66 (d, 1H, J=2.8 Hz), 2.94 (d, 1H, J=5.2 Hz), 2.72 (d, 1H, J=5.2 Hz), 2.15 (m, 1H), 1.73–1.63 (m, 5H), 1.22 (s, 3H), 1.28–0.89 (m, 5H).

$^{13}$C NMR (CDCl$_3$): 197.66, 66.93, 60.42, 60.31, 59.48, 58.48, 50.59, 34.64, 28.34, 26.74, 26.16, 25.91, 14.66.

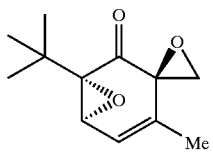

$^1$H NMR (CDCl$_3$): 6.08 (m, 1H), 3.73 (d, 1H, J=3 Hz), 2.94 (s, 2H), 1.61 (s, 3H), 1.09 (s, 9H).

$^{13}$C NMR (CDCl$_3$): 200.05, 141.71, 123.21, 64.42, 60.21, 56.4, 52.92, 32.10, 25.76, 15.67.

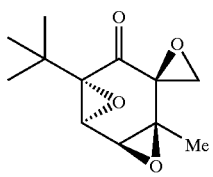

$^1$H NMR (CDCl$_3$): 3.92 (d, 1H, J=3 Hz), 3.62 (d, 1H, J=3 Hz), 2.89 (d, 1H, J=5.1 Hz), 2.67 (d, 1H, J=5.1 Hz), 1.19 (s, 3H), 1.00 (s, 9H).

$^{13}$C NMR (CDCl$_3$): 196.86, 68.49, 61.05, 60.19, 59.46, 58.12, 50.22, 32.31, 25.65, 14.47

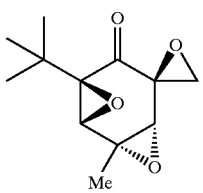

$^1$H NMR (CDCl$_3$): 3.72 (s, 1H), 2.95 (d, 1H, J=5.4 Hz), 2.81 (d, 1H, J=5.4 Hz), 1.66 (s, 3H), 1.01 (s, 9H)
$^{13}$C NMR (CDCl$_3$): 196.56, 68.30, 64.58, 61.63, 59.03, 58.30, 51.04, 32.43, 25.79, 20.13.

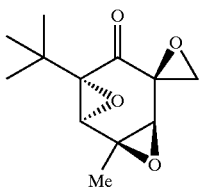

$^1$H NMR (CDCl$_3$): 3.72, (d, 1H, J=1.5 Hz), 3.41 (d, 1H, J=5.7 Hz), 2.8 (m, 2H), 1.64 (s, 3H), 1.01 (s, 9H).
$^{13}$C NMR (CDCl$_3$): 196.94, 67.45, 63.68, 60.50, 58.29, 54.5, 50.79, 32.45, 25.92, 19.97.

We claim:

1. A compound of the formula (V):

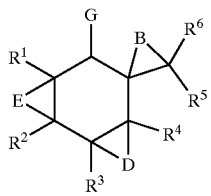

or its pharmaceutically acceptable salt thereof, wherein:
(a) B, D and E are independently O;
(b) G is OR$^{11}$, NR$^{11}$R$^{12}$ or SR$^{11}$;
(c) R$^1$, R$^2$, R$^3$, R$^4$, R$^5$ and R$^6$ are independently hydrogen, alkyl, alkenyl, alkynyl, aryl, alkaryl, arylalkyl; a moiety selected from optionally substituted furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, and imidazole; and
(d) each R$^7$, R$^8$, R$^9$, R$^{10}$, R$^{11}$ and R$^{12}$ is independently hydrogen, alkyl, alkenyl, alkynyl, aryl, alkaryl, arylalkyl; a moiety selected from optionally substituted furyl furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, and imidazole.

2. A pharmaceutical composition for the treatment of an inflammatory disorder in a host comprising an effective treatment amount of a compound according to claim 1 in a pharmaceutically acceptable carrier or diluent.

3. A compound of formula:

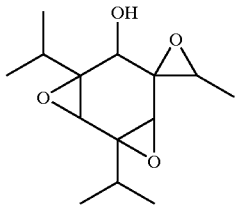

or its pharmaceutically acceptable salt thereof.

4. A pharmaceutical composition for the treatment of an inflammatory disorder in a host comprising an effective treatment amount of a compound of formula:

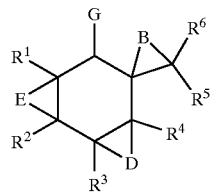

or its pharmaceutically acceptable salt thereof, wherein:
(a) B, D and E are independently O;
(b) G is OR$^{11}$, N$^{11}$R$^{12}$ or SR$^{11}$;
(c) R$^1$, R$^2$, R$^3$, R$^4$, R$^5$ and R$^6$ are independently hydrogen, alkyl, alkenyl, alkynyl, aryl, alkaryl, arylalkyl; a moiety selected from optionally substituted furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, and imidazole and
each R$^7$, R$^8$, R$^9$, R$^{10}$, R$^{11}$ and R$^{12}$ is independently hydrogen, alkyl, alkenyl, alkynyl, aryl, alkaryl, arylalkyl; a moiety selected from optionally substituted furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl cinnolinyl, phthalazinyl, xanthinyl, hypoxanthinyl thiophene, furan, pyrrole, isopyrrole, pyrazole, and imidazole:
in a pharmaceutically acceptable carrier in combination with other anti-inflammatory agents.

5. The pharmaceutical composition of claim 2, or 4, wherein the host is a human.

6. The pharmaceutical composition of claim 2, or 4, wherein the compound is in the form of a dosage unit.

7. The pharmaceutical composition according to claim 6, wherein the dosage unit contains 7 to 3000 mg of the compound.

8. The pharmaceutical composition according to claim 6, wherein the dosage unit contains 70 to 1400 mg of the compound.

9. The pharmaceutical composition according to claim 6, wherein the dosage unit contains 50–500 mg of the compound.

10. The pharmaceutical composition according to claim 4, wherein the dosage unit is a tablet or capsule.

11. The pharmaceutical composition according to claim 4, wherein the anti-inflammatory agent is selected from the group consisting of heparin, frusemide, ranitidine, an agent that effects respiratory function, immunosuppressive agents, IV gamma globulin, troleandomycin, cyclosporin (Neoral), methotrexate, FK-506, gold compounds, platelet activating factor (PAF), leukotriene-$D_4$-receptor antagonists), Ziflo (zileuton), leukotriene $C_1$ or $C_2$ antagonists and inhibitors of leukotriene synthesis, and an inducible nitric oxide synthase inhibitor.

12. The pharmaceutical composition of claim 4, the anti-inflammatory agent is selected from the group consisting $\beta_2$-adrenergic agonist ($\beta$ agonists).

13. The pharmaceutical composition of claim 12, wherein the $\beta$ agonist is selected from the group consisting of albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

14. The pharmaceutical composition according claim 4, wherein the anti-inflammatory agent is selected from the group consisting of a corticosteroid, antihistamine ($H_1$ receptor antagonists), xanthines and methylxanthines, anticholinergic agents (antimuscarinic agents), and phosphodiesterase inhibitors.

15. A pharmaceutical composition for the treatment of an inflammatory disorder in a host comprising an effective treatment amount of a compound of formula:

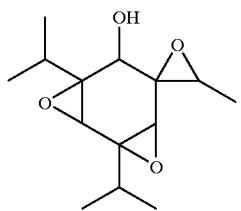

or its pharmaceutically acceptable salt thereof, in a pharmaceutically acceptable carrier or diluent.

16. A pharmaceutical composition for the treatment of an inflammatory disorder in a host comprising an effective treatment amount of a compound of formula:

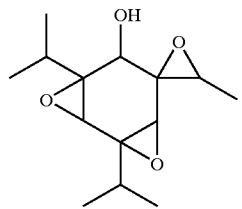

or a pharmaceutically acceptable salt thereof; in a pharmaceutically acceptable carrier, in combination with another anti-inflammatory agent.

17. The pharmaceutical composition of claim 15 or 16, wherein the compound is in the form of a dosage unit.

18. The pharmaceutical composition of claim 17, wherein the dosage unit contains 7 to 3000 mg of the compound.

19. The pharmaceutical composition of claim 17, wherein the dosage unit contains 70 to 1400 mg of the compound.

20. The pharmaceutical composition of claim 17, wherein the dosage unit contains 50–500 mg of the compound.

21. The pharmaceutical composition of claim 17, wherein the dosage unit is a tablet or capsule.

22. The pharmaceutical composition of claim 16, wherein the anti-inflammatory agent is selected from the group consisting of heparin, frusemide, ranitidine, an agent that effects respiratory function, immunosuppressive agents, IV gamma globulin, troleandomycin, cyclosporin (Neoral), methotrexate, FK-506, gold compounds, platelet activating factor (PAF), leukotriene-$D_4$-receptor antagonists), Ziflo (zileuton), leukotriene $C_1$ or $C_2$ antagonists and inhibitors of leukotriene synthesis, and an inducible nitric oxide synthase inhibitor.

23. The pharmaceutical composition of claim 16, wherein the anti-inflammatory agent is selected from the group consisting $\beta_2$-adrenergic agonist ($\beta$ agonists).

24. The pharmaceutical composition of claim 23, wherein the $\beta$ agonist is selected from the group consisting of albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

25. The pharmaceutical composition of claim 16, wherein the anti-inflammatory agent is selected from the group consisting of a corticosteroid, antihistamine ($H_1$ receptor antagonists), xanthines and methylxanthines, anticholinergic agents (antimuscarinic agents), and phosphodiesterase inhibitors.

26. The pharmaceutical composition of any one of claims 15 or 38, wherein the host is a human.

27. The compound of claim 1 wherein G is $OR^{11}$.

28. The compound of claim 1 wherein G is $NR^{11}R^{12}$.

29. The compound of claim 1 wherein G is $SR^{11}$.

30. The compound of claim 1 wherein at least one of $R^1$, $R^2$, $R^3$, $R^4$, $R^5$ and $R^6$ is an alkyl group.

31. The compound of claim 1 wherein at least one of $R^1$, $R^2$, $R^3$, $R^4$, $R^5$ and $R^6$ is an alkenyl group.

32. The compound of claim 1 wherein at least one of $R^1$, $R^2$, $R^3$, $R^4$, $R^5$ and $R^6$ is an alkynyl group.

33. The compound of claim 1 wherein at least one of $R^1$, $R^2$, $R^3$, $R^4$, $R^5$ and $R^6$ is an aryl group.

34. The compound of claim 1 wherein at least one of $R^1$, $R^2$, $R^3$, $R^4$, $R^5$ and $R^6$ is an alkaryl group.

35. The compound of claim 1 wherein at least one of $R^1$, $R^2$, $R^3$, $R^4$, $R^5$ and $R^6$ is an arylalkyl group.

36. The compound of claim 1 wherein $R^7$, $R^5$, $R^9$, $R^{10}$, $R^{11}$ and $R^{12}$ are all hydrogen.

37. The compound of claim 1 wherein at least one of $R^7$, $R^8$, $R^9$, $R^{10}$, $R^{11}$ and $R^{12}$ is an alkyl group.

38. The compound of claim 1 wherein at least one of $R^7$, $R^8$, $R^9$, $R^{10}$, $R^{11}$ and is an alkenyl group.

39. The compound of claim 1 wherein at least one of $R^7$, $R^8$, $R^9$, $R^{10}$, $R^{11}$ and $R^{12}$ is an alkynyl group.

40. The compound of claim 1 wherein at least one of $R^7$, $R^8$, $R^9$, $R^{10}$, $R^{11}$ and $R^{12}$ is an aryl group.

41. The compound of claim 1 wherein at least one of $R^7$, $R^8$, $R^9$, $R^{10}$, $R^{11}$ and $R^{12}$ is an alkaryl group.

42. The compound of claim 1 wherein at least of $R^7$, $R^8$, $R^9$, $R^{10}$, $R^{11}$ and $R^{12}$ is an arylalkyl group.

* * * * *